US009988667B2

(12) United States Patent
Craighead et al.

(10) Patent No.: US 9,988,667 B2
(45) Date of Patent: *Jun. 5, 2018

(54) DEVICE AND METHODS FOR EPIGENETIC ANALYSIS

(71) Applicant: Cornell University, Ithaca, NY (US)

(72) Inventors: Harold G. Craighead, Ithaca, NY (US); Benjamin R. Cipriany, Ithaca, NY (US); Stephen Levy, Ithaca, NY (US); Paul Soloway, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/249,275

(22) Filed: Aug. 26, 2016

(65) Prior Publication Data

US 2017/0073741 A1     Mar. 16, 2017

Related U.S. Application Data

(60) Continuation of application No. 14/260,082, filed on Apr. 23, 2014, now Pat. No. 9,447,451, which is a division of application No. 13/367,300, filed on Feb. 6, 2012, now Pat. No. 8,735,065, which is a continuation-in-part of application No. PCT/US2010/044806, filed on Aug. 6, 2010, and a continuation-in-part of application No. PCT/US2010/044810, filed on Aug. 6, 2010.

(60) Provisional application No. 61/231,979, filed on Aug. 6, 2009, provisional application No. 61/231,963, filed on Aug. 6, 2009, provisional application No. 61/307,827, filed on Feb. 24, 2010, provisional application No. 61/359,266, filed on Jun. 28, 2010.

(51) Int. Cl.
*C12Q 1/68* (2018.01)
*B01L 3/00* (2006.01)

(52) U.S. Cl.
CPC .......... *C12Q 1/68* (2013.01); *B01L 3/502761* (2013.01); *C12Q 1/6827* (2013.01); *B01L 2200/0663* (2013.01); *B01L 2300/0654* (2013.01); *C12Q 2537/164* (2013.01); *C12Q 2565/629* (2013.01); *C12Q 2565/631* (2013.01)

(58) Field of Classification Search
None
See application file for complete search history.

(56) References Cited

U.S. PATENT DOCUMENTS

| | | | |
|---|---|---|---|
| 6,221,654 B1 | 4/2001 | Quake et al. |
| 6,833,242 B2 | 12/2004 | Quake et al. |
| 6,927,065 B2 | 8/2005 | Chan et al. |
| 7,267,797 B1 | 9/2007 | Craighead et al. |
| 7,371,520 B2 | 5/2008 | Zhao |
| 7,402,422 B2 | 7/2008 | Fuchs et al. |
| 7,405,434 B2 | 7/2008 | Stavis et al. |
| 8,735,065 B2 | 5/2014 | Craighead et al. |
| 9,447,451 B2 | 9/2016 | Craighead et al. |
| 9,605,298 B2 | 3/2017 | Craighead et al. |
| 2005/0123947 A1 | 6/2005 | Quake et al. |
| 2005/0207940 A1 | 9/2005 | Butler et al. |
| 2006/0228747 A1 | 10/2006 | Fuchs et al. |
| 2007/0003442 A1 | 1/2007 | Link et al. |
| 2007/0154895 A1 | 7/2007 | Spaid et al. |
| 2007/0161028 A1 | 7/2007 | Schwartz et al. |
| 2008/0014589 A1 | 1/2008 | Link et al. |
| 2008/0160622 A1 | 7/2008 | Su et al. |
| 2009/0050542 A1 | 2/2009 | Leary et al. |
| 2009/0234202 A1 | 9/2009 | Goix et al. |
| 2012/0244532 A1 | 9/2012 | Craighead et al. |
| 2012/0245047 A1 | 9/2012 | Craighead et al. |
| 2014/0322710 A1 | 10/2014 | Craighead et al. |

FOREIGN PATENT DOCUMENTS

| | | |
|---|---|---|
| CN | 1735466 A | 2/2006 |
| CN | 101189504 A | 5/2008 |
| CN | 101400437 A | 4/2009 |
| WO | WO-03100101 A1 | 12/2003 |
| WO | WO-2009029957 A1 | 3/2009 |
| WO | WO-2010044932 A2 | 4/2010 |
| WO | WO-2010129787 A2 | 11/2010 |

OTHER PUBLICATIONS

Anway, et al. Epigenetic transgenerational actions of endocrine disruptors and male fertility. Science. Jun. 3, 2005;308(5727):1466-9.
Austin, R. Nanopores: The art of sucking spaghetti. Nat Mater. Sep. 2003;2(9):567-8.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Barski et al. High-resolution profiling of histone methylations in the human genome. Cell 129(4):823-837 (2007).
Bernstein, et al. A bivalent chromatin structure marks key developmental genes in embryonic stem cells. Cell. Apr. 21, 2006;125(2):315-26.
Bernstein, et al. The mammalian epigenome. Cell. Feb. 23, 2007;128(4):669-81.
Chan, et al. DNA mapping using microfluidic stretching and single-molecule detection of fluorescent site-specific tags. Genome Res. Jun. 2004;14(6):1137-46.

(Continued)

*Primary Examiner* — Mindy G Brown
(74) *Attorney, Agent, or Firm* — Wilson Sonsini Goodrich & Rosati

(57) ABSTRACT

Provided herein are methods and devices for single object detection. The methods and devices can be used to identify a plurality of epigenetic markers on a genetic material, or a chromatin, encompassing fragments thereof. The invention provides for the characterization of the genetic material flowing through a channel in a continuous body of fluid based on detection of one or more properties of the genetic material. The methods and systems provided herein allow genome-wide, high-throughput epigenetic analysis and overcome a variety of limitations common to bulk analysis techniques.

14 Claims, 30 Drawing Sheets

(56) References Cited

OTHER PUBLICATIONS

Chinese office action dated Jul. 3, 2013 for CN 201080039585.8. (in Chinese with English translation).
Cipriany, et al. Single molecule epigenetic analysis in a nanofluidic channel. Anal Chem. Mar. 15, 2010;82(6):2480-7.
Dittrich, et al. An integrated microfluidic system for reaction, high-sensitivity detection, and sorting of fluorescent cells and particles. Analytical Chemsitry. 2003; 75(21):5767-5774.
European search report and search opinion dated Apr. 5, 2013 for EP Application No. 10807270.
European search report and search opinion dated Jul. 1, 2016 for EP Application No. 10807274.5.
Feinberg. Phenotypic plasticity and the epigenetics of human disease. Nature. May 24, 2007;447(7143):433-40.
Fielder, et al. Dielectrophoretic sorting of particles and cells in a microsystem. Anal Chem. May 1, 1998;70(9):1909-15.
Foquet, et al. DNA fragment sizing by single molecule detection in submicrometer-sized closed fluidic channels. Anal Chem. Mar. 15, 2002;74(6):1415-22.
Fraga, et al. DNA methylation: a profile of methods and applications. Biotechniques. Sep. 2002;33(3):632, 634, 636-49.
Fu, et al. An integrated microfabricated cell sorter. Analytical Chemistry. 2002; 74(11):2451-2457.
Han, et al. Entropic Trapping and Escape of Long DNA Molecules at Submicron Size Constriction. Physical Review Letters. Aug. 23, 1999; 83(8):1688-1691.
International search report and written opinion dated Apr. 15, 2011 for PCT Application No. US2010/044810.
International search report and written opinion dated Apr. 22, 2011 for PCT Application No. US2010/044806.
Jamieson, et al. Drug discovery with engineered zinc-finger proteins. Nat Rev Drug Discov. May 2003;2(5):361-8.
Jenuwein, et al. Translating the histone code. Science. Aug. 10, 2001;293(5532):1074-80.
Jurney, P. Nano and Microfluidics for Single Molecule Biophysics Applications. NNIN REU Research Accomplishments. 2008;pp. 20-21.
Klose, et al. Genomic DNA methylation: the mark and its mediators. Trends Biochem Sci. Feb. 2006;31(2):89-97. Epub Jan. 5, 2006.
Luger, et al. Crystal structure of the nucleosome core particle at 2.8 A resolution. Nature. 1997; 389:251-260.
Mikkelsen et al. Genome-wide maps of chromatin state in pluripotent and lineage-committed cells. Nature 448(7153):553-560 (2007).
Moscou, et al. A simple cipher governs DNA recognition by TAL effectors. Science. Dec. 11, 2009;326(5959)1501.
Nielsen, et al. Sequence-selective recognition of DNA by strand displacement with a thymine-substituted polyamide. Science. Dec. 6, 1991;254(5037):1497-500.
Notice of allowance dated Jan. 9, 2014 for U.S. Appl. No. 13/367,300.
Notice of allowance dated May 20, 2016 for U.S. Appl. No. 14/260,082.
Notice of allowance dated Nov. 7, 2016 for U.S. Appl. No. 13/389,259.
Office action dated Feb. 9, 2016 for U.S. Appl. No. 14/260,082.
Office action dated Apr. 5, 2013 for U.S. Appl. No. 13/389,259.
Office action dated Apr. 19, 2013 for U.S. Appl. No. 13/367,300.
Office action dated Jul. 11, 2016 for U.S. Appl. No. 13/389,259.
Office action dated Sep. 9, 2015 for U.S. Appl. No. 14/260,082.
Office action dated Sep. 11, 2013 for U.S. Appl. No. 13/367,300.
Office action dated Sep. 13, 2012 for U.S. Appl. No. 13/389,259.
O'Neill, et al. Epigenetic characterization of the early embryo with a chromatin immunoprecipitation protocol applicable to small cell populations. Nat Genet. Jul. 2006;38(7):835-41. Epub Jun. 11, 2006.
Paradowska, et al. Aberrant epigenetic modifications in the CTCF binding domain of the IGF2/H19 gene in prostate cancer compared with benign prostate hyperplasia. Int J Oncol. Jul. 2009;35(1):87-96.
Ren, et al. Genome-wide location and function of DNA binding proteins. Science. Dec. 22, 2000;290(5500):2306-9.
Stavis, et al. Single molecule studies of quantum dot conjugates in a submicrometer fluidic channel. Lab Chip. Mar. 2005;5(3):337-43. Epub Jan. 13, 2005.
Streng, D. E. The Nanofluidic Analysis of Chromatin. NCSU Libraries. Jul. 16, 2009.
Urnov, et al. Highly efficient endogenous human gene correction using designed zinc-finger nucleases. Nature. Jun. 2, 2005;435(7042):646-51. Epub Apr. 3, 2005.
Waterland, et al. Transposable elements: targets for early nutritional effects on epigenetic gene regulation. Mol Cell Biol. Aug. 2003;23(15):5293-300.
Weaver, et al. Epigenetic programming by maternal behavior. Nat Neurosci. Aug. 2004;7(8):847-54. Epub Jun. 27, 2004.
Weber, et al. Chromosome-wide and promoter-specific analyses identify sites of differential DNA methylation in normal and transformed human cells. Nat Genet. Aug. 2005;37(8):853-62. Epub Jul. 10, 2005.
Zhang, et al. Genome-wide high-resolution mapping and functional analysis of DNA methylation in *Arabidopsis*. Cell. Sep. 22, 2006;126(6):1189-201. Epub Aug. 31, 2006.

Time Coincident Events
(indicate bound state)

Figure 13

| | TOTO-3 : Base Ratio | Red Bursts | Burst Duration (msec) | Bursts Coincident with Green | % Bursts Coincident with Green |
|---|---|---|---|---|---|
| RED CHANNEL | None | 1379 | 1.82 | 614 | 44.5% |
| | 1:15 | 23376 | 2.83 | 10994 | 47.0% |
| | 1:10 | 69204 | 1.92 | 35355 | 51.1% |
| | 1:05 | 33854 | 1.79 | 17210 | 50.8% |
| | TOTO-3 : Base Ratio | Green Bursts | Burst Duration (msec) | Bursts Coincident with Red | % Bursts Coincident with Red |
| GREEN CHANNEL | None | 9478 | 3.19 | 617 | 6.5% |
| | 1:15 | 13285 | 3.25 | 11146 | 83.9% |
| | 1:10 | 37321 | 2.43 | 36044 | 96.6% |
| | 1:05 | 18273 | 2.40 | 17351 | 95.0% |

Fluid channel chip with aligned optical
excitation volumes (e.g. 4 of many shown)

DEVICE AND METHODS FOR EPIGENETIC ANALYSIS

CROSS-REFERENCE

This application is a continuation of U.S. patent application Ser. No. 14/260,082, filed Apr. 23, 2014, which is a divisional application of U.S. patent application Ser. No. 13/367,300, filed Feb. 6, 2012, now U.S. Pat. No. 8,735,065, which is a continuation-in-part of PCT Patent Application No. PCT/US2010/044806, filed Aug. 6, 2010, which claims benefit of priority to U.S. Provisional Application No. 61/231,979, filed Aug. 6, 2009, U.S. Provisional Application No. 61/307,827, filed Feb. 24, 2010, U.S. Provisional Application No. 61/231,963, filed Aug. 6, 2009; and U.S. Provisional Application No. 61/359,266, filed Jun. 28, 2010; U.S. patent application Ser. No. 13/367,300, filed Feb. 6, 2012, is also a continuation-in-part of PCT Patent Application No. PCT/US2010/044810, filed Aug. 6, 2010, which claims benefit of priority to U.S. Provisional Application No. 61/231,979, filed Aug. 6, 2009, U.S. Provisional Application No. 61/307,827, filed Feb. 24, 2010, U.S. Provisional Application No. 61/231,963, filed Aug. 6, 2009, and U.S. Provisional Application No. 61/359,266, filed Jun. 28, 2010, each of which is incorporated herein by reference in its entirety for all purposes.

STATEMENT AS TO FEDERALLY SPONSORED RESEARCH

This invention was made with government support under DA025722 awarded by the National Institutes of Health and 9876771 awarded by the National Science Foundation. The government has certain rights in the invention.

BACKGROUND OF THE INVENTION

Chromatin, located in the nucleus of eukaryotic cells, is the complex of DNA with histone proteins, including, H1,H2A, H2B, H3, and H4. The histone proteins are assembled onto DNA in the form of a nucleosome (Luger et al. (1997) *Nature*, 389, 251-260). The DNA sequence carries the genetic code and controls inheritance of traits. However, reversible covalent modifications to specific DNA sequences and their associated histones can influence how the underlying DNA is utilized and can therefore also control traits (Jenuwein and Allis (2001) *Science*, 293, 1074-1080; Klose and Bird (2006) *Trends In Biochemical Sciences*, 31, 89-97). These have been referred to as epigenetic modifications. The most common epigenetic modifications to DNA in mammals are methylation and hydroxymethylation of DNA, either of which may be placed on the fifth carbon of the cytosine pyrimidine ring. A host of modifications including methylation, acetylation, ribosylation, phosphorylation, sumoylation (related to small ubiquitin-like modifiers), ubiquitylation and citrullination can occur at more than 30 amino acid residues of the four core histones within the nucleosome. Epigenetic modifications to the mammalian genome include methylation of cytosines in the DNA; methylation, acetylation, ribosylation, phosphorylation, sumoylation and ubiquitylation of the histones bound to the DNA; and the precise positioning of histone containing nucleosomes over the DNA.

Epigenetic alterations to the genome can influence development and health as profoundly as mutagenesis of the genome. One of the most dramatic examples is the methylation of DNA at the promoter of the p16 tumor suppressor. Such methylation silences the gene, and so do mutations to the gene sequence itself, and both events contribute to the development and progression of colorectal cancer. However, unlike mutations, epigenetic silencing of p16 can be reversed pharmacologically, and hence providing the possibility of medical intervention.

Specific changes in epigenetic state that occur genome wide appear to regulate cellular differentiation during development (Mikkelsen et al. (2007) *Nature*, 448, 553-U552). Perturbations of normal epigenetic state in mature tissues contribute to initiation and progression of cancer and other diseases (Feinberg, A. P. (2007) *Nature*, 447, 433-440). Additionally, studies have shown that epigenetic states are influenced by environmental variables including diet (Waterland and Jirtle (2003) *Molecular And Cellular Biology*, 23, 5293-5300), environmental toxins (Anway et al. (2005) *Science*, 308, 1466-1469) and maternal behaviors (Weaver et al. (2004) *Nature Neuroscience*, 7, 847-854). Given the fundamental role that epigenetic mechanisms play in normal development, environmental responses and how their perturbation affects disease state, there is increasing effort devoted to characterizing the human epigenome (Bernstein et al. (2007) *Cell*, 128, 669-681).

These epigenetic modifications do not alter the primary DNA sequence, but they have a potent influence on how those underlying DNA sequences are expressed. As a result, changes in epigenetic state can alter phenotypes as powerfully as alterations in DNA sequence. Also like DNA sequence states, epigenetic states can be passed from mother to daughter cells during mitosis, and can even persist through meiosis to be transmitted from one generation to the next. Although epigenetic marks can change and revert to their original state far more readily than changes in DNA sequence, they are as fundamental to development and disease as the nature of the DNA sequences on which they reside.

Abundant evidence has demonstrated the importance of epigenetic regulation to human disease—notably cancer. Early observations linked perturbations in DNA methylation to the development of human colorectal cancer and subsequent studies showed that experimental manipulation of DNA methylation state, pharmacologically or genetically, altered tumor development. These have motivated studies that correlate epigenomic profiling of tumor specimens with disease state and clinical outcomes of the individuals providing the specimens. Importantly, ongoing clinical trials using drugs that modify epigenetic states have shown therapeutic promise and the ability to attenuate epigenetic biomarkers that indicate poor prognoses. Although changes in DNA methylation during cancer development and progression have attracted considerable attention, DNA methylation states are also influenced by alterations in histone modification state and nucleosome positioning. The reciprocal interactions among all these epigenetic marks are all likely to be of importance to cancer development and progression, In addition to controlling processes fundamental to cancer, epigenetic states influence responses of mammals to changes in their environment. Maternal behavior during nursing, exposure to endocrine disruptors and the nutrient composition of diets each have been shown to elicit specific phenotypes that correlate with specific changes in epigenetic states. Most importantly, these phenotypes, and the accompanying epigenetic alterations, can be transmitted from parent to offspring, even if only the parents and not the offspring experienced the environmental insult. This raises the possibility that some complex traits that run in families, like obesity, cancer or behavioral patterns, are transmitted by epigenetic means and result from environmental exposures experienced during prior generations.

A common theme in biology is that mechanisms influencing disease states like cancer, or homeostatic responses to environment are also fundamental to development. Epigenetic mechanisms have been shown to be critical to *Drosophila* development and mammalian development.

Existing approaches for analyzing epigenetic modifications of chromatin, such as chromatin immunoprecipitation (ChIP), can evaluate only one epigenetic mark at a time and are labor-intensive, serial processes that impose significant limitations on analysis throughput and sample quantity. The ChIP technique involves immunoprecipitation using an antibody specific to one epigenetic modification of interest to isolate modified chromatin, which is subsequently analyzed using massively parallel DNA sequencing, microarray hybridization or gene-specific PCR. This method can be used to characterize the genome placement of a chromatin associated protein and is the predominant analytical tool currently practiced in epigenomic and chromatin research. However, it suffers from two major limitations. First, the analysis requires $10^4$ to $10^7$ cells and is incapable of assessing epigenetic changes in vanishing quantities, making studies of developing embryos, sorted cells or microdissected cells impossible. Second, only one epigenetic mark can be isolated at a time, making detection of co-existent marks very difficult. Measurements provide only information about the 'average' chromatin state in a cell population and nothing about the individual DNA strands. In one published example involving the characterization of bivalent states in ES cells, these limitations introduced ambiguity as to if tri-methylated histone H3 lysine 27 (H3K27me3) and tri-methylated histone H3 lysine 4 (H3K4me3) marks were present simultaneously on a given gene or if two populations existed with the ES culture, each with a mutually exclusive mark. Sequential ChIPs against two different antibodies may circumvent this limitation, however this solution is impractical for whole genome analysis.

As such, current methods for epigenomic testing involve bulk molecule analysis. The results are representative of a composite signal from multiple copies of a genetic material, which is distinct from single molecule analysis. Histone modifications are most commonly detected using chromatin immunoprecipitation (ChIP), in which modification-specific antibodies are used to immunoprecipitate the associated DNA, which is then detected by hybridization to microarray (Ren et al. (2000) *Science*, 290, 2306-2309) (ChIP-chip) or deep sequencing (Barski et al. (2007) *Cell*, 129, 823-837) (ChIP-seq). DNA methylation can also be detected by immunoprecipitation using a methylcytosine antibody (Weber et al. (2005) *Nature Genetics*, 37, 853-862), or with bisulfate sequencing, which offers more comprehensive analysis of DNA methylation states (Zhang et al. (2006) *Cell*, 126, 1189-1201). Genome wide epigenomic analyses using antibodies often use on the order of $10^6$ to $10^7$ cells. ChIP has been used with as few as 100 cells, however, with this few cells the analysis was locus specific and not genome wide (O'Neill et al. (2006) *Nature Genetics*, 38, 835-841). A far more significant limitation is encountered when studies seek to determine whether or not two or more epigenetic marks are coincident within the genome or are present on a single piece of genetic material, e.g., a single chromatin. Analysis of each epigenetic mark requires an independent immunoprecipitation. When precipitating chromatin from an ensemble of cells with different antibodies, it is difficult to distinguish true coincidence of the detected marks from the existence of multiple populations within the ensemble, each with a different epigenomic profile. This can be somewhat overcome with sequential ChIP, where the material precipitated by one antibody is re-ChIPed with a second antibody (Bernstein et al. (2006) *Cell,* 125, 315-326). However, these techniques are not amenable to genome wide analysis or for studies in which more than two epigenetic marks are investigated. Furthermore, bulk analysis techniques report an average of the population and do not consider variations at the single molecule level. Thus, there remains a considerable need for alternative methods and compositions that provide for a more robust genome-wide epigenetic analysis. The present invention satisfies this need and provides related advantages.

SUMMARY OF THE INVENTION

In some embodiments, the present invention provides for assessing epigenetic variations at a single chromatin level. Single-molecule analysis provides several advantages over conventional approaches. First, the analysis provides information on individual molecules whose properties are hidden in the statistically averaged information that is recorded by ordinary ensemble measurement techniques. In addition, because the analysis can be multiplexed, it is conducive to high-throughput implementation, requires smaller amounts of reagent(s), and takes advantage of the high bandwidth of detection systems such as modern avalanche photodiodes for extremely rapid data collection. Moreover, because single-molecule counting automatically generates a degree of immunity to illumination and light collection fluctuations, single-molecule analysis can provide greater accuracy in measuring quantities of material than bulk techniques. As such, single-molecule analysis greatly improves the efficiency and accuracy in epigenetic analysis, genotyping, gene expression profiling, DNA sequencing, nucleotide polymorphism detection, pathogen detection, protein expression profiling, and drug screening. Therefore, there is a considerable need to overcome these disadvantages of bulk analysis techniques. Accordingly, the present invention provides devices and methods that should overcome the limitations of the prior art and transform how epigenetic and chromatin research is performed.

The present invention provides for methods for performing epigenetic analysis of a genetic material in a channel, comprising: (a) flowing the genetic material through said channel, wherein said genetic material is labeled with a plurality of labels, at least one of which is specifically complexed with an epigenetic marker on said genetic material, and at least one other label is complexed with a protein and/or nucleotide of said genetic material; (b) illuminating the channel to create a plurality of interrogation volumes, each of which is confined by walls of said channel and a beam of light; and (c) detecting the at least one label and the one other label from the same or distinct interrogation volumes of said plurality to generate time-correlated resolution of said at least one and said at least one other label, thereby performing said epigenetic analysis.

Another aspect of the invention provides for methods for performing epigenetic analysis of a genetic material in a channel, comprising: (a) flowing the genetic material through an illuminated interrogation volume, said interrogation volume being confined by walls of said channel and a beam of light, wherein said genetic material is labeled with a plurality of labels, at least one of which is specifically complexed with an epigenetic marker on said genetic material, and at least one other label is complexed with a protein and/or nucleotide of said genetic material; and (b) simultaneously detecting the at least one label and the at least one other label within the interrogation volume, thereby performing said epigenetic analysis.

A further aspect of the invention provides for methods for obtaining real-time analysis data regarding a material in a channel, comprising: (a) flowing the material through an illuminated interrogation volume, said interrogation volume being confined by walls of said channel and a beam of light, wherein said material is labeled with a plurality of labels, at least one of which is specifically complexed with a marker on said material, and at least one other label is complexed with said material; (b) detecting the at least one label and the at least one other label within the interrogation volume in real-time, thereby producing said real-time analysis data; and (c) displaying said real-time analysis data on a display device, wherein said real-time analysis data reflects information on said at least one label and said at least one other label.

One aspect of the invention provides for a system for characterizing a single nucleic acid molecule, comprising: (a) a channel configured to hold said molecule; (b) one or more light sources configured to illuminate the channel to create one or more interrogation volumes; (c) a detection system configured to detect at least two types of signals indicative of two distinct properties of said nucleic acid molecule from the one or more interrogation volumes; and (d) a processor programmed to provide real-time time-correlated resolution of the at least two types of signals from said one or more interrogation volumes, thereby characterizing said single nucleic acid molecule.

In a further aspect of any of the foregoing systems and methods, the two types of signals are detected simultaneously or the detection system detects four types of signals. In a further aspect of any of the foregoing systems and methods, the processor is characterized in that: (i) it is programmed to provide time-correlating resolution of the at least two types of signals from more than one interrogation volume; or (ii) comprises a field-programmable gate array programmed to provide real-time time-correlated resolution of the at least two types of signals.

Another aspect of the invention provides for a system for characterizing an object, comprising: (a) a channel configured to hold said object; (b) one or more light sources configured to illuminate the channel to create one or more interrogation volumes; (c) a detection system configured to detect at least two types of signals indicative of two distinct properties of said object from the one or more interrogation volumes; (d) a processor programmed to provide real-time time-correlated resolution of the at least two types of signals from said one or more interrogation volumes, thereby characterizing said object; and (e) a user interface configured to receive data from the processor and display the data, wherein the data comprises information on the at least two types of signals from said one or more interrogation volumes.

The present invention provides for methods comprising the steps of a) providing a sample comprising DNA fragments or chromatin, wherein the chromatin comprises fragments of DNA; b) labeling said DNA fragments or chromatin with one or more labels specific for DNA; c) labeling said DNA fragments or chromatin with one or more labels specific for one or more epigenetic markers; d) contacting the labeled sample with a microfluidic device comprising a submicrometer channel; e) applying a voltage potential or pressure differential across the submicrometer channel, wherein the voltage potential or pressure differential is sufficient to flow said DNA fragments or chromatin through the submicrometer channel; f) detecting DNA by detecting the one or more labels specific for DNA; and g) detecting epigenetic markers by detecting the one or more labels specific for one or more epigenetic markers; wherein the detection is performed with single molecule resolution.

The present invention provides methods comprising contacting a device comprising a submicrometer channel comprising a detection volume and a first end and at least a second end with a reaction mixture comprising (a) a plurality of chromatin fragments comprising DNA and one or more epigenetic modifications; (b) a label specific for DNA; and (c) a label specific for the one or more epigenetic modifications; wherein the submicrometer channel is of a size that essentially one chromatin fragment is disposed within the detection volume at a time.

In one embodiment, the invention provides for methods of flowing a DNA sample in a solution confined within a nanofluidic channel, illuminating the sample with a Gaussian shaped laser profile, and detecting fluorescence events indicative of histone or DNA components. The sample may be illuminated with two Gaussian shaped laser profiles. In some embodiments, the light source for illuminating the sample is an LED or a VCSEL.

A further aspect of the invention provides for time coincident detection of (a) one or more labels specific for DNA; and (b) one or more labels specific for one or more epigenetic modifications.

In any of the foregoing aspects and embodiments, the genetic material is a chromatin, a nucleic acid molecule, or a single nucleic acid molecule. The material to be analyzed and/or sorted can be a chromatin, a nucleic acid molecule, or a single nucleic acid molecule.

In any of the foregoing aspects and embodiments, the material can be analyzed with single molecule resolution. In some embodiments, the detecting step provides a time-dependent resolution of better than about 10 microseconds. The subject methods can further comprise detecting time coincident detection of one or more labels specific for DNA and one or more labels specific for one or more epigenetic markers. The one or more epigenetic markers can be selected from one or more methylated DNA nucleotides, one or more hydroxymethylated DNA nucleotides, one or more acetylated histones, one or more methylated histones, one or more ubiquinated histones, one or more sumoylated histones, one or more phosphorylated histones, methyl DNA binding protein (MDB1), RNA polymerase II, and SWI/SNF.

In any of the foregoing aspects and embodiments, the one or more methylated DNA nucleotides can comprise 5-methylcytosine. The one or more acetylated histones can comprise acetylated histone H3 K4, acetylated histone H3 K9, acetylated histone H3 K14, acetylated histone H3 K18, or acetylated histone H3 K23. The one or more acetylated histones can comprise acetylated histone H4 K5, acetylated histone H4 K8, acetylated histone H4 K12, or acetylated histone H4 K16. The one or more methylated histones may comprise mono, di, or tri methylated histone H3 K4; mono, di, or tri methylated histone H3 K9; mono, di, or tri methylated histone H3 K27; or mono, di, or tri methylated histone H3 K36. The one or more methylated histones may comprise mono, di, or tri methylated histone H4 K20. The one or more methylated histones may comprise mono or di methylated histone H3 R2; mono or di methylated histone H3 R17; mono or di methylated histone H3 R26; mono or di methylated histone H3 R128; mono or di methylated histone H3 R129; mono or di methylated histone H3 R131; or mono or di methylated histone H3 R134. The one or more methylated histones may comprise mono or di methylated histone H4 R3.

In some cases the epigenetic modifications are selected from the group consisting of methylated DNA nucleotides (e.g. 5-methylcytosine), hydroxymethylated DNA nucleotides, acetylated histones (e.g. H3 K4, H3 K9, H3 K14, H4 K12, H3 K18, H3 K23, H4 K5, H4 K8, H4 K12, H4 K16), methylated histones (e.g. mono di or tri methylated H3 K4, H3 K9, H3 K27, H3 K36, H4 K20, H3 R2, H3 R17, H3 R26, H3 R128, H3 R129, H3 R131, H3 R134, H4 R3), ubiquinated histones, sumoylated histones, phosphorylated histones, the presence of methyl DNA binding protein, the presence of SWI/SNF, and the presence of RNA polymerase II.

In a further aspect of any one of the foregoing embodiments, the present invention provides identifying the time coincident detection of (a) one or more labels specific for DNA; and (b) one or more labels specific for one or more epigenetic modifications as indicating epigenetically modified DNA or chromatin.

In a further aspect of any one of the foregoing aspects and embodiments, the methods may further comprise determining whether a time coincident or time-correlated detection of the label specific for DNA and the label specific for the one or more epigenetic modifications has occurred. In some embodiments, the methods provided herein may further comprise identifying the time coincident detection of the one or more labels specific for DNA and the one or more labels specific for one or more epigenetic markers as indicating epigenetically modified DNA. The methods may further comprise identifying the time coincident detection of the label specific for DNA and the label specific for the one or more epigenetic modifications as the detection of an epigenetically modified chromatin fragment. The methods may further comprise counting the number of epigenetically modified chromatin fragments detected.

In a further aspect of any of the foregoing aspects and embodiments, the methods may comprise detecting at least three or four labels.

In a further aspect of any of the foregoing aspects and embodiments, the methods can comprise detecting one label that is specifically complexed with an epigenetic marker and at least one other label. The at least one other label can be complexed with a histone or is a nucleic acid binding agent selected from the group consisting of sequence specific probe, intercalating dye, minor groove binder, and DNA binding proteins. The at least one other label is complexed with a binding agent that complexes with a target selected from the group consisting of a non-histone protein, a transcription factor, MBD1, RNA Pol II, and RNA.

In any of the foregoing aspects and embodiments, the interrogation volume(s) is/are less than about 10, 1, 0.5, 0.2, 0.1, or 0.05 femtoliters. The genetic material can be characterized in less than about 1, 0.5, 0.1, 0.01, 0.001, or 0.0001 seconds. The illuminated interrogation volume(s) can contain a single chromatin. The one or more interrogation volumes can be one or more of (a) less than about 10, 1, 0.5, 0.2, 0.1, or 0.05 femtoliters, (b) no greater than about 10,000 times of the size of the object, provide single molecule resolution, (c) dimensioned to hold a single nucleic acid molecule, and (d) confined by the walls of the channel and a beam of light from said light sources, said beam of light having a diameter no greater than X microns.

In any of the foregoing embodiments, the detection system can measure a signal to noise ratio of greater than about 2. The channel comprises an optically transparent wall. The light sources provide a plurality of light beams of a varying wavelength.

In a further aspect of any one of the foregoing embodiments, the present invention provides for excitation of the label specific for the one or more epigenetic modifications and excitation of the label specific for DNA with an illumination source such as an incandescent source, a light emitting diode, a flash lamp, or a laser. The illumination source may be one or more lasers. In a further aspect of any one of the foregoing embodiments, the present invention provides for detecting emitted photons with a photodetector such as a photomultiplier tube, an avalanche photodiode, a CCD, or CMOS array.

The emission may comprise detecting emitted photons with an avalanche photodiode or a photomultiplier tube.

The methods may further comprise counting the amount of epigenetically modified DNA. The methods may further comprise storing the results of said counting the amount of epigenetically modified DNA on a computer readable medium.

The methods may further comprise storing the number of epigenetically modified chromatin fragments detected on a computer readable medium.

The methods may further comprise varying the amount of the applied voltage across the submicrometer channel to sort epigenetically modified DNA from DNA that does not provide time coincident detection of one or more labels specific for DNA and one or more labels specific for one or more epigenetic markers. The methods may further comprise varying the amount of the applied pressure across the submicrometer channel to sort epigenetically modified DNA from DNA that does not provide time coincident detection of one or more labels specific for DNA and one or more labels specific for one or more epigenetic markers. The methods may further comprise applying a sorting laser to sort epigenetically modified DNA from DNA that does not provide time coincident detection of one or more labels specific for DNA and one or more labels specific for one or more epigenetic markers. The subject methods may further comprise varying a magnetic moment across the submicrometer channel to sort epigenetically modified DNA from DNA that does not provide time coincident detection of one or more labels specific for DNA and one or more labels specific for one or more epigentic markers.

In any of the foregoing embodiments, the sorted epigenetically modified DNA can be further analyzed by PCR, nucleic acid hybridization analysis, microarray analysis, ChIP, or DNA sequencing. In any of the foregoing embodiments, the methods may further comprise calculating the size of the detected DNA from a signal magnitude provided by the detecting of the one or more labels specific for DNA. In a further aspect of any one of the foregoing embodiments, the present invention provides a method for sorting the epigenetically modified DNA or chromatin by varying the voltage, using a sorting laser, varying the magnetic moment, or varying the pressure differential across the submicrometer channel. In a further aspect of any one of the foregoing embodiments, the present invention provides for further analyzing sorted DNA by PCR, nucleic acid hybridization, microarray, ChIP, DNA sequencing, mass spectrometry, and NMR. In a further aspect of any one of the foregoing embodiments, the present invention provides for calculating the size of the DNA from a signal magnitude provided by detecting of the one or more labels specific for DNA.

The methods may comprise varying the amount of the applied voltage or pressure across the submicrometer channel to sort epigenetically modified DNA from DNA that does not provide time coincident detection of one or more labels specific for DNA and one or more labels specific for one or more epigenetic modifications.

The methods may further comprise using a sorting laser to sort the epigenetically modified DNA from DNA that does not provide time coincident detection of one or more labels specific for DNA and one or more labels specific for one or more epigenetic modifications. In some embodiments, the sorted epigenetically modified DNA can be further analyzed by PCR, nucleic acid hybridization analysis, microarray analysis, ChIP, or DNA sequencing. The one or more epigenetic modifications can be selected from methylation of one or more DNA nucleotides, hydroxymethylation of one or more DNA nucleotides, acetylation of one or more histones, methylation of one or more histones, ubiquination of one or more histones, sumoylation of one or more histones, phosphorylation of one or more histones, binding of RNA polymerase II, and binding of SWI/SNF.

The methods may further comprise applying a voltage potential or pressure differential across the submicrometer channel, wherein the voltage potential or pressure differential propels the plurality of chromatin fragments from the first end of the submicrometer channel to another end of the submicrometer channel. The method may further comprise detecting the label specific for DNA. The method may further comprise detecting the label specific for the one or more epigenetic modifications.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A is a photograph of a 100 millimeter diameter wafer containing 27 devices, each consisting of a parallel array of 16 submicrometer fluidic channels for single molecule spectroscopy. Fluidic ports are added (left side of wafer) to interface with fluid reservoirs leading to channels. The device can be used to collect single molecule time coincident data, in which a voltage gradient can be set up to run chromatin from bottom to top or from top to bottom. FIG. 1B depicts an optical micrograph of 15 of the 16 fluidic channels present on one of the 27 devices. FIG. 1C depicts a magnified view of one of the fluidic channels. The view is a differential interference contrast optical micrograph of a typical nanofluidic channel used in SCAN (single-chromatin analysis at the nanoscale). The narrow region, with a 500 nm wide and 250 nm deep cross-section, was used during fluorescence detection. 432 of these channels were assembled on a single 100 mm diameter fused silica wafer. The scale bar is 10 μm.

FIG. 4A illustrates a micrograph showing snapshot of fluorescently-labeled DNA resting inside fluid channels. FIG. 4B illustrates a micrograph (with time lapse) showing the same fluorescently labeled DNA during flow and single molecule isolation (constricted region).

FIG. 5A depicts a photon burst histogram for lambda phage DNA that has been digested with HindIII. The positions of the peaks depend on the length of DNA fragments; the peak area is proportional to the relative concentration of each fragment. FIG. 5B depicts a plot of the burst size as a function of the known fragment size. The dashed line is a linear least-square fit indicating the ability to accurately determine the size of various DNA fragments.

FIG. 6A depicts the number of photons detected in separate spectral channels as a function of time when quantum dots (bottom) bound to organic Alexa Fluor 488 (AF488 top) molecules are electrokinetically flowed through a microfluidic channel FIG. 6B depicts a small expanded time interval in order to see three instances of coincident detection where the quantum dot and AF488 label pass through the focal volume at the same time.

FIG. 7A shows Photon burst scans reveal the Y-shaped nucleic acid engineered (NAE) structure for a 3R1G (3 Red (dark circles), 1 Green (light circle) fluorophore) label. Shaded bands indicate time coincident detected bursts. FIG. 7B illustrates how examination of the burst intensity (height) histogram may reveal easily distinguished fluorophore content on 1G1R (1 green and 1 red fluorophore) and 4G4R (4 green and 4 red fluorophores) labels.

FIG. 13 depicts coincidence statistics from experiments using three different molar ratios of TOTO-3 to DNA, or no TOTO-3. The number of photon bursts detected in the red channel (TOTO-3-labeled DNA) and green channel (H2B-GFP-tagged nucleosomes) are reported, along with the duration of each bursts and the percentage that are coincident with bursts of the other color. Coefficients of variation are also reported, calculated from the total events for each experiment. Note that when TOTO-3 is used to label DNA at concentration ratios of 1:10 or higher, greater than 95% of the GFP-containing particles are also carrying the DNA intercalator TOTO-3. This indicates an abundance of flowing chromatin is intact on our devices. The red bursts seen in the absence of TOTO-3 are due to residual TOTO-3 dye left from prior runs on the reusable devices.

FIGS. 14A and 14B show a plot of the number of fluorescent events per minute for which TOTO-3 (FIG. 14B) and GFP (FIG. 14A) signals are coincident as a function of the proportion of H2B-GFP expressing Hela cells used to prepare chromatin. FIGS. 14C and 14D show the coincidence rates from the 5 min MNase digestions are normalized to the number of H2B-GFP fluorescent events (FIG. 14C) and TOTO-3 events (FIG. 14D). The rate of coincidence per GFP event is constant in all dilutions of GFP-tagged chromatin. The rate of coincidence per TOTO-3 event diminishes as the GFP input diminishes.

FIG. 16A shows a light micrograph of a sorting device in which 10 Kbp DNA fragment labeled with YOYO-1 is run from bottom to top, with the top two bifurcations (from one bifurcation point) representing two possible outflow tracts. FIG. 16B shows a long exposure fluorescent micrograph of YOYO-1 labeled DNA flowing through the sorting device from bottom to top. In this image, the electrode in the left arm of the outflow tract was charged, directing DNA to the left collection chamber. Note that the electrode in the right arm can be charged by a high-speed switch that is programmed to respond to observations made in the inspection volume, just below the bifurcation. The sample, which could be chromatin, could be labeled with TOTO-3 and analyzed and/or sorted similarly.

FIG. 19A: A TCH illustrates the absence of coincident two-color SMD events when analyzing chromatin from wild-type HeLa nuclei. With GFP-HeLa chromatin from the 5 minute digestion, a central Gaussian peak, corresponding to intact chromatin molecules emitting two fluorescent colors, emerged from a background of uncorrelated events. By integrating the area under the peak and subtracting the uncorrelated background, we observed more than 16,000 two-color chromatin molecules. FIG. 19B: The proportion of two-color chromatin molecules increased in direct proportion with GFP-HeLa nuclei content, as described by a linear fit with $R^2=0.98$ and $R^2=0.95$ for the 5 and 15 minute digestion assays, respectively. Error bars represent the propagated error from SMD (single molecule detection) of both the bound and unbound molecules.

(FIG. 20A) Unmethylated (top) and methylated (bottom) DNA samples labeled with TOTO-3 were both incubated with a molar excess of MBD1 probes labeled with Alexa Fluor 488 and then analyzed for 15 minutes. The emergent peak in the bottom panel demonstrates SMD of methylated DNA. The molar excess of labeled MBD1 contributed to the background of uncorrelated events within each experiment. (FIG. 20B) We analyzed mixtures of methylated and unmethylated DNA. The proportion of dual-color labeled MBD-DNA was shown to increase with methylated DNA, as described by a linear fit with $R^2=0.99$. Error bars represent the propagated error from SMD of both the bound and unbound molecules.

DETAILED DESCRIPTION OF THE INVENTION

Figure 1A:
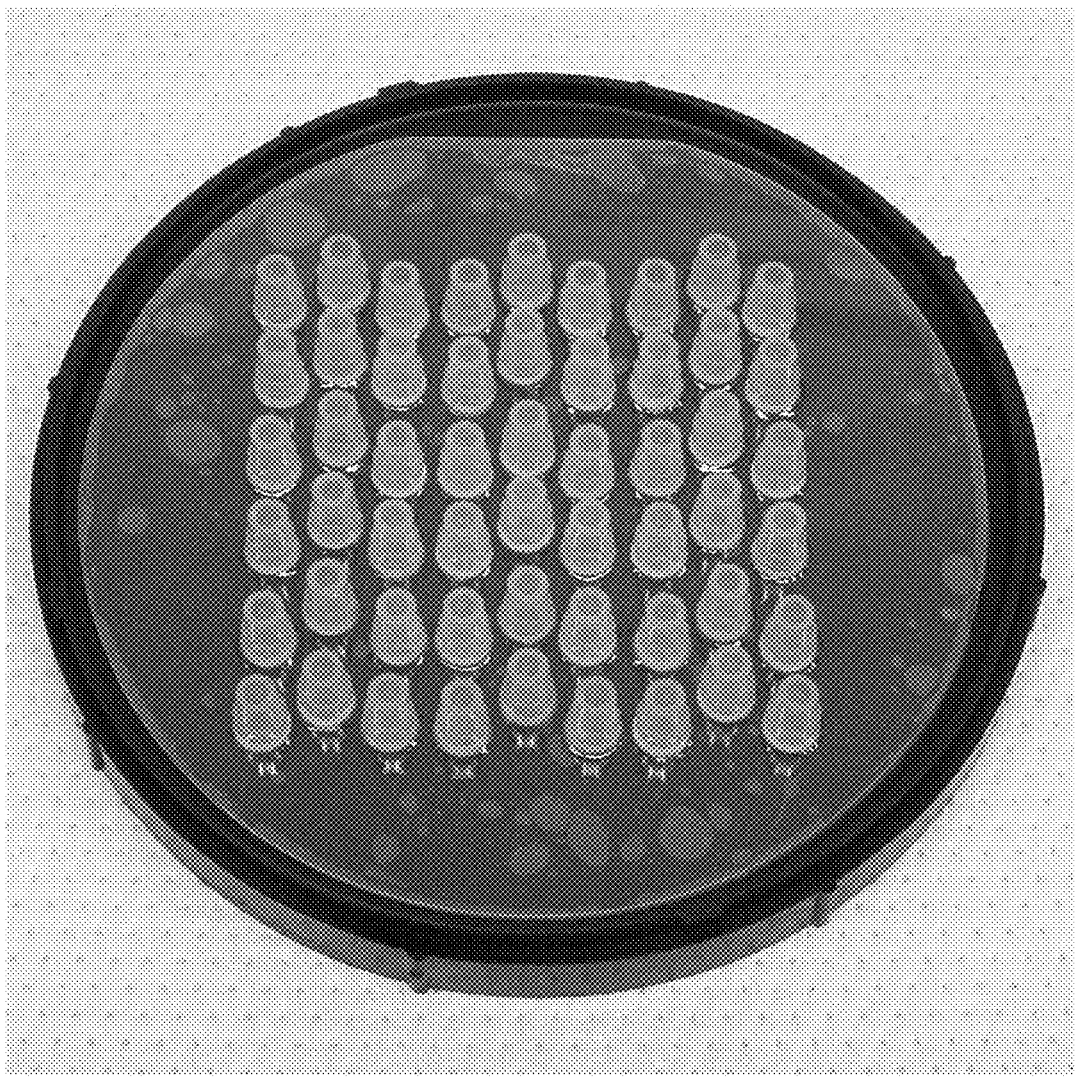
FIGS. 1A, 1B and 1C depict exemplary devices of the present invention.
Figure 1B:
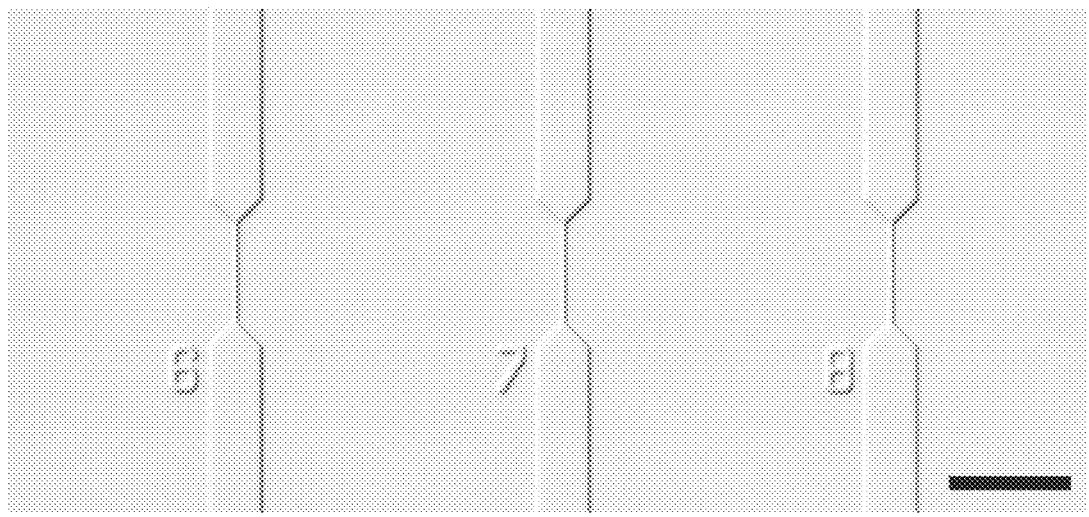

Microfluidic and nanofluidic platforms that combine high throughput detection and analysis of single chromatin fragments can overcome the limitations of existing epigenomic methods. In some embodiments, the present invention includes compositions and methods for flowing and detecting single native chromatin molecules. In some embodiments, methods for flowing and detecting single native chromatin molecules can be done by analyzing time-coincident fluorescent signatures of both the DNA and histone proteins within the chromatin at high throughput. In some embodiments, the invention includes methods to study an epigenetic mark in DNA using conditions that paralleled chromatin studies and a fluorescently labeled probe that can bind to methylated DNA. These methods can be referred to as SCAN (single-chromatin analysis at the nanoscale) and are the first demonstration of single-molecule high-throughput epigenetic analysis.

In one aspect, the present invention provides methods and devices for detection of epigenetic modifications at single molecule resolution. The methods and devices provided herein may be applied to epigenetic analysis of individual chromatin, or DNA molecules. Single molecule studies of chromatin allow simultaneous detection of multiple epigenetic marks on an individual chromatin fragment and require very small amounts of input cell material. This dramatically improves the quality of epigenetic analyses and opens up new avenues of investigation at the single-molecule level. The devices and methods provided herein can be equally well applied to the analysis of other chromatin associated factors that might not formally be considered to be epigenetic in nature. These methods can provide simultaneous detection of multiple epigenetic marks and may address fundamental questions in developmental biology and human health.

Methods

The invention provides for methods for performing epigenetic analysis of genetic material. One aspect of the invention provides for a method for performing epigenetic analysis on a genetic material in a channel, comprising (a) flowing the genetic material through said channel, wherein said genetic material is labeled with a plurality of labels, at least one of which is specifically complexed with an epigenetic marker on said genetic material, and at least one other label is complexed with a protein and/or nucleotide of said genetic material; (b) illuminating the channel to create a plurality of interrogation volumes, each of which is confined by walls of said channel and a beam of light; and (c) detecting the at least one label and the one other label from the same or distinct interrogation volumes of said plurality to generate time-correlated resolution of said first and second label, thereby performing said epigenetic analysis.

In another embodiment of the invention, the detection of the first and second label is performed simultaneously. Performing epigenetic analysis on a genetic material in a channel can comprise flowing the genetic material through an illuminated interrogation volume, said interrogation volume being confined by walls of said channel and a beam of light, wherein said genetic material is labeled with a plurality of labels, at least one of which is specifically complexed with an epigenetic marker on said genetic material, and at least one other label is complexed with a protein and/or nucleotide of said genetic material, and simultaneously detecting the first and second label within the interrogation volume, thereby performing said epigenetic analysis.

In some embodiments, a method for producing real-time analysis data on a material in a channel can comprise flowing the material through an illuminated interrogation volume, said interrogation volume being confined by walls of said channel and a beam of light, wherein said material is labeled with a plurality of labels, at least one of which is specifically complexed with a marker on said material, and at least one other label is complexed with said material, detecting the first and second label within the interrogation volume in real-time, thereby producing said real-time analysis data, and displaying said real-time analysis data on a display device, wherein said real-time analysis data comprises information on said first and second label.

The present invention can increase the sensitivity of epigenomic analysis, which can allow the use of samples comprising single cell quantities of genomic material. It can also increase the number of simultaneous epigenetic analyses possible. The present invention provides a method that allows simultaneous analysis of multiple epigenetic markers (e.g. 2, 3, 4, 5, 6, 7, 8, 9, 10, 11, 12, 13, 14, 15, 16, 17, 18, 19, 20, 21, 22, 23, 24, 25, 26, 27 or more) using extremely limiting amounts of materials, a few orders of magnitude lower than is currently needed for histone analysis. In some embodiments, the method relies on single molecule three-color fluorescence microscopy imaging of more than 4,000 DNA and chromatin fragments per minute flowing through a single electrophoretic channel on a nanofluidic device. Using this device it is possible to dramatically expand sample throughput and the number of epigenetic marks analyzed using parallel networks of fluidic channels and simultaneous optical analysis. Sorting capabilities may allow recovery of the imaged and sorted materials for massively parallel DNA sequencing.

In some embodiments, the present invention provides for full redundant coverage of whole genomes for epigenetic modifications. In some cases, the present invention provides methods and devices for 2×, 3×, 4×, 5×, 6×, 7×, 8×, 9×, 10×, or higher coverage of genome (e.g. mouse, human, vertebrate, animal, plant, fungal, archaeal, bacterial etc.) in our full analysis. In some cases, 1,000; 2,000; 3,000; 4,000; 5,000; 6,000; 10,000; 15,000; 20,000; 30,000; 50,000; 75,000; 100,000 or more DNA fragments per minute with an average target fragment size of 1,000; 2,000; 3,000; 4,000; 5,000; 6,000; 10,000; 15,000; 20,000; 30,000; 50,000; 75,000; 100,000 bp or more, provides 2× or higher genome coverage in fewer than 3 hours, 2 hours, 90 minutes, 75 minutes, 60 minutes, 45 minutes, 30 minutes, 15 minutes, 10 minutes, 5 minutes, 3 minutes, 2 minutes, 1 minute, 30 seconds, 15 seconds, 10 seconds, 5 seconds, or less. The time to analyze data may increase as the number of chromatin marks detected increases, but this does not limit the speed of data acquisition. The device architecture may be modified to allow sample sorting and recovery for sequencing. This embodiment can take advantage of real-time data analysis and control of switching circuitry. The analytical speed may depend on software design, computer speed and the specific circuitry chosen. It is worth noting that in commercial flow cytometry equipment like the BD-Biosciences FACS Aria, sort rates of 30,000 events per second are routine. The devices of the present invention can be capable of comparable or even faster sorting rates. For examples, the devices of the invention can be capable of sorting about or more than about 30,000, 35,000, 40,000, 45,000, 50,000, 55,000, 60,000, 70,000, 80,000, 90,000, 100,000 events per second or more. At 30,000 imaging events per second of 20,000 bp fragments, the entire mammalian genome can be analyzed in 5 seconds.

In some embodiments of the invention, the genetic material can be characterized in less than about 1, 0.5, 0.1, 0.01, 0.001, or 0.0001 seconds. The characterization can be performed by a processor that receives signal corresponding to properties of the genetic material from a detection module. In one embodiment, the detection module is an avalanche photodiode. The detection module can transmit signal corresponding to more than one or a single property or marker. The detection module can transmit signal corresponding to more than two properties or markers. The processor can determine the presence or absence of an epigenetic marker based on said signal.

The invention also provides for methods for performing analytical techniques that are analogous to precipitation assays in a single-molecule format. For example, any immunoprecipitation assay can be improved using the methods, systems, and devices of the invention to obtain single-molecule resolution and/or effect high-speed characterization of a molecule or object.

Sample

The methods and devices of the present invention may be suitable for the analysis of samples comprising an object, a genetic material, a nucleic acid (e.g., DNA, RNA, or any hybrid thereof), a peptide, a protein, an aptamers, any fragment thereof, or any combination thereof. Any of these objects may be single objects, e.g., a single nucleic acid or a single chromatin.

The term "objects" can refer to any molecule, single molecule, complex, cell, cellular component, or bead described herein. For example, the systems, devices, and methods may be used to sort and/or analyze biomolecules including but not limited to genetic material, nucleic acids (e.g. DNA, RNA, and hybrids thereof), nucleic acid fragments, proteins, protein fragments, aptamers, carbohydrates, lipids, nucleic acid-protein complexes, protein-protein complexes, and any combination thereof. The object can also be a cell, cellular component, or cell fragment. For example, the systems, devices, and methods may be used to sort and/or analyze other molecules, including polymers, organic molecules, small organic molecules, drugs, drug targets, and compounds. The subject device may also sort and/or analyze particles, such as beads, vesicles, and lipid vesicles. In some cases, the systems, devices, and methods provided herein may be utilized to sort and/or analyze nucleic acids that have specific bound proteins or altered chemical states for epigenetic analysis. In some cases, the invention provides for sorting and/or analysis of chromatin, which encompasses whole chromatin and chromatin fragments, and/or histones. The object to be sorted and/or analyze can be of a variety of sizes. For example, the object to be sorted typically has a dimension that is less than the size, diameter, or width of a channel in the sorting system. In some embodiments, all dimensions of the object are less than the width and height of the channel. In other embodiments, the length of the object may be greater than the width of the channel, e.g., an elongated nucleic acid. As described herein, the objects to be sorted can be measured for intrinsic properties, or may be labeled with another molecule that complexes with the object. Examples of such labels include fluorescent dyes, e.g., a quantum dot that is optionally conjugated to a nucleic acid probe. Other labels that can be utilized include intercalating dyes, e.g., YOYO-1, TOTO-3, Syber Green, and ethidium bromide.

The genetic material can be a single molecule, or a complex formed by individual molecules. In some embodiments, the genetic material is a chromatin (encompassing chromatin fragments) or a single chromatin (encompassing single chromatin fragments). The chromatin can be analyzed for the presence or absence of an epigenetic marker, or a number of epigenetic markers present on the chromatin.

The sample may be obtained from any cell or tissue source. In some cases, the methods and devices of the present invention may be suitable for analysis of samples comprising a small or limiting amount of DNA including but not limited to: MEF DNA, ES DNA, Dnmt1−/− ES DNA, Mouse blastocyst DNA, DNA from a microdissected tumor, DNA from a pre-implantation embryo, MEF chromatin, ES chromatin, Dnmt1-/- chromatin, and blastocyst chromatin.

The object, genetic material, nucleic acid, DNA, chromatin peptide, protein, or any combination thereof may be fragmented by any means known in the art prior to (or after) flowing it into a channel, and different approaches may be preferred depending upon the source of the DNA or genetic material. For abundant and concentrated sources totaling several micrograms in 200 µl or a larger volume, a standard sonicator probe may be inserted into the tube containing the DNA. An alternative is to use DNAseI to fragment DNA. Another alternative is to use micrococcal nuclease or any other suitable nuclease such as a double stranded DNA exo or endo nuclease to fragment chromatin.

The methods provided herein are useful for analyzing methylation states in DNA or other genetic materials taken from extremely low abundance sources. A single mammalian cell can hold approximately 3 pg of genomic DNA and one use of the present invention can be to analyze DNA from approximately 30 laser microdissected tumor cells, single mouse morulae that contain eight cells and blastocysts that contain approximately 40 cells.

When working with small quantities of cells or any other samples described herein, purification methods that use proteinase treatment and organic extractions followed by alcohol precipitation can be quite reliable, and in some cases they require glycogen or tRNA as a carrier to maximize DNA recovery. An alternate approach for solubilizing DNA is to disrupt the cells physically, by placing a tube containing them in a cup horn sonicator. Sonication of microdissected cells and embryos may free DNA from nuclei, avoid sample loss during purification and make it unnecessary to use carriers. These crude extracts may be compatible, under the proper buffer conditions, with nanoscale flow and antibody detection. Sonication may produce debris that may clog the nanoscale channels of a device of the present invention, unless debris is below the cross sectional channel dimensions in the device, which may measure, e.g. approximately 500 nm×500 nm. Centrifugation may be sufficient to remove particles. Alternatively devices in which a grid, whose spacing is smaller than the channel opening, precedes the input channel may be prepared—this may prevent channel clogging by filtering particulates on the device before analysis. Also, with sonicated materials, small amounts of EDTA and SDS may be needed to preserve DNA integrity and solubilize cellular materials. When sonicating pre-implantation embryos, it may be necessary to remove the zona pellucidae using acid Tyrode's solution. The zona pellucida is a tough proteoglycan layer that may resist sonication.

The genetic material that can be analyzed by the subject method can include pre-implantation embryos. For pre-implantation mouse embryos, the zona pellucida may be removed using acid Tyrode's solution before cross-linking chromatin with formaldehyde. The proteoglycan rich zona might interfere with formaldehyde access to the nucleus. Sonication may be performed using a cup horn sonicator containing a tube holding a single embryo. Specific epigenetic marks may be detected, one at a time or in combination.

Laser microdissected materials may also be analyzed by the methods and devices of the present invention. Analysis of chromatin in microdissected samples may be performed using frozen sections. By using sections from frozen tissues, the cross-linking time may be controlled the cell-to-cell differences in exposure to formaldehyde may be limited. Paraffin embedded samples may also be analyzed.

Both native chromatin as well as preserved chromatin prepared by cross-linking proteins to DNA using formaldehyde can be used in the subject analysis. Cross-linking has the advantage of fixing and stabilizing proteins at their points of contact on the DNA, and has been widely used in ChIP, ChIP-Chip and ChIP-Seq studies. Where deemed, cross-linked chromatin from ES and MEF cells can be used. The chromatin may be stained with QD-labeled antibodies recognizing different epigenetic marks including DNA methylation, DNA hydroxymethylation, bound RNA pol II, modified or unmodified histones, or any other known epigenetic mark, then individual molecules may be imaged in a nanoscale flow channel of the present invention during voltage-directed flow. By combining different antibodies, each labeled with a different QD whose spectral properties are distinguishable, and the coincidence, or mutual exclusion, of each feature may be studied. Multiple independent features may be analyzed simultaneously (e.g. 1, 2, 3, 4, 5, 6, 7, 8, 9, 10, 11, 12, 14, 15, 16, 18, 20, 25, 30 or more).

Input materials, including genetic materials, DNAs, chromatins, or any other sample to be analyzed may be prepared by any number of methods known in the art such as using proteinase K treatment, phenol/chloroform extraction and ethanol precipitation. Similarly, chromatin may be prepared by any number of methods known in the art including native or non-native extraction methods. An important variable that may influence how many kilobases of sequence to be analyzed per unit time is the average length of the DNA fragments analyzed. The magnitude of photon bursts from YOYO-1-labeled DNA fragments from 600 bp to 27,000 bp can be readily analyzed and sized. Accordingly a wide range of fragment sizes can be used. By using large fragments, total genome analysis may be provided by querying fewer fragments and photon burst events. However, using large fragments provides a limited ability to resolve where the DNA methylation is located. In some cases, comprehensive bisulfite based analysis of DNA fragments preliminarily sorted on the basis of anti 5-methylcytidine antibody binding may be performed by the methods of the present invention.

In some cases, the methods of the present invention utilize chromatin that has already been subjected to a ChIP procedure to enrich the input material carrying the marks of interest. For example, a ChIP may be performed with anti-H3K4me3 and this material may be used in a nanoscale device of the present invention to detect H3K27me3. This enriched input material can then be used to optimize buffer conditions for epigenetic mark detection on the device. It is worth noting that with extremely high surface area to volume ratios present in the nanoscale channel, buffer conditions are critical to minimize surface-driven artifacts as well as to ensure proper antibody to antigen interactions.

Labels

The object or genetic material in the sample can be complexed, pretreated, or mixed with one or more labels. In one embodiment, the genetic material is labeled with a plurality of labels, at least one of which is specifically complexed with an epigenetic marker on said genetic material and at least one other label that is complexed with a protein and/or nucleotide of said genetic material. Labels include fluorescent dyes, quantum dots, magnetic particles, metallic particles, and colored dyes. Examples of dyes are described herein. The dyes or labels can be conjugated to binding moieties such as antibodies, nucleic acids, proteins, aptamers, affinity clamps, peptides, naturally occurring proteins and protein domains that bind to target proteins of interest. The binding moieties can be specific or generic. In some embodiments, one binding moiety is specific to an epigenetic marker and a second binding moiety generically binds to nucleic acids, proteins, or biological molecules.

The genetic materials to be analyzed can be analyzed with or without a label. In some embodiments, the genetic material is not labeled and detection techniques not reliant on labels can be used to characterize the genetic material. For example, electrical conductance and UV absorbance can detect DNA in the absence of a label. In other embodiments, the genetic material to be analyzed is labeled such that properties of the genetic material can be observed. Labels can be specific to certain trains of the genetic material, or the labels can be generic. Generic labels include labels that bind non-specifically to nucleic acids (e.g., intercalating dyes, nucleic acid groove binding dyes, and minor groove binders) or proteins. Examples of intercalating dyes include YOYO-1, TOTO-3, Syber Green, and ethidium bromide. In some cases, the method provides alternative approaches to label chromatin, other than YOYO-1 or TOTO-3.

Samples may be labeled with specific labels. Specific labels can include detectable moieties (e.g., dyes, metal particles, radioactive particles, and magnetic particles) that are conjugated to moieties that bind to specific genetic markers. Chromatin may be labeled using such specific labels. Chromatin isolated from embryos at different stages from fertilization to gastrulation can be labeled with a QD-labeled antibody recognizing H3K27me3, H3K4me3 and 5-methylcytidine, or any other known epigenetic marker using a different color QD for each antibody. Alternatively, any suitable labeling reagent may be used to label epigenetic modifications such as a binding agent that specifically recognizes epigenetic markers as provided herein including but not limited to labeled antibodies, antibody fragments, minibodies, affibodies, avimers, aptamers, other proteins that bind epigenetic markers or groups of markers associated with chromatin such as MDB1. Labeled binding agents used herein can complex with any target of interest described herein. Targets of interest can include MBD1, RNA Pol II, RNA, DNA, SWI/SNF, mRNA, pre-mRNA, miRNA, piRNA, lincRNA, and siRNA. Similarly, suitable labels may include but are not limited to QD, organic fluorophores, or agents that can be detected by changes in magnetic or electrical properties. Where desired, the labeled chromatin may be sorted on a device of the present invention and fractions with each combination of these marks may be isolated for subsequent high throughput (e.g. Solexa, Illumina, 454/Roche, etc.) sequencing.

Samples may be labeled with a label conjugated to a binding moiety that complexes with a target. In some embodiments, the target is a specific DNA sequence. Specific DNA sequences can be recognized using labeled binding moieties, such as labeled probes, nucleic acid sequences, and DNA binding proteins. DNA binding proteins include, but are not limited to, those described in Jamieson, Nat Rev Drug Discov 2: 361-8 (2003), Urnov, Nature 435: 646-51 (2005), Moscou, Science 326: 1501 (2009), and Nielsen *Science* 254, 1497 (1991).

In some instances, two generic dyes and one specific dye corresponding to a first property can be used to label a sample. This can allow for distinction between free dye, objects without the first property, and objects with the first property. In other embodiments, two generic dyes and two specific dyes may be used to label a sample, where the first specific dye corresponds to a first property and the second specific dye corresponds to a second property. In addition to detecting free dye, objects without a first property, and objects with a first property, this would allow for detection of objects without either the first or second property, objects with the second specific property, objects without the second property, and objects with both the first and second property.

Nucleic acid binding agents can be used to label a sample. Non-limiting examples of labels or labeling moieties include probes of a specific sequence, intercalating dyes, and minor groove binders. Generally, fluorescent intercalators can be dyes that bind to double-stranded DNA or double-stranded RNA by inserting themselves in between a neighboring base pair. Generally, minor groove-binders can be dyes that bind to the minor groove of double-stranded DNA. There are still other dyes that may bind to nucleic acids via multiple modes, including electrostatic interaction between a positively charged dye and the negatively charged nucleic acid. In some cases, it is desirable to image all chromatin fragments, regardless of their epigenetic states. For example, one may identify the proportion of sites in the blastocyst genome that carry the H3K27me3 and H3K4me3 epigenetic marks. At least two alternate approaches are available for labeling all chromatin fragments, independent of intercalating dyes. One approach is to label Alexa-coupled nucleotides to the 3' end of each chromatin fragment using terminal deoxynucleotide transferase (TdT). The Alexa fluor chosen may be spectrally distinct from the QDs chosen for the antibodies. This TdT-mediated labeling is not limited by the cross-linking and only depends on a 3'-OH group at the end of each chromatin fragment. Another approach is to label a histone rather than the DNA using antibody recognizing H1 (anti-H1) or one of the core histones. With 80% of the genomic sequences associated with nucleosomes only extremely rare chromatin fragments will remain unlabeled by anti-H1 in preparations of chromatin fragments in the 20,000 bp size range.

Samples can be labeled with QD-anti-methyl-C for detection of methylated DNA. In some cases, methylcytosines directed towards the nucleosome may be inaccessible to QD-anti-methyl-C in cross-linked chromatin. This can provide lower QD fluorescence emissions for a chromatin fragment relative to the same DNA sequence lacking cross-linked proteins. However, linker DNA between nucleosomes may be unaffected by cross linking, so linker DNA is as accessible in purified DNA as in cross linked chromatin. Second, even for DNA wrapped around nucleosomes, less than half of the signal may be lost because methylcytosines extend into the major groove of DNA so access of antibody in solution to the major groove is what determines QD-anti-methyl-C binding to methylated DNA; DNA is wrapped around the external surface of nucleosomes with less than half the major groove surface area in sufficiently close proximity to the histones to exclude the antibody; thus most of the methylcytosines in a nucleosome is accessible to QD-anti-methyl-C. The combined access of methylcytosines in nucleosome-associated DNA and linker DNA to the solution phase may provide adequate signals for sequences containing methylated DNA.

In some cases, methylated DNA in chromatin may be detected by labeling samples with QD-anti-methyl-C that can bind to methylcytosines and QD-anti-H1 or a 5' or 3' end label that can bind to chromatin. This can be used, for example, to label chromatin from cultured ES cells to analyze the chromatin for methylation. Dnmt1 mutant cells may be utilized as an excellent negative control to assess the specificity of the antibody binding to methylcytosine in the context of chromatin. In this case, chromatin can be from wild type and Dnmt1 mutant ES cells, which may be prepared, similar as to in ChIP, using the above-mentioned labels. The methylcytosines labeled using QD-anti-methyl-C and the labeled chromatin may be analyzed on the nanoscale device of the present invention. This method may identify the proportion of fragments bearing methylcytosine marks and the density of those marks in chromatin. A comparison can be made with the data obtained using purified DNA. In some cases, ES and MEF cell chromatin may be labeled using QD-anti-H3K4me3 and QD-anti-H3K27me3.

In some embodiments, three labels are mixed with the sample. In an exemplary embodiment, the genetic material can be ES and MEF chromatin. A third QD-labeled antibody may be added to the analysis to detect RNA pol II. By combining this antibody with QD-anti-H3K4me3 and QD-anti-H3K27me3, the methods provides for correlating the epigenetic mark placement with a marker for gene expression competency. In addition, the genome may be queried for coincidence of DNA methylation and H3K27me3.

In some embodiments, the sample is processed by the system without removal of free dye and/or free label. The free dye and/or free label can be characterized appropriately by the system by use of time-correlated or simultaneous detection of a plurality of properties. In other embodiments of the invention, free dye and/or free label is removed from the sample prior to sorting. The concentration of the free dye and/or free label in the sample can be about, less than about, or greater than about 0.01, 0.05, 0.1, 0.2, 0.3, 0.4, 0.5, 0.6, 0.7, 0.8, 0.9, 1, 2, 3, 4, 5, 6, 7, 9, 10, 15, 30, 50 times the concentration of the dye and/or label that is complexed with the object or genetic material.

Fluid Movement

The sample, which may contain a genetic material of interest that has been labeled with one, two, three, four, or more labels, can be loaded into a device of the invention for detection and analysis. The sample can be loaded to an input reservoir on the device. The sample can form a continuous body of liquid as it moves through the device. Fluid carrying the genetic material, or the genetic material alone can be directed through the channels using an external pressure source, an internal pressure source, electrokinetics, magnetics, or some combination thereof. The external or internal pressure source can be a pump, e.g., a peristaltic pump, syringe pump, or a pneumatic valve pump. The flow of the genetic material and/or the flow of a solution carrying the genetic material can be reversed. The reversal can be effected by reversing polarity of a voltage gradient and/or reversing a pumping action.

A sample, or a plurality of samples, can be loaded into one or a plurality of channels. For example, the sample or plurality of samples can be loaded into about, up to about, or less than about 1, 2, 5, 10, 50, 100, 500, 1000, 5,000, or 10,000 channels. The loading and/or analysis of sample can be sequential or simultaneous. The sample may be loaded into a common input reservoir or individual reservoirs. The channels can be arranged in a variety of configurations, including parallel channels, radial channels, branched channels or a combination thereof.

Flow of the chromatin or any other sample type described herein through nanofluidic devices may be induced electrokinetically using voltages applied to reservoirs of the device. The flow rate inside these devices can be controlled over a wide range with exquisite accuracy. The flow rate can be controlled to an accuracy of about, or better than about 0.00001, 0.00005, 0.0001, 0.0005, 0.001, 0.005, 0.01, 0.05, 0.1, 0.5, 1, 5, 10, 50, 100, 500, 1000, 5000, or 10,000 fL/s or µL/s. The flow rate can be about, less than about, or greater than about 0.00001, 0.00005, 0.0001, 0.0005, 0.001, 0.005, 0.01, 0.05, 0.1, 0.5, 1, 5, 10, 50, 100, 500, 1000, 5000, or 10,000 fL/s or µL/s. Molecules can be driven at rates of greater than about several hundred or thousand per second in each channel independently. This provides not only the opportunity to increase the rates of DNA and chromatin throughput, but it will allow the use of an electrical method for rapid single-molecule sorting. A Y-shaped separation chamber may be placed immediately following the detection region, the proverbial "fork in the road." In some cases, a more highly branched separation chamber may be utilized in parallel or in series to achieve a greater number of outflow tracts or collection chambers. Flow rate can be increased and directed preferentially to one branch or the other of the fork by briefly increasing the voltage bias in the corresponding part of the fork. In this way, the molecule is sorted toward the desired path for eventual recapture. This method of control is simple and can be applied to either DNA or chromatin fragments, bound to antibody-linked fluorophores, which report the epigenetic state.

In other embodiments of the invention, the flow of the object can be reversed. This can allow for more than one measurement to be taken on an object within a single interrogation volume. Alternatively, multiple interrogation volumes can be placed in a channel prior to a branch point such that multiple measurements of the same properties are performed on the object prior to a sorting or characterization event. For example, two, three, four, five, six, seven, or more interrogation volumes may be positioned upstream to a branch point, thereby allowing for a plurality of measurements of the same two, three, four, five, or more properties used to determine how to sort or characterize the object.

Illumination and Detection

In one aspect, the present invention provides methods for detecting properties of a genetic material to perform epigenetic analysis. The properties can be detected using one or more labels. The labels can be detected in one or more interrogation zones. The interrogation zones can be the same or distinct interrogation zones. In some embodiments, chromatin and/or individual molecules may be interrogated, simultaneously, for DNA methylation and histone modifications.

In some embodiments, the present invention provides methods for simultaneous or time-correlated detection of various molecular properties including, but not limited to, fluorescence, such as quantum dot fluorescence signatures. As described herein, the properties of the object can be measured using a variety of detection techniques. The detection step can measure optical, electrical, radioactive, physical (e.g., size, density, thermal conductivity, elasticity, viscosity, and strength), and/or magnetic properties. The fluorescence signatures can be observed in real-time and in fact be used as triggering events to control a sorting method as provided herein.

The detection step can include interrogating or inspecting an object within a defined volume. The defined volume can be referred to as an interrogation volume, inspection volume, or detection volume. In some embodiments, the interrogation volume is an optical volume when optical signals are detected. The detection step can include measuring one, two, three, four, five, six, or more properties or signals from the object. For example, an object may have distinct measurable properties that change depending on the state of the object. These measurable properties can be intrinsic to the object, or can conferred by one or more labels that are complexed with the object. Examples of labels that can be complexed with the object include fluorescently labeled antibodies that complex with epigenetic markers on a nucleic-acid containing chromatin.

Figure 3:
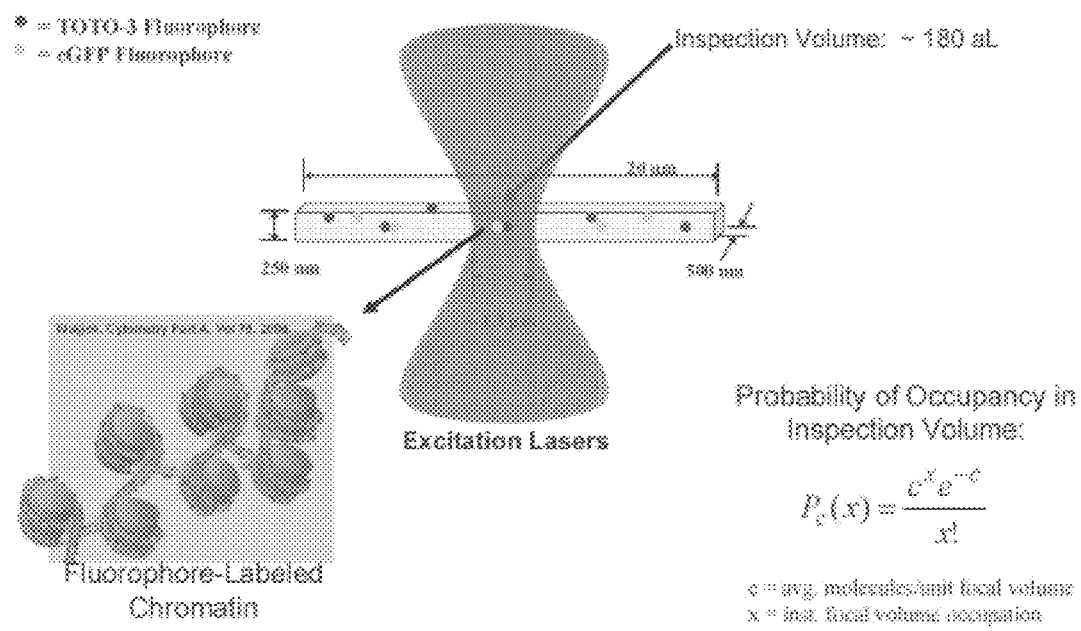
FIG. 3 illustrates a microfluidic device of the present invention comprising an inspection or detection volume suitable for single molecule detection (SMD). Depicted is a nanoscale channel and approximately 0.18 femtoliter inspection volume through which fluorescently labeled materials flow. Three classes of fluorescence emitting particles may be detected. These include DNA label bound to DNA which lacks nucleosomes comprising labeled epigenetic markers (dark circles—labeled with TOTO-3 Fluorophore), nucleosomes comprising labeled epigenetic markers that lack a DNA label (light circles, labeled with eGFP Fluorophore) and chromatin comprising nucleosomes comprising labeled epigenetic markers on labeled DNA (dark and light circle complexes). Chromatin may be loaded onto the device at a sufficiently low concentration such that the probability that two separate molecules occupy the inspection volume simultaneously is <0.005.
Figure 4A:
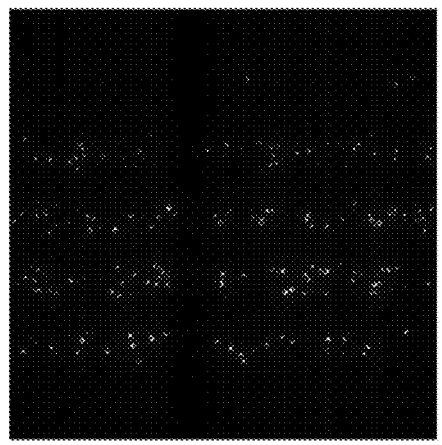
FIGS. 4A and 4B depict fluorescence optical micrographs using field illumination aid in visualizing DNA flow through parallel networks of fluid channels.
Figure 4B:
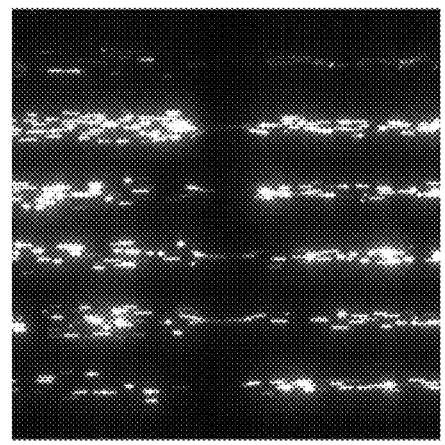

The interrogation volumes can be created by illuminating a channel with one or more light beams. The light beams can be from one, two, three, four, or more light sources. The one or more light sources can emit one or more beams of light that illuminate one or more regions or volumes within the one or more channels. The beam of light may be focused by an optical component, e.g., a high numerical aperture objective. The beams of light illuminating the channels can create one or more inspection volumes that are defined by the walls of a channel and the beams of light. The dimensions of the beam of light and the channel can define the size of the inspection volume, as shown in FIG. 3. The inspection volumes can have a volume that is about, up to about, or greater than about 0.01, 0.05, 0.1, 0.2, 0.5, 0.75, 1, 5, 10, 25, 50, 75, or 100 femtoliters.

The detection of properties of the object or genetic material can be performed in a simultaneous or time-correlated fashion. Simultaneous detection can occur by measuring two or more properties of the object at one instant in time. For example, two wavelengths of light corresponding to two distinct labels can be measured in a single interrogation volume, or overlapping interrogation volumes. Alternatively, two or more properties of the object can be measured at distinct times. This may be performed if the location of the object within the channel as it is travelling down the channel can be known, predicted, or estimated. For example, a first property can be measured at a first interrogation volume located upstream to a second interrogation volume, where a second property of the object is measured. Correlation of the signals from the first interrogation volume and the second interrogation volume can be based on the velocity of the object through the channel and the distance between the two channels. In this manner, 2, 3, 4, 5, 6, 7, 8, 9 or more properties of the object can be measured simultaneously or in a time-correlated fashion.

Signal from the one or plurality of channels can be recorded and analyzed simultaneously and/or sequentially. This can allow for the simultaneous and/or sequential detection of properties in a plurality of samples loaded simultaneously and/or sequentially to a plurality of channels. Simultaneous detection combined with the flow of sample through channels at high rates allows for thousands of molecules to be interrogated each second in each of several thousand channels.

The signals measured may have a signal-to-noise ratio of about or greater than about 1, 2, 3, 4, 5, 10, 50, 100, 200, 300, 400, 500, 1000, 5000, or 10,000. The signal-to-noise ratio can be determined based on the resolution and/or accuracy of the detector, the light source, the size of the inspection volume, the power and/or quality of the light source, the amount of light used to illuminate the inspection volume, the label used to indicate a property of the genetic material, or any combination thereof. The signal to noise ratio can be determined by the signal above the mean photon noise. A statistically significant signal can be a signal that is at least about 3 standard deviations above the mean photon noise.

Sorting

The sorting module of the present invention allows for the detection and real-time evaluation of objects and collection of the objects. Sorting can be performed as described in U.S. Provisional Application No. 61/231,979, filed Aug. 6, 2009, U.S. Provisional Application No. 61/307,827, filed Feb. 24, 2010, U.S. Provisional Application No. 61/231,963, filed Aug. 6, 2009, and U.S. Provisional Application No. 61/359,266, filed Jun. 28, 2010, and the co-pending case PCT Patent Application No. PCT/US10/44810, filed herewith, each of which is incorporated herein by reference in its entirety. The sorting of the object can be based on one, two, three, four, five, or more properties measured during detection. The properties can be measured simultaneous, or in a time-correlated fashion. A processor can be used to interpret the data collected on the object and determine a desired flow path for the object.

The sorting can allow for the detection and real-time evaluation of spectral or other single molecule signatures and the separation and collection of these specific molecules. In some embodiments, the devices and methods of the present invention provide on-the-fly evaluation of both time and spectrally coincident signatures examined within the highly confined structures of the device (fluidic channels, nanopores, or otherwise). Single molecule separation using these coincident signatures may provide salient features, such as the ability to separate specific sequences of nucleic acids bound with proteins or separate molecules in the presence of other biological species or spurious fluorescence contamination, all with an extremely low rate of false-positive detection.

One example of such an implementation is to identify rare epigenetic modifications to histone proteins bound in chromatin. The methods and devices of the present invention provide unambiguous identification of the sequences moving through the channels and provides for selection of these molecules through separation, even in the presence of other cellular debris and proteins which often accompany the chromatin strands.

In other embodiments, the present invention may provide for the recovery of sorted chromatin. This sorting and recovery may provide for determination with nucleotide sequence specificity, the regions of the genome harboring complex epigenetic profiles of interest in extremely low numbers of cells by massively parallel DNA sequencing.

In some cases, the color signatures provided by analysis of the labeled chromatin can be observed in real-time and used as triggering events to control a sorting method. Conventional sorting methods often involve valves and gates that move at the 10's of millisecond time scale or slower. In the present invention, a high-throughput counting in excess of 2,000 molecules/min has been demonstrated and this can be increased much further. Therefore, the present invention allows for a high-speed sorting method. Two high-speed methods of sorting may be used to exert control over a molecule's trajectory, one electrical and one optical. These sorting methods may be implemented in nanofluidic channels using a branched (e.g. Y-shaped) separation chamber for sorting. Additional branch points may be incorporated, either in series or in parallel, further increasing the sorting capabilities if needed.

In some embodiments of the present invention, electrical sorting is used to sort molecules based on detection of events or molecular properties. The present invention provides a device that can rapidly switch the voltage applied to a branched fluid channel to separate the molecules of interest into a collection volume. Appropriate design of the fluid system, electronic switching allows for rapidly interrogating large numbers of molecules in the sorting system.

The present invention also provides for the use of an optical technique for particle manipulation involving the use of an intense laser beam to hold or "tweeze" the particles. The intense laser can be used in the present invention for sorting molecules. Using an intense infrared laser, to minimize photodamage to the biopolymers, and high numerical aperture optics, to create a tightly confined optical potential well, a QD-chromatin conjugate may be captured. This technique may be applied inside the branched separation chamber of the present device and then the laser position may be deflected to control the particle trajectory for sorting. The optical sorting technique can be performed at a single molecule level in a nanofluidic device by utilizing the dielectric properties of the fluorophore, particle, or quantum dot. In some cases, this sorting technique may be performed using a constant applied voltage for flow of molecules in a defined direction past the laser. This sorting technique provides ultra-fast sorting—with speeds that can be limited only by fluid forces, not the sorting laser deflection. Forces in the optical potential trap are routinely on the order of 10-100 pN and, in this case, can be applied transverse to the flow direction. Flow velocities in our nanofluidics, under high-throughput conditions, nominally impart a Stokes drag force of approximately 10 pN on a 20 nm diameter particle. This indicates that deflection of the QD in the presence of flow is possible, particularly since deflection into the proper direction requires only a fraction of the possible trapping force. Various methods for high-speed laser deflection and steering are commonly used in the field of optically phased-arrays, with deflection speeds that can extend into the Megahertz range, orders of magnitude faster than the Kilohertz frequency of single molecule counting events. Our method allows for ultra-fast sorting control at rates approaching the fundamental limit inside a fluidic structure.

The branched separation chamber with either the electrical or optical sorting method provides an unprecedented level of purity and speed in the recovery of specific chromatin sequences. The triggering event for this sorting method is based upon the QD color signature generated during excitation in the laser inspection volume. The emitted fluorescence is observed using high-speed, ultra-sensitive photodetectors such as avalanche photodiodes (APDs), which output digital signals representing the number of photons observed. To initiate a real-time sorting trigger signal, a programmable high-speed hardware unit can perform the rapid decision making process. A field programmable gate array (FPGA) or other logic device may incorporate several operations to make the final sorting decision. The input signal representing fluorescence may be collected using an integrator operation and then buffered to a comparator to decide if a single molecule event has occurred. This operation may be performed for each fluorescence color and corresponding photodetector, simultaneously. When the user-specified condition for sorting is satisfied, the sorting trigger is output to either the adjustable voltage supply (electrical sorting method) or to the phased array that deflects the infrared laser (optical sorting method).

Devices

The present invention provides for systems and devices for analyzing genetic material. In some cases, the systems and devices can be used for performing epigenetic analysis on chromatin. A subject system typically comprises the following components: a channel being adapted to hold an object in a continuous liquid body in said channel, one or more light sources configured to illuminate the channel to create one or more interrogation volumes, and a detection module configured to detect at least two types of signals indicative of two distinct properties of the object in the one or more interrogation volumes. The object can be a chromatin, or a single nucleic acid molecule.

In one aspect, the invention provides for a system for characterizing a single nucleic acid molecule or a chromatin that can comprise a channel configured to hold said molecule, one or more light sources configured to illuminate the channel to create one or more interrogation volumes, a detection system configured to detect at least two types of signals indicative of two distinct properties of said nucleic acid molecule from the one or more interrogation volumes, and a processor programmed to provide real-time time-correlated resolution of the at least two types of signals from said one or more interrogation volumes, thereby characterizing said single nucleic acid molecule.

The invention also provides for a system for characterizing an object that can comprise a channel configured to hold said object, one or more light sources configured to illuminate the channel to create one or more interrogation volumes, a detection system configured to detect at least two types of signals indicative of two distinct properties of said object from the one or more interrogation volumes, a processor programmed to provide real-time time-correlated resolution of the at least two types of signals from said one or more interrogation volumes, thereby characterizing said object, and a user interface configured to receive data from the processor and display the data, wherein the data comprises information on the at least two types of signals from said one or more interrogation volumes.

Figure 27A:
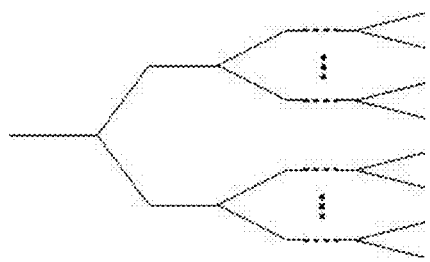
FIG. 27A depicts a channel comprising a plurality of bifurcation points.
Figure 27B:
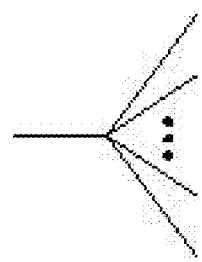
FIG. 27B depicts a channel comprising an upstream channel fluidically connected at a branch point to more than two downstream flow paths or channels.

The present invention provides for methods and devices for high throughput multiplexed single molecule analysis and sorting using a plurality of fluidic channels. The channels can be arranged in a variety of formats, including parallel channels, radial channels, and/or branched channels. For example, FIGS. 1B, 4A, 4B, 28, and 34 show a plurality of channels arranged in a parallel format and FIGS. 27A and 27B show channels arranged in a branched format.

In some embodiments, the systems and devices can also include a downstream sorting module. The devices, which may be nanofluidic or microfluidic devices, provided herein may include a Y-shaped branch point in the flow channel with the ability to sort materials into reservoirs at either of the two ends of the branches. In some embodiments, the nanofluidic devices provided herein may include multiple (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) branch points in a parallel or serial fashion which multiple branch points may further provide multiple outflow tracts or collection chambers. Sorting molecules bearing specific epigenetic marks into separate collection chambers may allow for their recovery and sequencing. In some cases an entire genome may be sorted in less than 10 hours, 8 hours, 7 hours, 6 hours, 5 hours, 4 hours, 3 hours, 2 hours, 1 hour, 45 minutes, 30 minutes, 20 minutes, 10 minutes, 5 minutes or less. The devices of the present invention are quite stable and data may be collected on a device that has been reused many times (e.g. 1, 2, 3, 4, 5, 6, 10, 15, 20, 25, 30, 35, 40, 50, 75, 100, 1000, 10000 times or more).

Channels

The devices of the invention can comprise one or more channels or flow paths. The channels can be fabricated using a variety of techniques, including microfabrication and nanofabrication techniques. The channels can be made from a variety of substrates, including, but not limited to, silica, mirror polished fused silica, silicon, quartz, glass, or polymeric materials (e.g., PDMS, plastics.). Channels may be etched, ablated, molded, into the substrate. The channels or flow paths may be coated. The coating can alter the properties of the channels and may be patterned. For example, the coating may be hydrophobic, hydrophilic, magnetic, paramagnetic, conductive, or be functionalizable depending on the objects to be sorted. The coating or a material complexed, conjugated, or bonded to the coating may exhibit affinity to one or more types of objects. The coating, or a material bound to the coating may reduce the adherence of an object to the channel. An example of a coating material includes PTFE. The channels may have a cross-section that is shaped like a circle, oval, rectangle, square, trapezoid, triangle, pentagon, or any other shape. The channel may have one or more cross-sectional dimensions, e.g., diameter, width and/or height, that is up to about, less than about, or about 10, 20, 30, 40, 60, 80, 100, 200, 250, 400, 500, 550, 600, 700, 800, 900, 1000, 1250, 1500, or 3000 nanometers. The dimension of the channel can be selected to be up to about, more than about, or less than about 1, 2, 3, 4, 5, 6, 7, 8, 9, 10, 15, 20, 25, 50, 75, or 100 times the width of an object to be sorted.

The one or more channels can be fluidically connected to one another at one or more branch points. The one or more channels allow for the sorting of objects in a continuous body of liquid or in a reversible fashion (as described herein). The branch points may be bifurcations, where a single upstream channel is connected to two downstream flow paths or channels at a bifurcation point. As shown in FIG. 27A, a sorting device can have a plurality of bifurcation points. In other embodiments of the invention, one or more channels can be fluidically connected at a branch point to more than two downstream flow paths or channels. As shown in FIG. 27B, a sorting device can comprise an upstream channel fluidically connected at a branch point to four downstream flow paths or channels. In some embodiments of the invention, a device has a plurality of branch points, each branch point having two, three, four, five, or more downstream flow paths or channels. The branch points may have the same or different number of downstream flow paths. The branch points may be T-shaped, Y-shaped, or any variation thereof. The channels may be straight or curved. The channels can be positioned in two or three dimensions, such that all channels are in the same plane, or some channels are in different planes.

The methods and devices can include an array of parallel fluidic channels, numbering between one and several thousand, where each channel has a width and depth less than one micron and a length of a few millimeters. Alternatively, the length of a channel can be about, up to about, greater than about, or less than about 0.01, 0.1, 1, 10, 100, 1,000, or 10,000 millimeters. The parallel channels can have a common input reservoir or individual reservoirs where a collection of molecules, including native DNA, chromatin, RNA, proteins, polysaccharides, or small molecule drugs, is loaded. The molecules loaded and/or analyzed can also include lipids or complexes of any of native DNA, chromatin, RNA, proteins, polysaccharides, or small molecule drug. The molecules may be isolated from cells or tissues. The molecules can be driven through the array of parallel channels by various methods, electrophoretic, electroosmotic, or pressure, and interrogated at a given spatial location along each channel by fluorescent, electrical, or other means. Molecules can be driven at rates of several hundred or thousand per second in each channel independently. The molecules can be hybridized with probes or bound with antibodies or aptamers that signify the presence of a particular location along the molecule (e.g., a gene for DNA) or the presence of an epigenetic mark such as DNA methylation, histone methylation, histone acetylation, histone phosphorylation, etc. The interrogation of all channels can be recorded simultaneously on measurement devices such as photodetectors or ammeters. Based on the quantity measured in real-time during the passage of a molecule through the channel, each molecule can be directed toward one of several possible output channels. This provides for independent sorting in each of the parallel channels, allowing molecules to be directed to one of two or more output channels for subsequent analysis. Such switching of output channels can be accomplished by rapidly switching voltage potentials, applying a dielectrophoretic force transverse to the flow direction, pumping, or other means.

The channels, including downstream flow paths and channels, may have the same of different dimensions. Downstream flow paths or channels may have the same, higher, or lower cross-section area as compared to an upstream channel. The dimensions of the channels can be selected to maintain fluid velocity within the channels. In one example, an upstream channel is fluidically connected at a bifurcation point to two downstream channels and the cross sectional area of each of the downstream channels is half the cross-sectional area of the upstream channel.

The devices described herein, including devices for multiplexed analysis, can be fabricated in silicon, silicon dioxide, glass, borosilicate, polymeric, or fused silica chips using a variety of standard micro- and nanofabrication techniques including photolithography, electron beam lithography, reactive ion etching, and embossing.

Figure 1C:
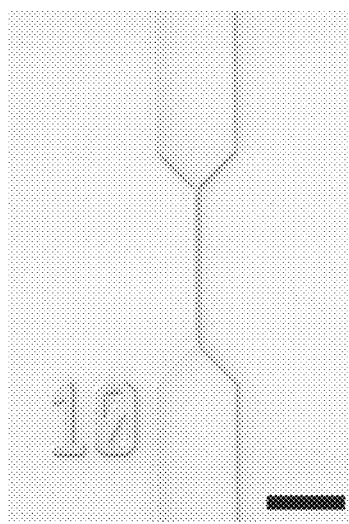
Figure 2:
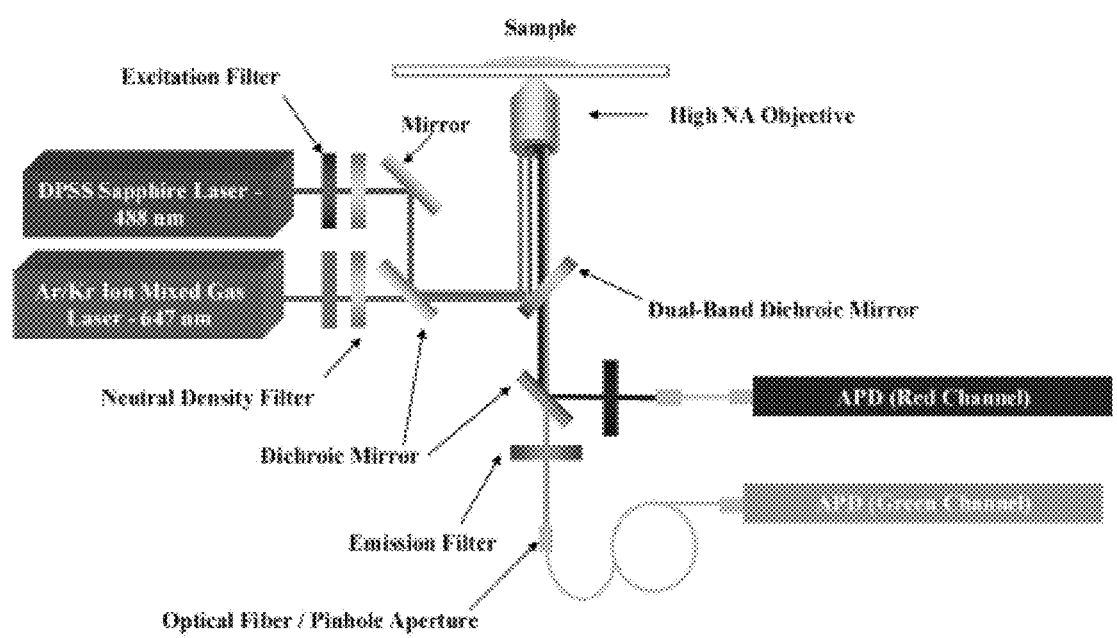
FIG. 2 depicts a block diagram of one embodiment of the device of the present invention. Lasers may be used to excite fluorophores associated with chromatin directed by electrokinetic flow through a nanoscale device mounted on an imaging platform such as a confocal microscope. Photons emitted by the DNA specific label and the epigenetic modification specific label may be separately detected using photodetectors such as avalanche photodiodes (APD). Alternatively, other detection regimes may be employed in the devices and methods of the present invention such as detection of magnetic or electrical properties. Similarly, methods and devices other than those requiring a microscope may be employed for data collection such as solid state methods and methods allowing data collection for multiple fluid channels simultaneously.

The devices of the present invention may consist of channels with submicrometer width and height fabricated in fused silica substrates by means of optical lithography and plasma etching (FIG. 1). In a typical experiment, a fluorescent molecule is driven by electrokinetic flow (like gel electrophoresis only in the fluid phase), through the channel and excited by a focused laser beam as shown in FIG. 2. The light emitted from the fluorophore is collected and quantified by a photodetector. These experiments demonstrate our ability to perform high throughput multicolor imaging and quantitative analysis of biological molecules on our devices, methods readily adapted to epigenomic analyses. For example, FIG. 3 depicts single DNA molecules labeled with a fluorescent dye flowing though the channels. This is a novel design because it drastically reduces the sample studied to a limit beyond that possible with conventional optics alone and incorporates a fluidic structure to allow all molecules to be analyzed rapidly and equally on an individual molecule basis.

Other examples of channels and systems for analyzing and/or sorting an object can be found in U.S. Patent Application Nos. 2009/0050542, and 2009/0234202, U.S. Pat. Nos. 6,927,065, 7,405,434 and 6,833,242, and PCT Publication No. WO/2010/044932 which are each incorporated herein by reference in their entirety.

Detection Module and Light Sources

The system can comprise one or more detection modules configured to measure a signal corresponding to a property of the object or genetic material to be analyzed. The detection modules described herein can utilize a variety of detection techniques. The detection modules can detect optical, electrical, radioactive, physical (e.g., size, density, thermal conductivity, elasticity, viscosity, and strength), and/or magnetic properties. The choice of a detector can depend on the type of label used. For example, an optical detector can be used to detect a fluorescent label, and a conductance meter or electrical detector can be used to detect a metallic label. Examples of electrical detection systems are described in PCT Publication No. WO/2010/044932, which is hereby incorporated by reference in its entirety. An electrical detector can comprise a wire, a nanowire, a nanotube, a transistor, or a capacitor placed in proximity to a detection zone. The electrical detector can be made of carbon, silicon, carbon/silicon, or other semiconducting material.

A detection module utilizing optical detection of a property of the object can comprise a light detector or photodetector. The light detector can be a CCD, CMOS array, photomultiplier tube, avalanche photodiode (APD), single photon counting modules, photoresistors, photovoltaic cells, phototransistors, LEDs, and any combinations thereof.

The detection module can include one, two, three, four or more light sources configured to illuminate a channel. The light sources can be configured to create one or more interrogation volumes. The light sources can include lasers, LEDs, fluorescent lamps, incandescent lamps, halogen lamps, gas-discharge lamps, and/or high-intensity discharge lamps. The one or more light sources can emit one or more beams of light that illuminate one or more regions or volumes within the one or more channels. The beam of light may be focused by an optical component, e.g., a high numerical aperture objective. The beams of light illuminating the channels can create one or more inspection volumes that are defined by the walls of a channel and the beams of light. The dimensions of the beam of light and the channel can define the size of the inspection volume, as shown in FIG. 3. The inspection volumes can have a volume that is about, up to about, or greater than about 0.01, 0.05, 0.1, 0.2, 0.5, 0.75, 1, 5, 10, 25, 50, 75, or 100 femtoliters. The term inspection volume can also be referred to as an interrogation volume, optical volume, or a detection volume. The interrogation volume can be sized to hold a single object, single chromatin, or single nucleic acid. In some embodiments, the interrogation volume can be sized to hold only a portion of a single object, single chromatin, or single nucleic acid.

The light source can create a beam of light that is up to about, about, or greater than about 0.1, 1, 5, 10, 50, 100, 200, 280, 300, 500, 750, 1000, or 2000 W within the interrogation volume.

In some embodiments, the plurality of light beams emit distinct spectrums or wavelengths of light into the same or different locations in the channel. The beams of light may create overlapping interrogation volumes or distinct interrogation volumes. The beams of light may have a diameter of about, less than about, or greater than about the width of the channel. In some embodiments, the beam of light is about, up to about, or greater than about 1, 1.5, 2, 3, 4, 5, 6, 7, 8, 9, or 10 times wider than the width of the channel. The width of the beam of light can be selected such that the light within the channel is substantially uniform.

The detection module can also include one or more optical components. For example, the detection module can include one or more high numerical aperture objectives or lenses, optical fibers, mirrors, dichroic mirrors, gratings, filters, and confocal apertures. The arrangement of the light source, detectors, and optical components can allow for detection of one, two, three, four, five, six, or more optical signals. The detection can be simultaneous or time-correlated. The resolution and/or accuracy of the time-correlation and/or time-dependent signal can be up to about or about 0.0001, 0.0005, 0.001, 0.005, 0.01, 0.05, 0.1, 0.5, 1, 5, 10, 50, 100, 500, or 1000 milliseconds. The resolution and/or accuracy of the time-correlation and/or time-dependent signal can be up to about or about 0.0001, 0.0005, 0.001, 0.005, 0.01, 0.05, 0.1, 0.5, 1, 5, 10, 50, 100, 500, or 1000 microseconds. The resolution and/or accuracy of the time-correlation and/or time-dependent signal can be up to about or about 0.0001, 0.0005, 0.001, 0.005, 0.01, 0.05, 0.1, 0.5, 1, 5, 10, 50, 100, 500, or 1000 nanoseconds.

Several thousand molecules can be interrogated each second in each of several thousand parallel channels. By recording the response of each molecule, which may be simultaneous and/or sequential, to an external stimulus the devices described herein can analyze several orders of magnitude more molecules than present technology allows.

The analysis is an improvement over prior technology in terms of molecules analyzed per time, per device footprint, per reagent volume used, or any combination thereof. The device can be used to rapidly analyze and sort a variety of molecules and/or complexes. The molecules and/or complexes can include individual DNA, RNA, chromatin, protein, polysaccharide, or small drug molecules, or lipids, or complexes of individual DNA, RNA, chromatin, protein, polysaccharide, or small drug molecules, or lipids. The molecules and/or complexes can be analyzed for a range of biologically relevant information including binding efficiency to various probes, or the presence of various other biological markers signifying the presence of genes, epigenetic marks, or haplotype information.

The one or more detectors can be configured to transmit information regarding the one or more detected signals to a processor. The processor can be a programmable logic device, a computer, or any other component that can record or interpret the signal. The processor may be a component of a sorting module, described herein.

Processor and Computer System

The system can comprise a processor that interprets one or more signals measured by the detection module and/or directs an object to one of a plurality of downstream channels or flow paths. The information transmitted by the detection module or the detector can be received by a processor. The processor can be a computer or a programmable logic device, e.g., a field-programmable gate array (FPGA), programmable array logic (PAL), generic array logic (GAL), or complex programmable logic device (CPLD). The processor can operate at about, up to about, or greater than about 15, 25, 50, 60, 75, 100, 200, 500, 1000, or 2000 Hz, MHz, or GHz. In some embodiments, the processor is an FPGA that can interpret data and return instructions in less than about $1\times10^{-2}$, $2\times10^{-2}$ $1\times10^{-3}$, $1\times10^{-4}$, $1\times10^{-5}$, $1\times10^{-6}$, or $1\times10^{-7}$ seconds. The processor can be programmed to receive a signal and/or direct an object to one of a plurality of downstream flow paths based on the signal. The conditions for sorting an object to one path or another can be programmed into the processor by a user via a user interface on a computer system or another device. The conditions for characterizing and/or sorting an object can include simultaneous or time-correlated detection of two, three, four, five, six, or more signals. Detection of more one, two, three, four, five, six, or more signals above a preselected threshold can be used to discriminate objects. In some embodiments, the signals correspond to optical, electrical, magnetic, radioactive, or physical properties of the object. The signals measured can be indicative of distinct properties of the object.

The processor can interpret the data to determine how to sort the object and transmit instructions to a sorting actuator or transmit information regarding properties of the object to a computer or a recording device. The processor can interpret data obtained at one interrogation volume positioned in an upstream channel and provide instructions to a sorting actuator to direct the object to one of a plurality of downstream flow paths at one, two, three, four, five, or more branch points. The processor can interpret data obtained at one interrogation volume and return instructions to a sorting actuator to direct the object to one of a plurality of downstream flow paths at a branch point immediately adjacent and/or downstream to the interrogation volume. The branch point can be a known distance, volume or time away from the interrogation volume. Precise knowledge of the distance, volume, or time between the interrogation volume and the branch point can allow for accurate and/or precise sorting of the object. Reduction of the distance, volume, or time between the interrogation volume and the branch point can increase the precision and/or accuracy of sorting.

A sorting actuator can perform sorting of the object by changing the trajectory or flow path of the object. The sorting actuator can also change the trajectory or flow path of the object or of a fluid carrying the object. The sorting actuator can sort the object by physically altering the flow paths within the channels and downstream flow paths, or by imparting magnetic, electrical, or optical forces. In some embodiments, the sorting actuator can comprise one or more electrodes that impart an electrokinetic force on the object. Alternatively, the sorting actuator can comprise one or more valves that change the flow path of a fluid carrying the object. The valves can be pneumatic valves, mechanical vales, magnetic valves, rotary valves, hydraulic valves, piezoelectric valves, shuttle valves, elastomeric valves, and electrical valves. In some embodiments, electrodes can also be used to change the flow path of a fluid carrying the object. Electrostatics can also be used to alter the flow path of an object. Optical tweezers may also be used to alter the flow path of an object by placing the object in a position to flow down one of a plurality of downstream flow paths or deflecting the object toward one of a plurality of downstream flow paths. Optical tweezers can be used in the invention to trap and move objects, e.g. molecules or cells, with focused beams of light such as lasers.

The system can be operably linked to a computer that has a user interface for controlling sorting system (e.g., the detection module and the sorting module), programming the programmable logic device, and displaying results. The computer can be an integral part or a separate part of the subject sorting system. The user interface can be a graphical user interface. The user interface can display the measurements by the detector, the analysis of the object, and the sorting of the object, which may be in real-time. The user interface can allow for selection of operating conditions, e.g., voltage gradient, sorting conditions, signal thresholds, total sorting time, light source power, and detector calibration. The operating conditions can be inputted using a keyboard, mouse, or other input device.

In some embodiments of the invention, the sorting system comprises a memory module for storing data transmitted by the processor and/or detector during sorting. The memory module can be accessed during sorting or subsequent to sorting to retrieve data collected during sorting.

The analytical system described herein can also comprise a computer system for user interaction and data retrieval. The computer system can have a user interface for inputting experimental parameters and displaying the results of the analysis. The user interface can display data in real-time. The computer system can have a display device for displaying the user interface and displaying the real-time data.

Exemplary Applications

The subject system provides an effective tool for sorting and/or analyzing an object at a single-object level. The subject system finds a vast array of applications including, but not limited to, genetic analysis such as epigenetic analysis of chromatin, sorting of cells, nucleic acid molecules, proteins, carbohydrates, lipids, and any combination thereof.

Detection of Quantum Dots

Fluidic channels with submicrometer dimensions of the present invention may be used to isolate, detect and identify individual quantum dots (QDs) conjugated with organic fluorophores. The channels may be fabricated in fused silica with a 100, 200, 300, 400, 500, 600, 750 or 1000 nm square cross section. The resulting focal volume of approximately 100-1000 attoliters reduces fluorescent background and increases the signal to noise ratio of single molecule detection. The channels allow for the rapid detection of 50%, 60%, 75%, 90%, 95%, 99%, 99.5%, 99.9% or more of the QDs and organic fluorophores traversing the focal volume.

Figure 6A:
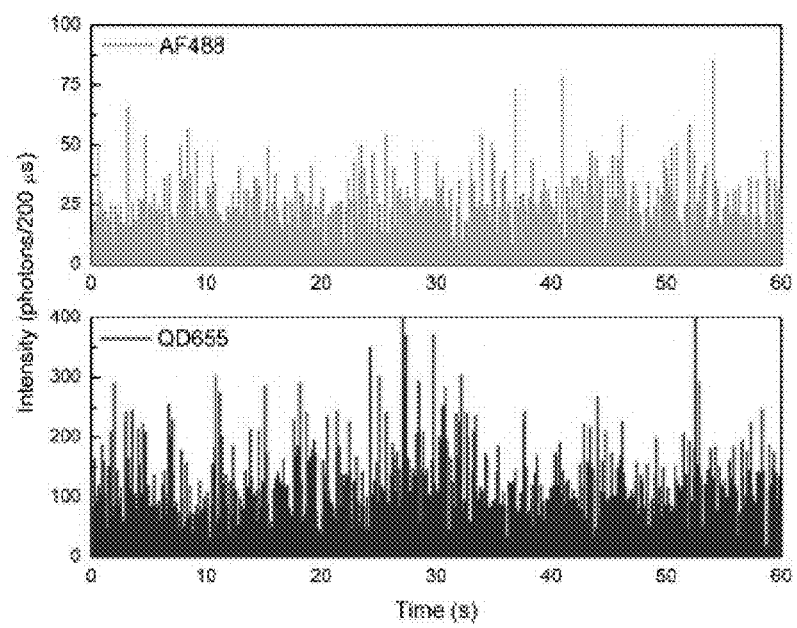
FIGS. 6A and 6B depict single molecule data collected by a device of the present invention.
Figure 6B:
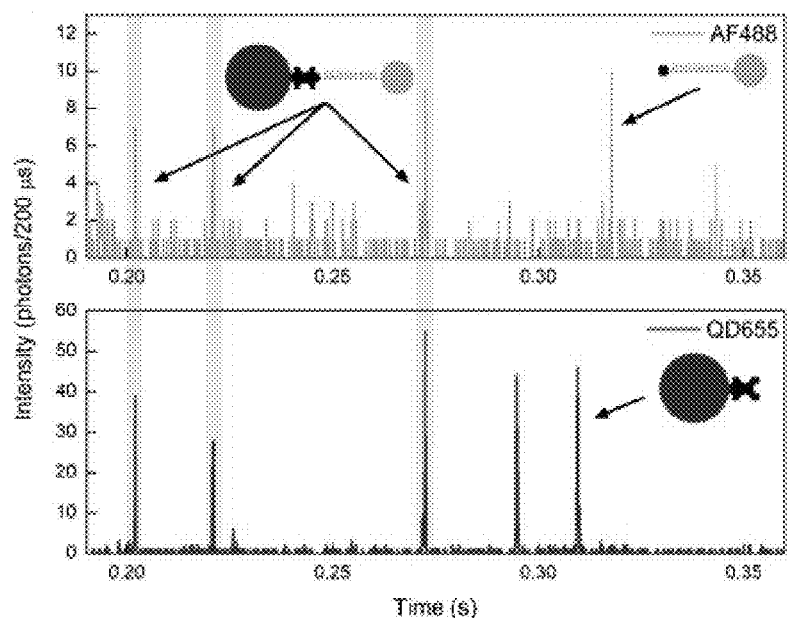

QD conjugates may be driven through the channels electrokinetically excited with a single wavelength laser and detected with a confocal microscope. Fluorescence emission may be collected simultaneously from green and red regions of the spectrum. Signal rejection may be minimized by the narrow and symmetric emission spectra of the quantum dots. For efficient multicolor detection and characterization of single molecule binding, QDs may be bound to Alexa Fluor 488 (AF488) molecules and individually detected as shown in FIG. 6. The union of fluidic channels with submicrometer dimensions and QDs as fluorescent labels results in efficient and rapid multiplexed single molecule detection and analysis.

Analysis of Methylation States

Analysis of DNA methylation states using purified mammalian DNA may be performed using the devices and methods of the present invention. Further, the devices and methods of the present invention provide for analysis of mammalian chromatin. Still further, the devices and methods of the present invention allow for simultaneous analysis of multiple epigenetic marks (multiplexed analysis) to assess their frequency and coincidence. For example, embryonic stem (ES) cell and mouse embryonic fibroblast (MEF) cell chromatin may be analyzed simultaneously for several marks including: DNA methylation, DNA hydroxymethylation, H3K27me3; H3K27me3 and H3K4me3; and H3K27me3, H3K4me3, bound RNA polymerase II (RNA pol II), bound SWI/SNF, and any other DNA or chromatin bound protein, or any other known epigenetic marker. These marks have been implicated in each other's mutual regulation and also as fundamental, collaborating regulators of mammalian development. An additional component of this invention is the ability to perform the multiplexed analysis from these high abundance sources of chromatin to low abundance sources, namely microdissected tumors, preimplantation embryos, and other low abundance sources.

Analysis Using QD Label to Methylated DNA

Figure 10A:
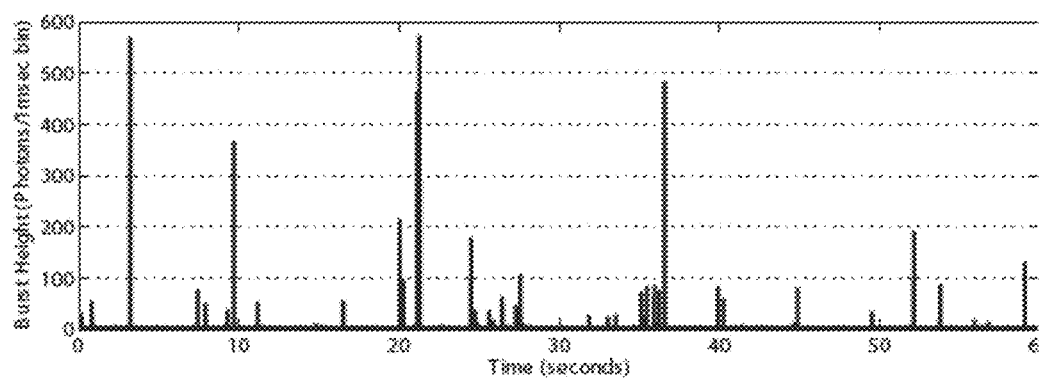
FIG. 10A illustrate a representative 1 minute time scan of DNA-antibody conjugates at 1 ng/ul. Quantum dot labeled antibody channel on top, Labeled DNA channel on bottom.
Figure 10A:
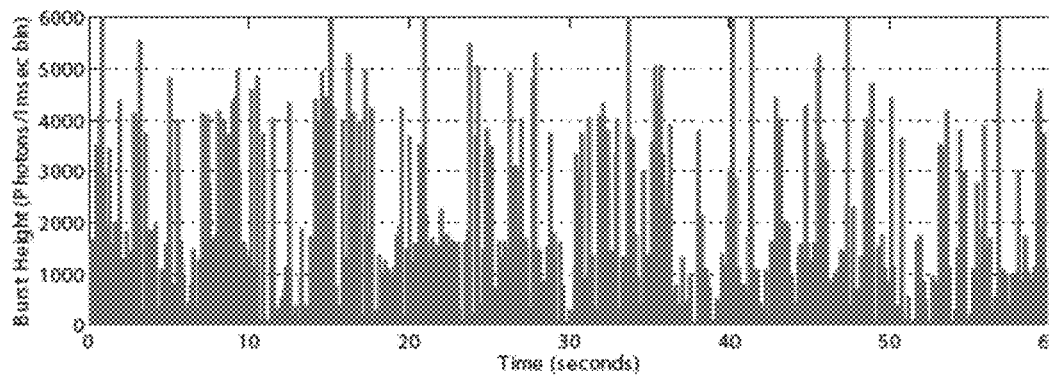
Figure 10B:
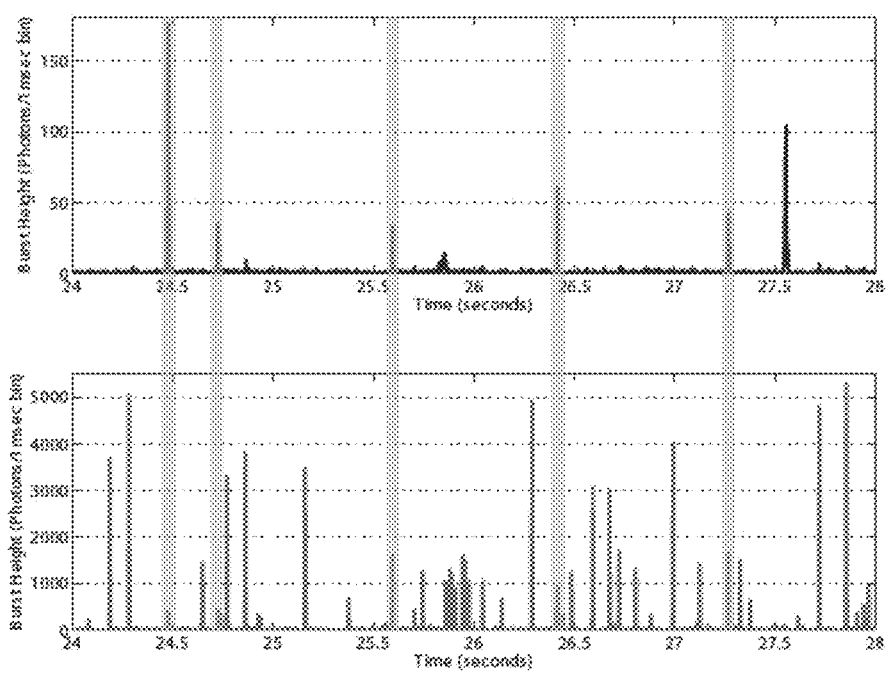
FIG. 10B illustrates an expanded view of the time scan on the left, from 24-28 seconds, to clearly demonstrate single molecule bursts. Time coincident bursts in both detection channels are shaded.

The methods described above may further be used to analyze methylated DNA of eukaryotic or prokaryotic origin using QD-anti-methyl-C antibody and methylated DNA in a device of the present invention. QD-antibody conjugates are passed through fluidic devices with submicrometer cross-sectional dimension at a dilute concentration of approximately 10 pM (or 1 ng/ul of IgG mass antibodies). A bias of +25 Volts is applied to create electrokinetic flow. The number of conjugates observed averages approximately 100/min. Higher molecule-counting rates are possible with higher voltages and antibody concentrations (e.g. 100, 200, 300, 400, 500, 600, 700, 1000, 10000 or more). The fluorescent bursts observed are indicative of both individual QD-anti-methyl-C conjugates (short peaks) and small bound clusters of the conjugates (taller peaks whose heights are approximately multiples of short peaks, FIG. 10).

Figure 11:
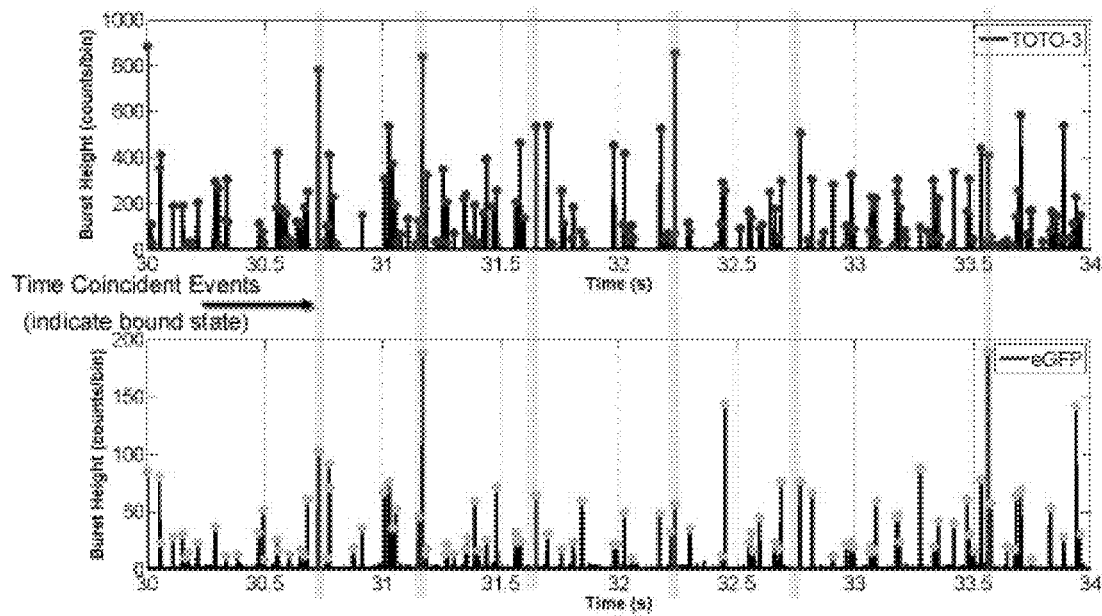
FIG. 11 illustrates single molecule data collected by a device of the present invention. The shaded areas highlight time coincident DNA and nucleosome detection which indicates single molecule detection of DNA and nucleosomes simultaneously.
Figure 12:
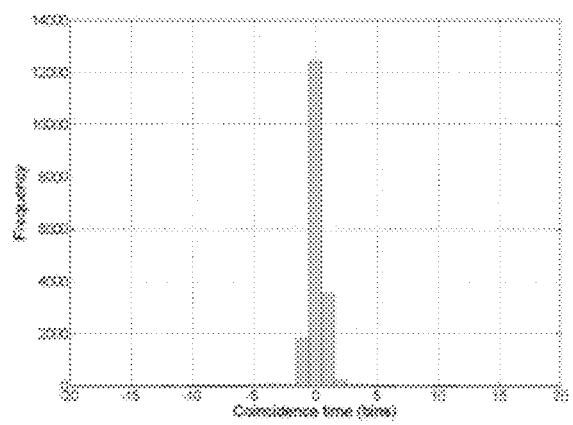
FIG. 12 illustrates time coincidence of GFP tagged histone H2B (H2B-GFP) nucleosomes and TOTO-3 labeled DNA. Single molecule events with each fluorophore color may be analyzed for their time-coincidence to identify bound DNA-histone complexes, or nucleosomes. Under the conditions tested, over 95% of the coincidence bursts occur within +/−1 time bin (bin time is 500 microseconds), illustrating excellent co-localization of the DNA and histones. This sample may be prepared using a 5-min micrococcal nuclease digestion and labeled with TOTO-3 at 1:5 (dye: base pair).
Figure 14A:
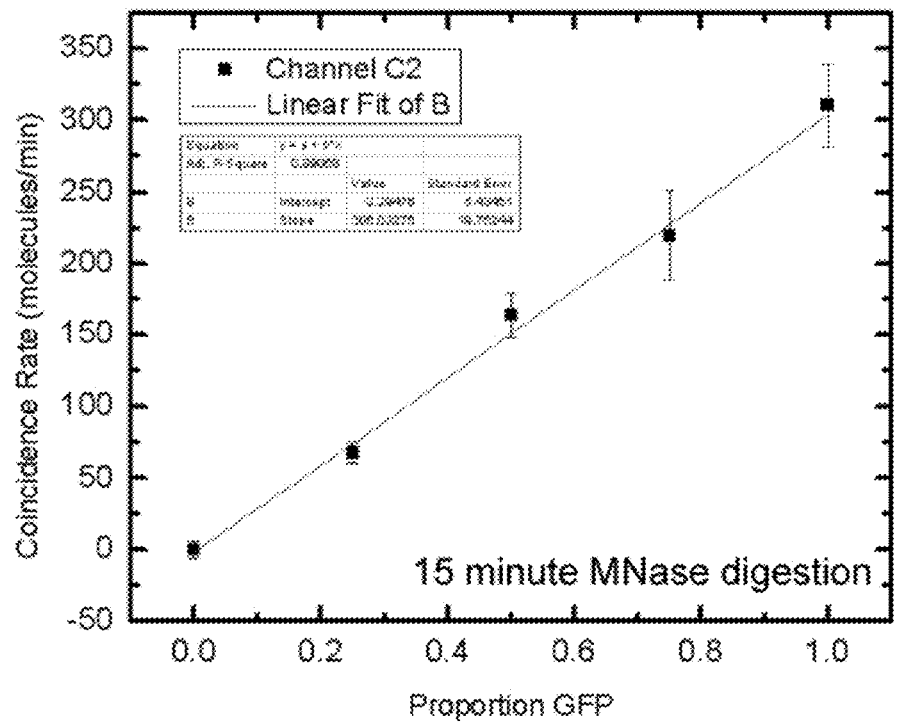
FIGS. 14A, 14B, 14C, and 14D illustrate that dilution analysis confirms GFP (nucleosome label) and TOTO-3 (DNA label) coincidence measurements. HeLa cells expressing H2B-GFP are admixed with HeLa cells lacking the GFP transgene in the proportions shown on the X-axis, then prepared chromatin from the mixtures using micrococcal nuclease digestion times of 15 and 5 minutes. The chromatin is labeled with TOTO-3 and coincidence measurements are performed.
Figure 14B:
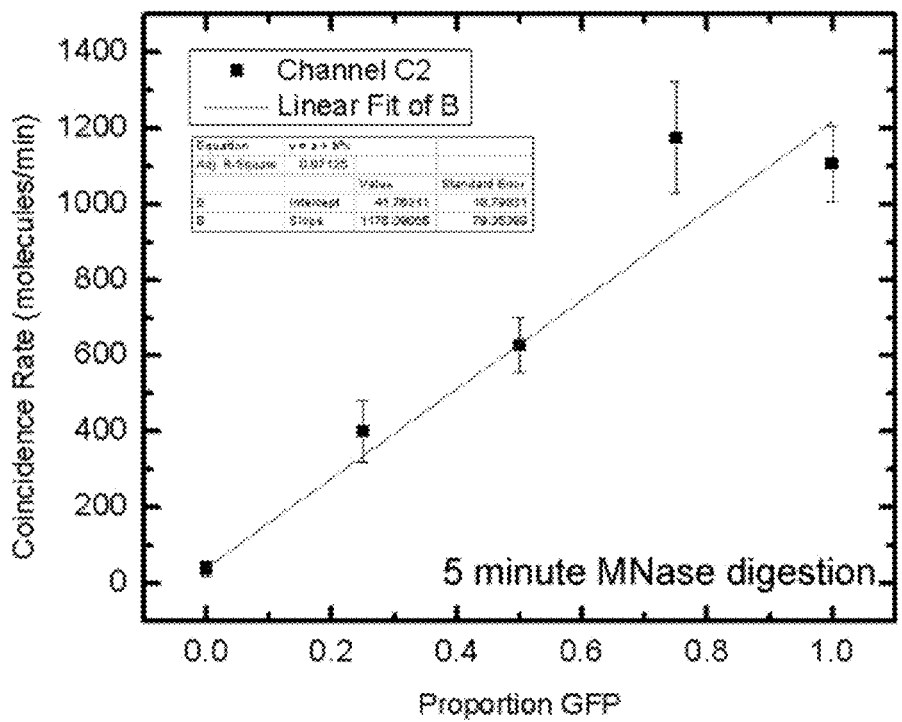
Figure 14C:
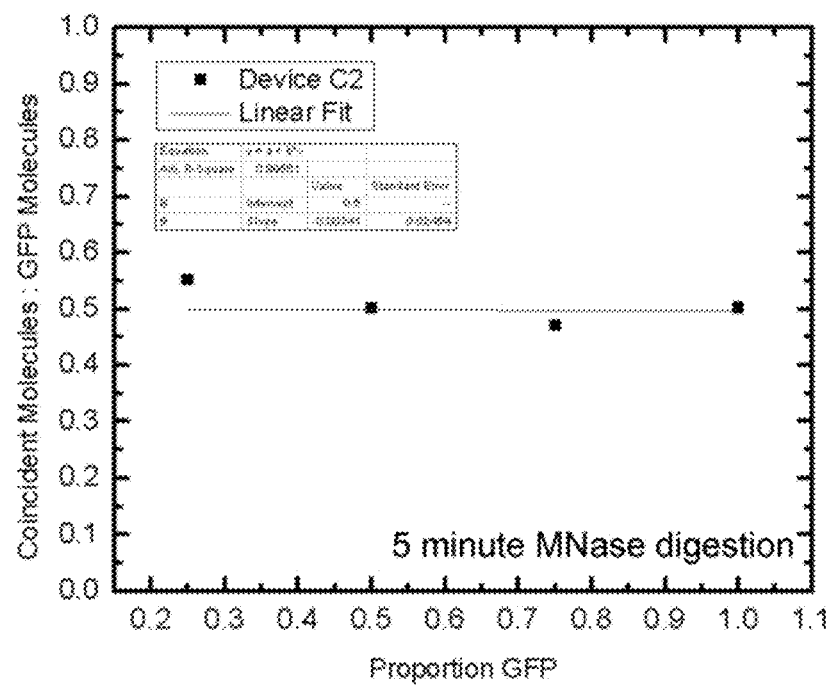
Figure 14D:
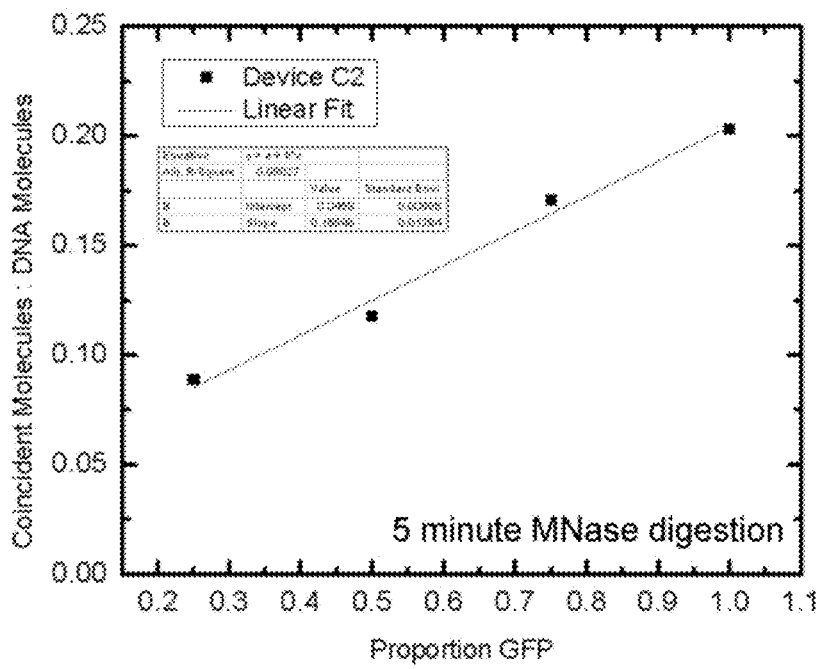
Figure 15A:
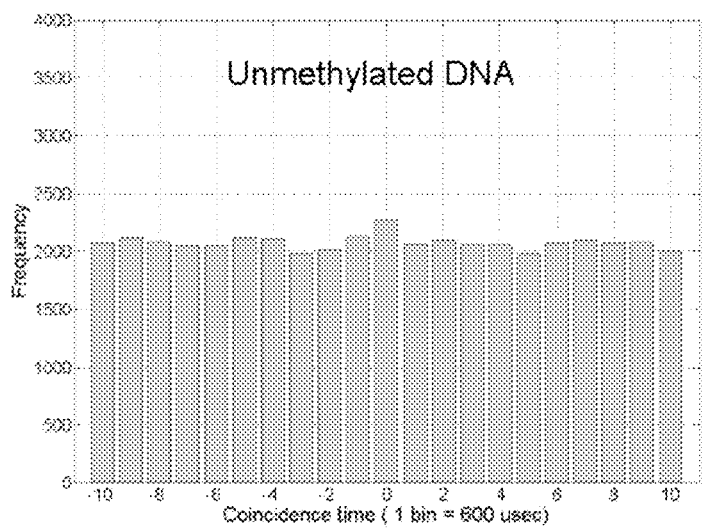
FIG. 15A and FIG. 15B depicts time coincident detection of methylated DNA and a reagent designed to detect methylated DNA (FIG. 15A), and the lack of time coincident detection of the reagent and unmethylated DNA (FIG. 15B).
Figure 15B:
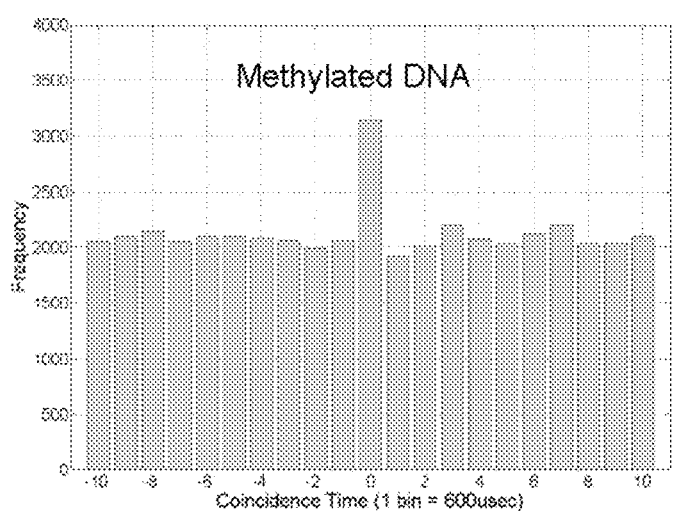
Figure 16A:
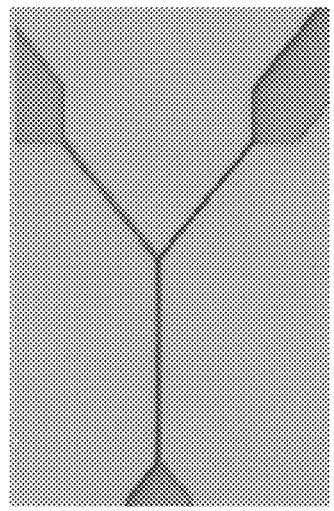
FIGS. 16A, and 16B depict micrographs of embodiments of exemplary analytical and preparative devices of the present invention.
Figure 16B:
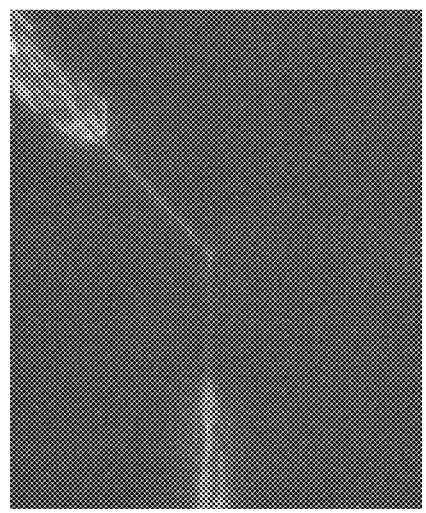

Next, methylated DNA is labeled with YOYO-1 or TOTO-3, and a methylated DNA detection reagent such as a QD-labeled-anti-methyl-C antibody or a labeled MBD1 and flowed the mixture through a device of the present invention. In this way, a two-color time coincidence experiment is constructed to directly observe the presence of methylated sites (red, QD label) on the DNA (green, YOYO-1 label). The DNA antibody mixture is at a dilute concentration of approximately 90 pM (or 1 ng/ul of DNA). Coincidence between YOYO-1 or TOTO-3-labeled DNA and QD-anti-methyl-C may clearly be identified (FIG. 11).

In some embodiments of the present invention input DNAs may be isolated from wild type ES cells and ES cells homozygous for a deletion of genes, e.g., Dnmt1. The Dnmt1 mutant DNAs have their total methylation diminished to levels approximately 15% that seen in wild type cells. Low frequencies of coincidence between QD-anti-methyl-C and YOYO-1 signals may be provided when imaging DNA from the Dnmt1−/− cells. In contrast, DNA from wild type ES cells, may provide robust signals for DNA methylation, consistent with what has been shown by standard restriction enzyme analysis for DNA methylation in wild type ES cells. Dnmt1 mutant ES cell DNA that has been treated with the SssI methyltransferase may further increase the levels of DNA methylation signals.

Gene Expression Analysis

In still other embodiments, the methods and devices provided herein may provide for gene expression analysis of cells or tissues. The present invention may be suitable for gene expression analysis of samples from any source comprising RNA or mRNA. In some cases, the present invention may be particularly useful for gene expression analysis of samples from low abundance or limited sources such as microdissected tumors, pre-implantation embryos, blastocysts, stem cells, or embryonic stem cells. In some cases, gene expression analysis may be provided by contacting a sample comprising labeled RNA (e.g. labeled mRNA) with a device of the present invention, flowing or propelling the RNA through a submicrometer channel comprising a detection area and detecting the labeled RNA. In some cases, the detection may provide single molecule resolution. In some cases, the RNA may further be contacted with a second label or probe or population thereof such as an oligonucleotide probe or population of oligonucleotide probes that specifically bind to or identifies specific sequences of RNA. In some cases, the probe may comprise a second label. In some cases, the time coincident detection of a labeled RNA and a labeled probe may provide for gene expression analysis. In some cases, this time coincident detection may provide one or more of high throughput gene expression analysis, quantitative gene expression analysis, or gene expression analysis at single molecule resolution.

Genome Wide Analysis

In addition to validating that methylation of mammalian DNA can be detected with high sensitivity and specificity, it is worth noting that the present invention may also reveal the frequency and density of DNA methylation that exists across a genome, such as an ES cell genome, for example a mouse or human ES cell genome. Current estimates suggest that 60-80% of the CpGs in the mammalian genome are methylated. But because only 0.1% of the genome has been tested directly for DNA methylation status, the proportion of DNA fragments carrying methylation and the density of methylation per fragment is unknown. The present invention may reveal that information because a very large number of labeled DNA fragments may be detected and methylation density may be detected on each fragment, which is directly proportional to the burst intensity per fragment. The devices retain their function for weeks at a time. In less time than it takes to run an agarose gel, the present invention provides for reliably sampling and imaging individual DNA fragments representing the entire mammalian genome.

DNA Sizing and Labels to DNA

Figure 5A:
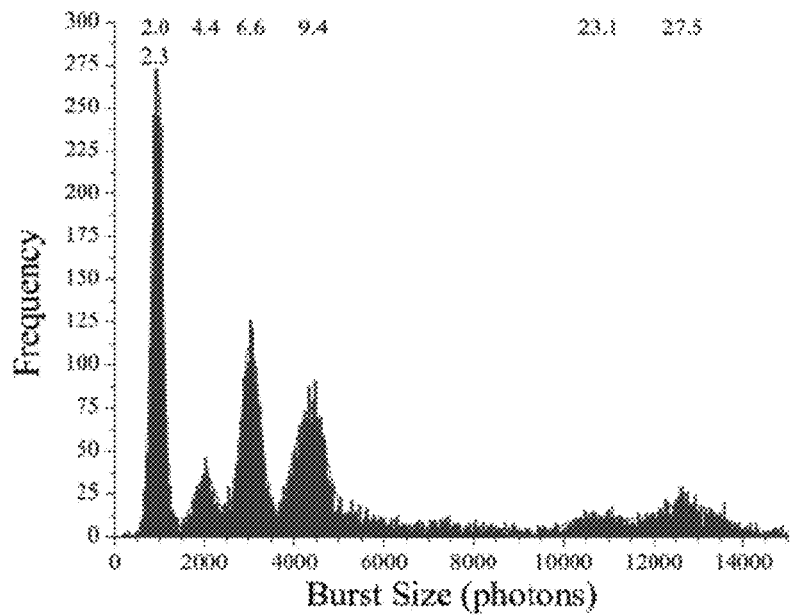
FIGS. 5A and 5B depict the results of a DNA fragment sizing experiment.
Figure 5B:
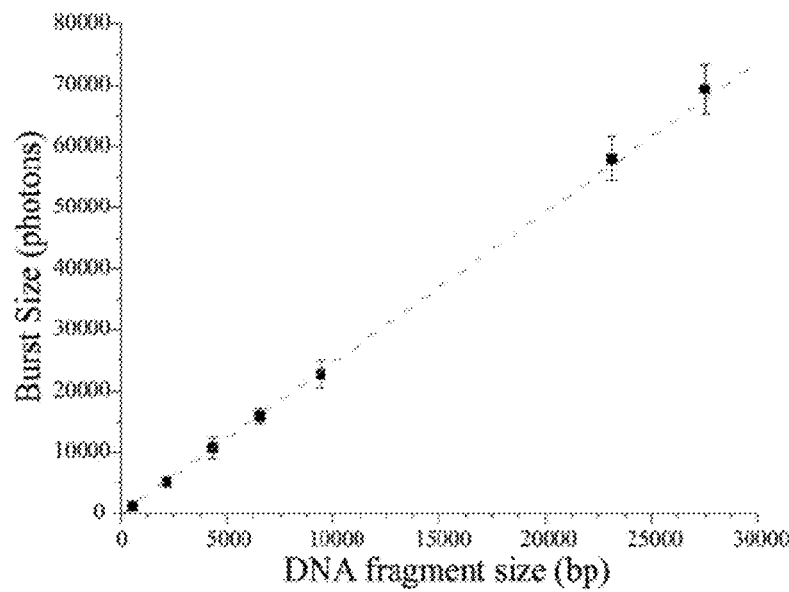

Single molecule DNA fragment sizing may be performed on the devices of the present invention. For example, a lambda DNA marker may be digested with HindIII to form fragments of known lengths between approximately 600 bp and 27,000 bp. The fragments may be labeled with an intercalating dye, e.g. YOYO-1, TOTO-3, Syber Green, ethidium bromide or any other suitable dye, and electrokinetically driven through the channel where they are individually interrogated by a focused laser. The molecules may be uniformly driven at velocities up to 1 mm/s, 2 mm/s, 5 mm/s, 10 mm/s, 20 mm/s, 40 mm/s, 50 mm/s, 75 mm/s, 100 mm/s, 250 mm/s, 500 mm/s or higher allowing for analysis rates of 1,000; 2,000; 3,000; 4,000; 5,000; 6,000; 10,000; 15,000; 20,000; 30,000; 50,000; 75,000; 100,000 or more molecules per minute. Since the molecules are uniformly stained with the fluorescent intercalating dye, the number of photons emitted by each molecule as it flowed through the laser spot is proportional to its length. FIGS. 5A and 5B show the number of photons (burst size) collected from the various fragment sizes as well as the measured linear relationship between the burst size and the known fragment size. Comparison of fragment analysis using this technique is also compared against gel electrophoresis, resulting in excellent agreement.

Sorting of Methylated and Unmethylated DNA

The devices of the present invention may be used to sort mixtures of DNAs (e.g., HindIII digested lambda DNA) that are either unmethylated or methylated by SssI, which methylates all CpGs. DNAs may be labeled with a DNA specific dye such as YOYO-1 or TOTO-3 and with a methylated DNA specific label such as QD-anti-methyl-C. DNA fragments may then be sorted according to their methylation state as reported by the QD-anti-methyl-C. At a sort rate of 4,000 fragments per minutes, nearly 600 copies of each of the seven lambda HindIII fragments may be sorted in one minute. Bisulfite sequencing, may then be performed using the input mixture, the sorted methylated DNA and the sorted unmethylated DNA, and sequencing primers for each of the seven fragments. Pyrosequencing may also be performed on the input mixture, the sorted methylated DNA and the sorted unmethylated DNA.

Mouse or human DNA may also be sorted by using approximately 20,000 bp fragment sizes as input. Input DNAs may be DNAs from ES cells that carry a Dnmt1 mutation and DNAs from wild type or other mutant ES cells. The Dnmt1 mutant DNAs have their total methylation diminished to levels approximately 15% of those seen in wild type cells, however, at the highly repeated IAP element (>1,000 copies in the mouse genome), methylation is reduced to essentially undetectable levels. Sorted samples may have plenty material to use for bisulfite analysis by pyrosequencing.

Mouse or human chromatin may also be sorted by the methods of the present invention. For example, antibody recognizing H4K20me3 and H3, each coupled to a spectrally-distinct QD, and may be used to sort the chromatin into two populations, one enriched for both marks and the other lacking the H4K20me3 mark. Real time PCR using primers specific for the genomic region of interest may further be used to measuring the content of that region of interest in the two sorted populations relative to the unsorted input material.

ES chromatin may also be sorted using antibodies for two separate epigenetic marks, such as for example H3K4me3 and H3K27me3. These are marks that define the bivalent state of chromatin in ES cells as determined by ChIP-Chip and by ChIP-Seq. After a sort that ensures at least 1× genome coverage, the sorted material can be sequenced by any methods known in the art including the use of a Solexa or 454 sequencing technique. The devices and methods herein can therefore be used to analyze materials from low abundance sources and for multiple epigenetic marks simultaneously.

Resolving Dendrimer-Like DNA

Figure 7A:
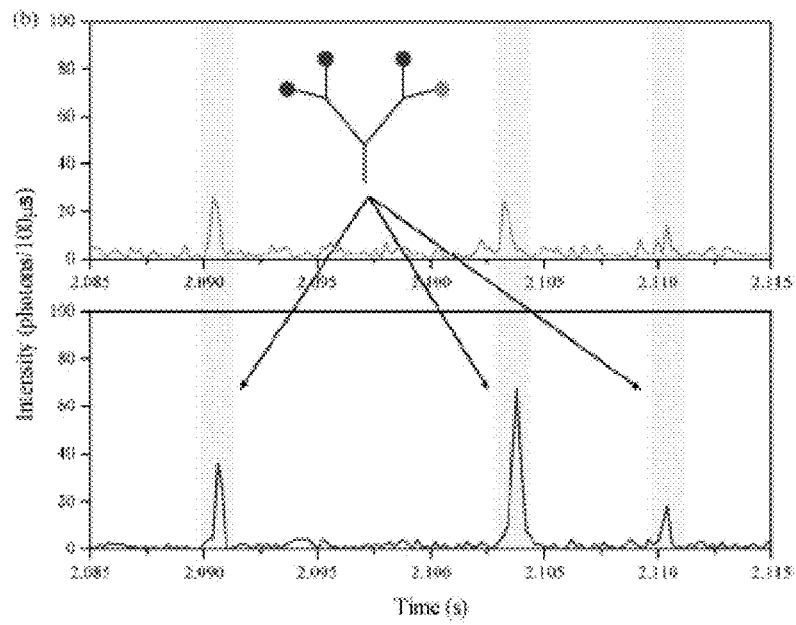
FIGS. 7A and 7B depict single molecule data collected by a device of the present invention for detection of fluorophore labeled nucleic acid dendrimers.
Figure 7B:
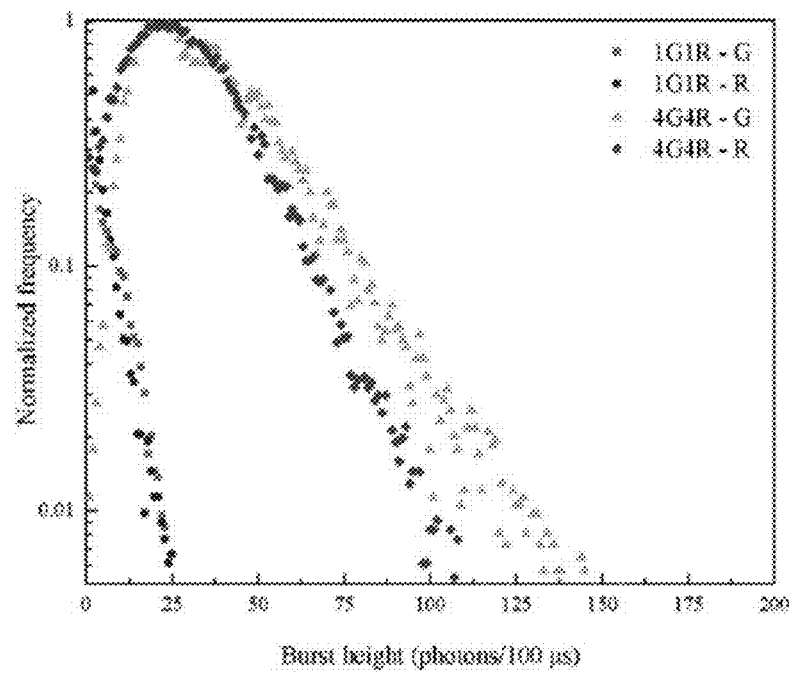

Two-color single molecule spectroscopy may be provided by the methods and devices of the present invention further demonstrated for resolving "dendrimer-like DNA" labeled with different combinations of fluorophore quantity and color. These dendrimers are synthetic branched DNA molecules. These data demonstrate the ability to perform quantitative simultaneous multicolor analyses of DNA on devices of the present invention. Coincident lasers of two different wavelengths such as for example 488 nm and 568 nm wavelengths may be focused on a submicrometer fluidic channel to perform measurements of coincident, fluorophore emission intensity, see FIGS. 7A and 7B. The nucleic acid engineered (NAE) labels are composed of Alexa Fluor 488 and BODIPY 630/650 labeled to each Y-shaped DNA subunit (FIGS. 7A and 7B), which are then assembled into larger dendrimer-like networks. Fluidic channels are constructed from fused silica substrates for low autofluorescence background. The inspection volume is uniformly illuminated and analyte flow is controlled with electrokinetic drive, allowing each molecule to be excited equally. More on resolution of dendrimer-like DNA is described in Stavis et al. Detection and identification of nucleic acid engineered fluorescent labels in submicrometre fluidic channels. 2005 Nanotechnology 16 S314-S323, which is hereby incorporated by reference in its entirety.

Analysis of PCR Products

Figure 8A:
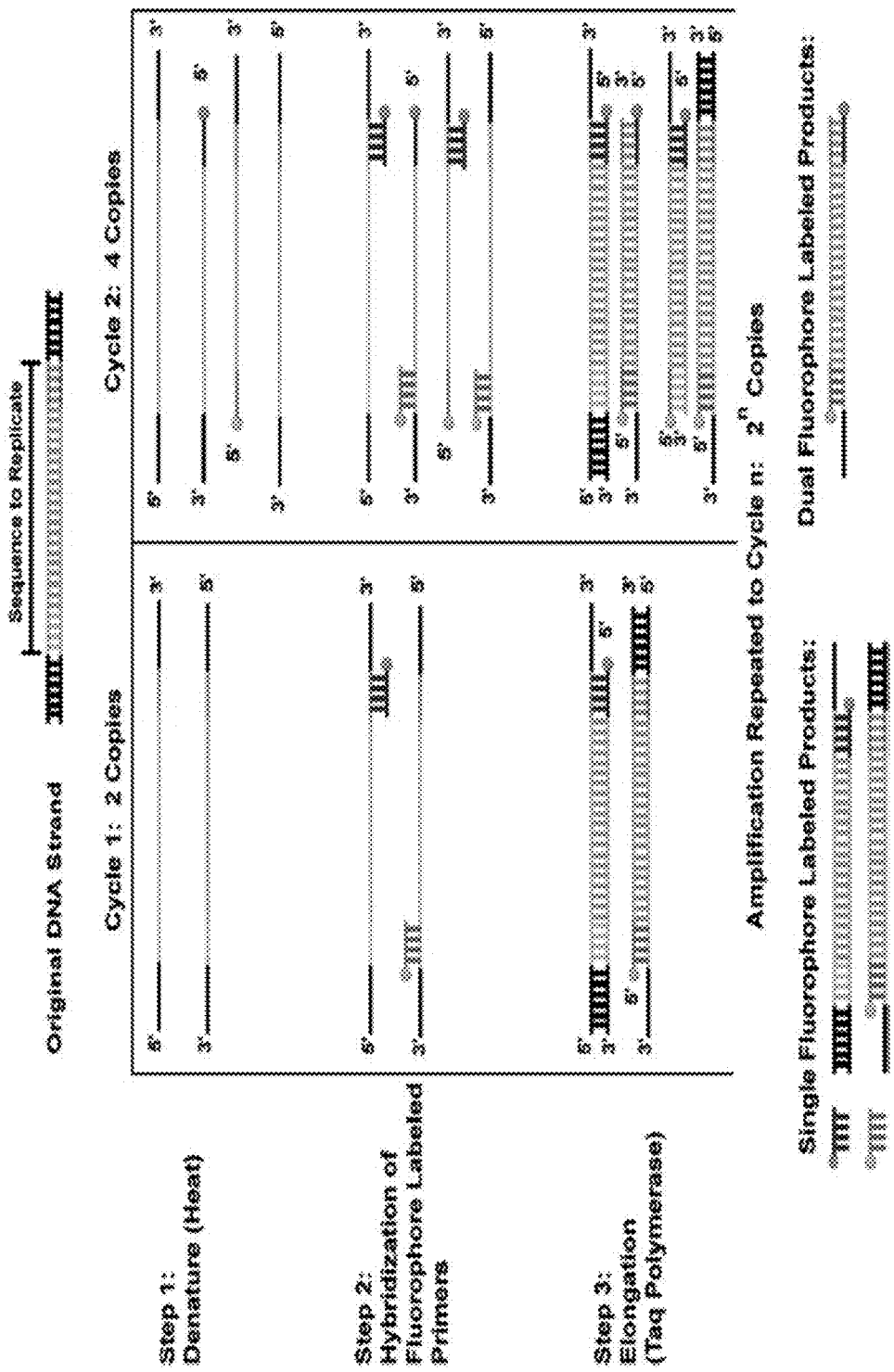
FIG. 8A depicts an experimental method for preparing two color labeled nucleic acid to confer amplicon product identity.
Figure 9A:
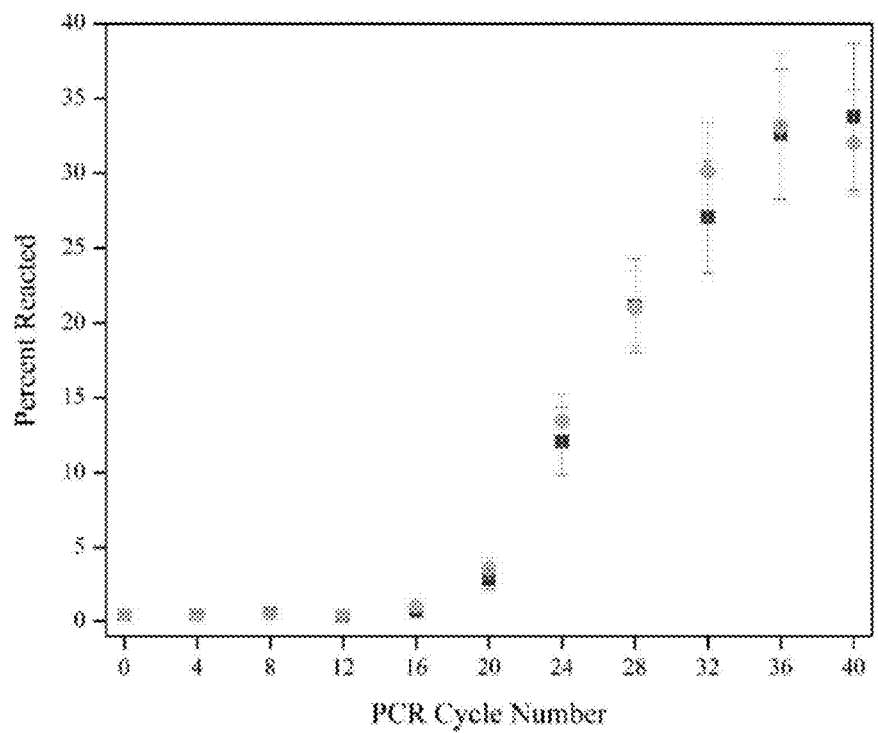
FIG. 9A depicts the percent product as a function of PCR cycle number, measured using single molecule spectroscopy in submicrometer fluidic channels. Light shaded circles and dark shaded squares represent the percent product as a function of green and red primers, respectively. Error bars correspond to one standard deviation.
Figure 9B:
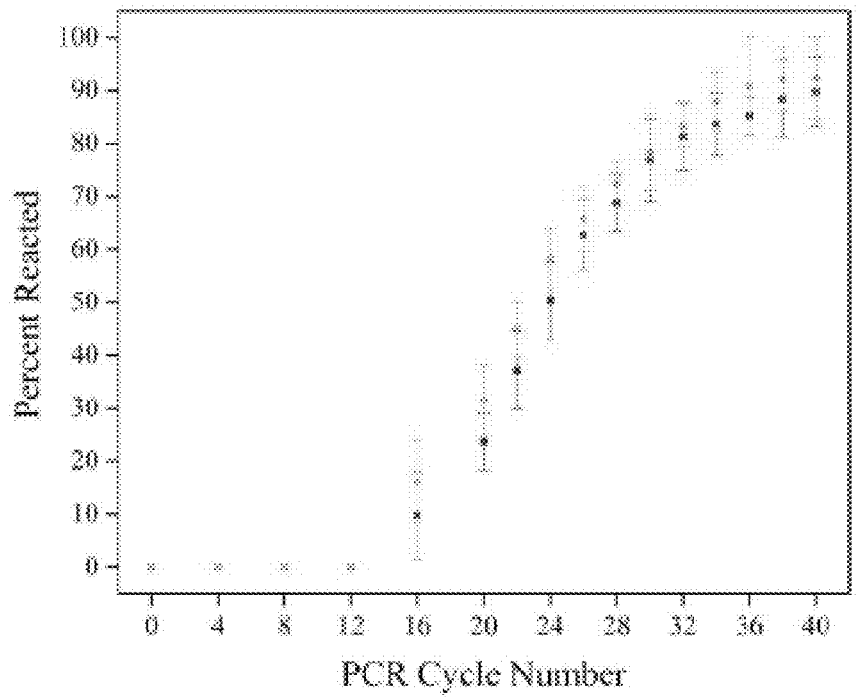
FIG. 9B depicts the percent product as a function of PCR cycle number, measured using a conventional gel electrophoresis method.

Time and color coincident spectroscopy at the single molecule level may have practical application in the study of PCR products. These experiments demonstrate our ability to perform quantitative multicolor analyses, simultaneously, on our devices using DNAs. In this experiment, the purification of the amplicon product normally performed following a PCR reaction is eliminated. Primer molecules can be each labeled with any dyes known in the art, e.g., with either a green (Alexa Fluor 488) or red (Alexa Fluor 594) fluorophore, while amplicon products incorporated both colors, as shown in FIG. 8A. In FIG. 8A, labeled primers are indicated with either a light or dark shaded circle attached to the primer. Isolation and measurement of single molecules permit primers and amplicons to be distinguished in-situ, on the basis of the time and color coincidence. This detection demonstrates the ultimate in sensitivity, single fluorophores attached to single molecules, and at counting rates ~1,000 molecules/min. The ability to detect fluorescence at this level of sensitivity indicates that epigenetic marks can be detected on chromatin fragments with a low density of those marks. Coincidence is studied on samples from every fourth cycle of the PCR reaction, between cycles 0 and 40. The frequency of coincident events is compared against the primer population at each measured cycle and used to recreate the classic PCR amplification curve (FIG. 9). This method can also be applied to nucleic acid samples that have not been amplified.

EXAMPLES

Example 1

A Nanofluidic Platform for Single Molecule Analysis

One strategy for high throughput analysis of single molecules of methylated DNA and chromatin can entail time-resolved detection and spectral identification of fluorescent labels bound to individual molecules containing epigenetic marks of interest. We flowed and detected DNA and chromatin in a solution confined within a nanofluidic channel. These channels reduce the optical excitation volume for fluorescent analysis, thus enabling us to interrogate individual molecules in solutions of relatively high concentration. The nanofluidic channels were fabricated in a fused silica substrate using photolithography and reactive ion etching. FIG. 1C a shows a single nanofluidic channel made by this process with cross-sectional dimensions of approximately 250 nm wide by 500 nm deep. We formed 27 separate fluidic channel arrays, each with 16 parallel channels, on a 100 mm diameter wafer. Each array also had access ports with a reservoir at the ends of the channels, which we used to load the samples and to insert electrodes for controlling electrokinetic flow.

Figure 17:
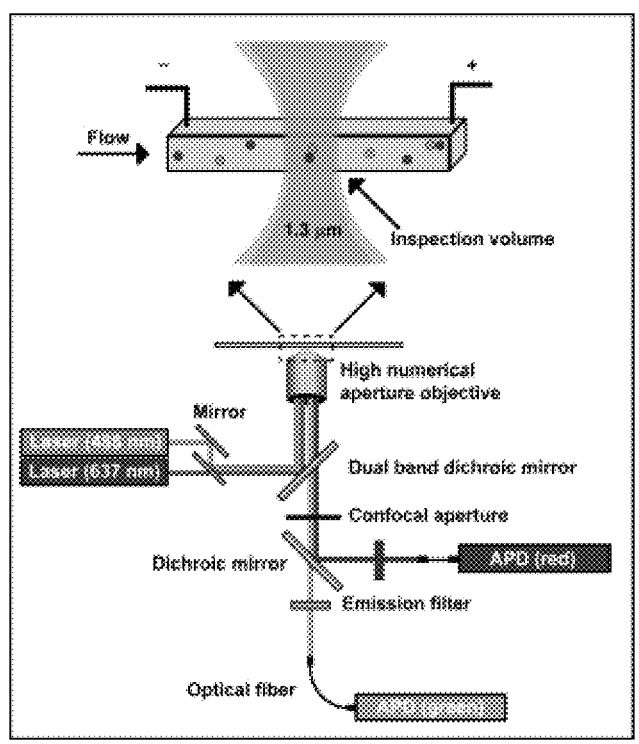
FIG. 17 shows a schematic diagram an experimental platform including a wafer mounted on a confocal fluorescence microscope. Two overlapped lasers illuminated a 1.3 μm length of the nanofluidic channel and formed an inspection volume of 0.16 fL. Collection of the dim, fluorescent signature for each molecule was achieved using a confocal aperture, which spatially restricted the optical collection to the inspection volume, and avalanche photodiodes (APDs), which provided single photon detection.

To analyze individual molecules of DNA and chromatin flowing through channels, we mounted the silica wafer on a laser confocal microscope and illuminated the samples flowing through an individual channel with two overlapping Gaussian shaped laser profiles, each with a diameter of approximately 1.3 μm (FIG. 17). The laser profiles were larger than the channel width, so that every fluorescent molecule was interrogated with the same illumination profile. The illuminated inspection volume within the channel was 0.16 fL. A burst of fluorescence, associated with the different labeled components, was emitted as each molecule passed through the illumination profile. The colors composing a molecule's signature were separated with optical filters and then detected with avalanche photodiode detectors. A record of the red and green fluorescence bursts were accumulated at 100 kHz onto a personal computer and then analyzed with a custom Matlab algorithm to identify single molecule detection (SMD) events.

Example 2

Nucleosome Detection on Native Chromatin

This experiment demonstrates that chromatin can be directed through a nanofluidic channel and remain intact, having nucleosomes remain attached on the DNA. For this test we used chromatin extracted from HeLa cells bearing a transgene expressing an H2B-GFP (green fluorescent protein) fusion protein. H2B-GFP incorporated into nucleosomes allowed the chromatin to fluoresce. We prepared native chromatin from the cells using standard methods, treating isolated nuclei with micrococcal nuclease (MNase) and then extracting the soluble native chromatin using a high salt buffer. We next labeled the DNA within our chromatin preparations with TOTO-3, a red nucleic acid stain that is spectrally distinct from GFP. We wanted to analyze this dual labeled chromatin for two reasons. First, it permitted us to determine whether chromatin remained intact during nanofluidic electrokinetic flow, which is essential for any successful application of this method for epigeneomic analysis. Intact chromatin produce time-coincident TOTO-3 and GFP fluorescent SMD events that indicate DNA and histones are bound. Second, demonstrated that simultaneous, multi-color detection of chromatin were performed at high rates.

Figure 18:
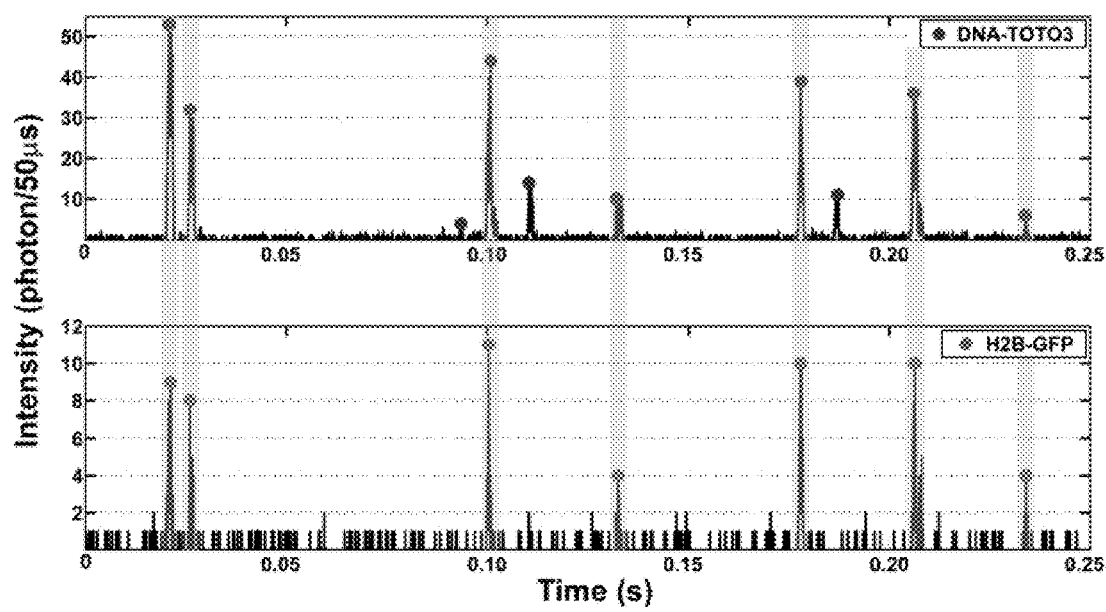
FIG. 18 shows a process of single molecule detection and two-color coincidence analysis. Time-trace record of photon bursts observed by each APD, showing 0.25 seconds of a 15 minute nanofluidic SCAN. A burst with a sum of 10 or more photons satisfied a threshold condition and was designated a single molecule detection (SMD) event, shown here by a circle symbol in the top graph or bottom graph identifying DNA and histone H2B, respectively. Intact chromatin fragments, identified on the graphs with a vertical shaded bar spanning both graphs, were identified by time-coincident detection of both a red and green event.

FIG. 18 illustrates a 0.25 s SCAN using chromatin extracted after a 5 min MNase digestion and then driven through a nanofluidic channel at 50 V. The top panel shows photon bursts corresponding to TOTO-3, which marks the DNA, while the bottom panel shows GFP fluorescence that marks the H2B. In order to identify the single molecule peaks shown (FIG. 18), successive photon arrival times differing by less than 200 µs were grouped as a burst. This time is about one-third that required for a molecule to pass through the inspection volume. Bursts with a total of 10 or more photons were designated as SMD events. The mean noise detected with buffer only was 0.22 photon/50 µs. A velocity of 2.2 mm/s was calculated by fitting a histogram of the time duration (FIG. 21) for TOTO-3 SMD events. Since the sample solution was loaded into the reservoir connected to the negative electrode, only molecules carrying a net negative charge could be driven into the channel. In the pH 8.0 buffer used, only histone-free DNA and intact chromatin carry net negative charge. The net positive charge of individual free histones, each greater than 16.5 at this pH (see Supporting Information), caused them to remain in the loading reservoir. The time-coincident SMD events shown in FIG. 18 are marked by shaded vertical bars spanning the plots, the majority of which are intact chromatin. Accurate identification of dual labeled chromatin was ensured by using optical filters that achieved more than 20 dB of spectral isolation of green GFP bursts from red TOTO-3 bursts, essentially eliminating fluorescence spectrum crosstalk or bleed-through during detection.

Approximately, ninety-three percent of all GFP molecules identified were coincident with a DNA molecule, indicating chromatin remained intact during electrokinetic flow within our nanofluidic device. This degree of coincidence was achieved using TOTO-3 at a 1:5 dye to base pair ratio, which provided the highest fluorescence intensity while not dissociating histones from the chromatin. Additional measurements (Table 2 in Example 15) performed with 1:10 and 1:15 labeling ratios, produced similar levels of coincidence, further demonstrating that this labeling did not dissociate histones. We observed that approximately one-third of the TOTO-3 signals were not coincident with GFP. This population of molecules is expected to arise from undigested and histone-free linker DNA known to exist in the genome, and also from intact chromatin that contained only the endogenous unlabeled H2B; half of the H2B in the cells is made from the GFP fusion transgene.

Figure 19A:
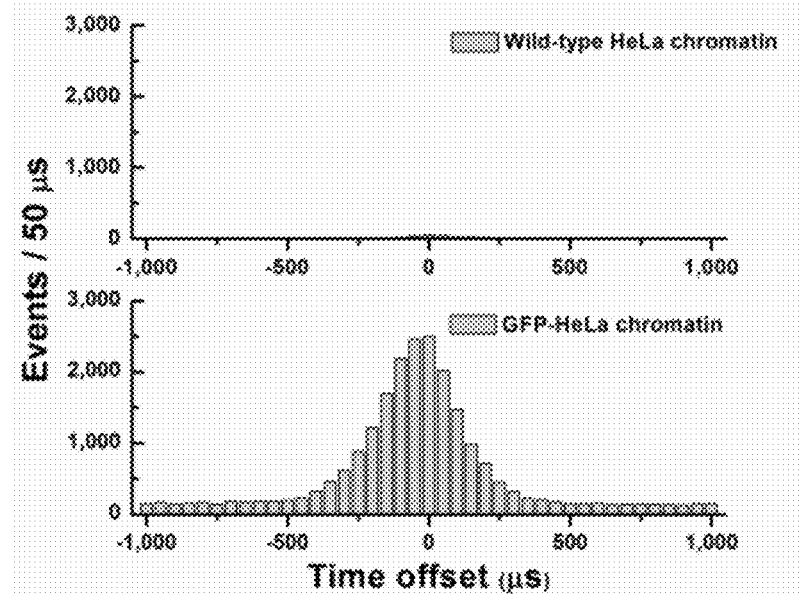
FIG. 19A and FIG. 19B show an exemplary nanofluidic SCAN of GFP-HeLa chromatin at different digestion times. Chromatin was isolated from the nuclei of wild-type HeLa cells and HeLa cells with a H2B-GFP fusion transgene and then analyzed by SCAN for 15 minutes.
Figure 19B:
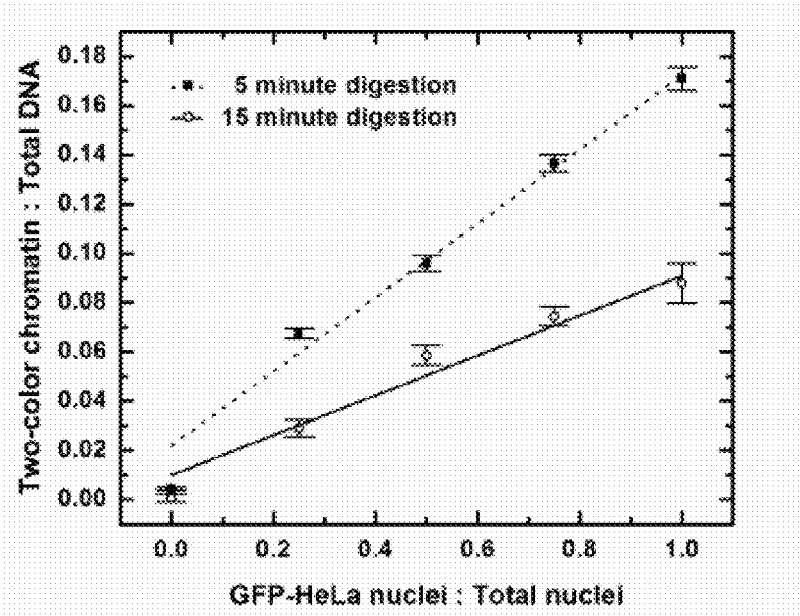

To further test the authenticity of chromatin detection using SCAN, we prepared chromatin from mixtures of nuclei from wild-type HeLa cells and HeLa cells with the H2B-GFP transgene, maintaining a constant total cell quantity for all mixtures. We anticipated that the rate of coincidence should drop with increasing amounts of wild-type chromatin, yielding fewer fragments with H2B-GFP. Fragments from each mixture were then detected by SCAN to determine the fraction of two-color labeled chromatin present in each mixture. We compiled (FIG. 19a) a record of all coincident SMD events observed during a period of 15 min using a time coincidence histogram (TCH). The TCH contains the time-offset between all identified GFP events and TOTO-3 events within a fixed time window. The area under the peak and above the background level, describes the total chromatin fragments with H2B-GFP, which increased with the proportion of GFP-HeLa nuclei. We found the proportion of chromatin fragments with H2B-GFP to exhibit a linear increase with GFP-HeLa proportion for both the 5 and 15 min digestion series (FIG. 19b). The direct proportion between chromatin fragments with H2B-GFP and input of GFP-HeLa nuclei validates the authentic detection of chromatin. Note that the slopes differ for the two digestion times with the prolonged digestion producing a smaller slope. The coincidence per DNA was principally reduced due to an increase in mononucleosome fragments and linker DNA fragments produced at longer digestion times, for a constant number of H2B-GFP nuclei within a mixture. This trend was also consistent with other chromatin preparations, wherein longer fragments demonstrated a higher coincidence proportion.

Figure 8B:
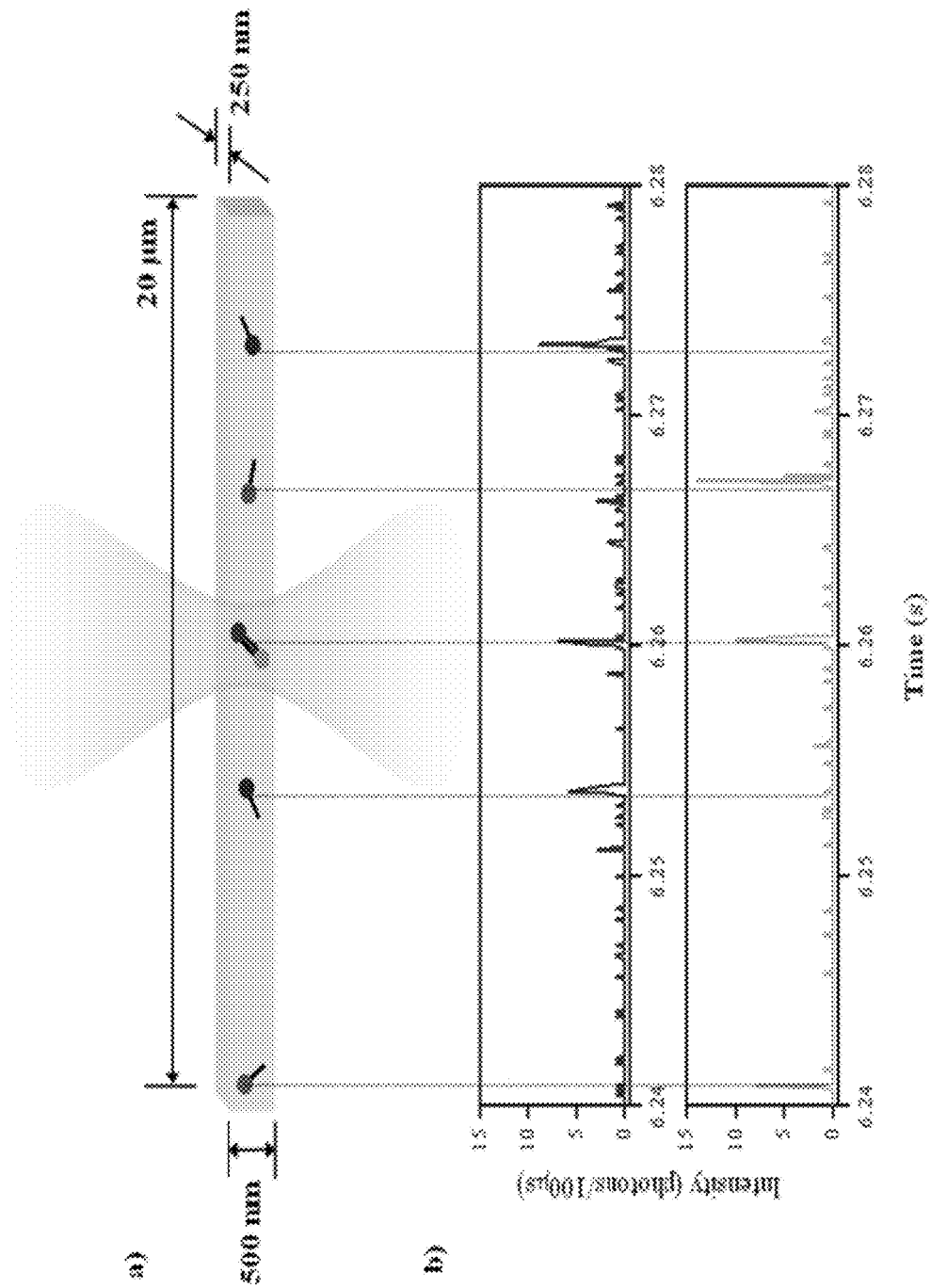
FIG. 8B depicts an experimental time trace showing unpurified PCR reaction content used in detection with both color primers and amplicon products detected separately at the single molecule level. Extreme detection sensitivity is demonstrated using a single fluorophore of a given color attached to each molecule.
Figure 23:
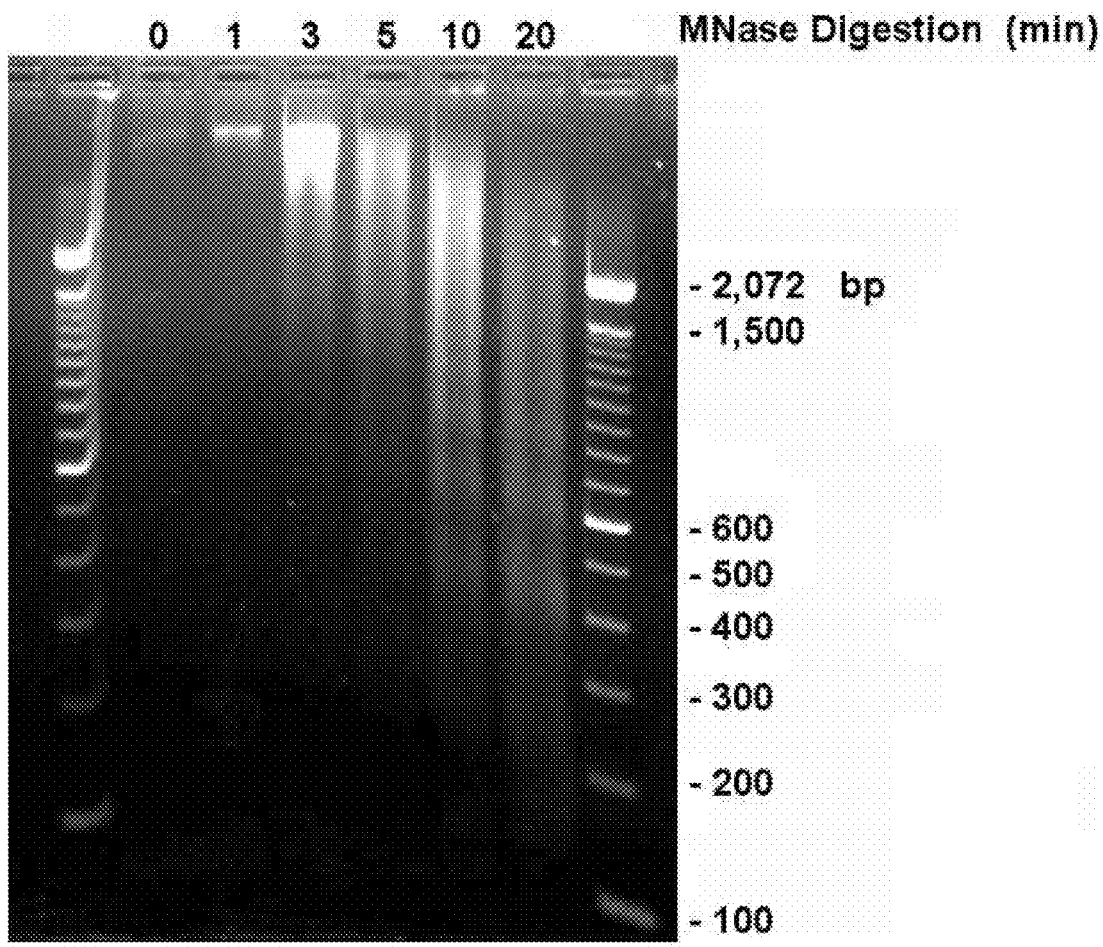
FIG. 23 is a gel showing chromatin fragments prepared during different batches of MNase digestion.
Figure 24:
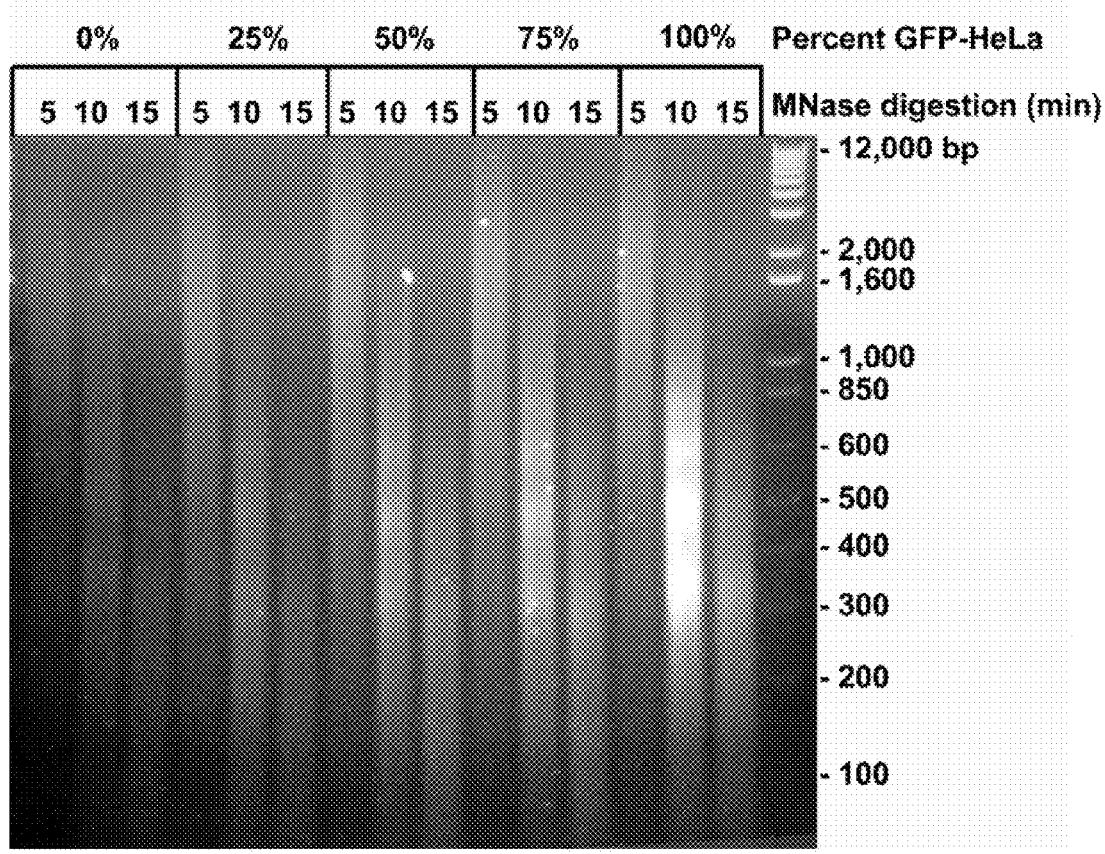
FIG. 24 is a gel showing chromatin fragments prepared during different batches of MNase digestion.

We observed variation in the size of chromatin fragments prepared during different batches of MNase digestion. For example, GFP-HeLa chromatin extracted after a 5 min MNase digestion, but prepared from different batches of GFP-HeLa cells on separate dates yielded different fragment sizes, as verified by gel electrophoresis (FIGS. 7 and 8). We attribute this to variation in MNase activity. As a result, nanofluidic SCAN detected a 93% coincidence per GFP for samples with a median fragment size above 2 kbp (5 min lane in FIG. 23); while 50% coincidence per GFP was observed for samples with a median fragment size less than 2 kbp (100% GFP, 5 min lane in FIG. 24). Further SCAN with chromatin digested to less than 1 kbp fragments (100% GFP, 15 min lane in FIG. 24) demonstrated 35% coincidence per GFP. The variation, if it occurs for shortened may be mitigated using a different fluorescent labeling method, extending SCAN to the study of short nucleosome fragments.

Figure 22:
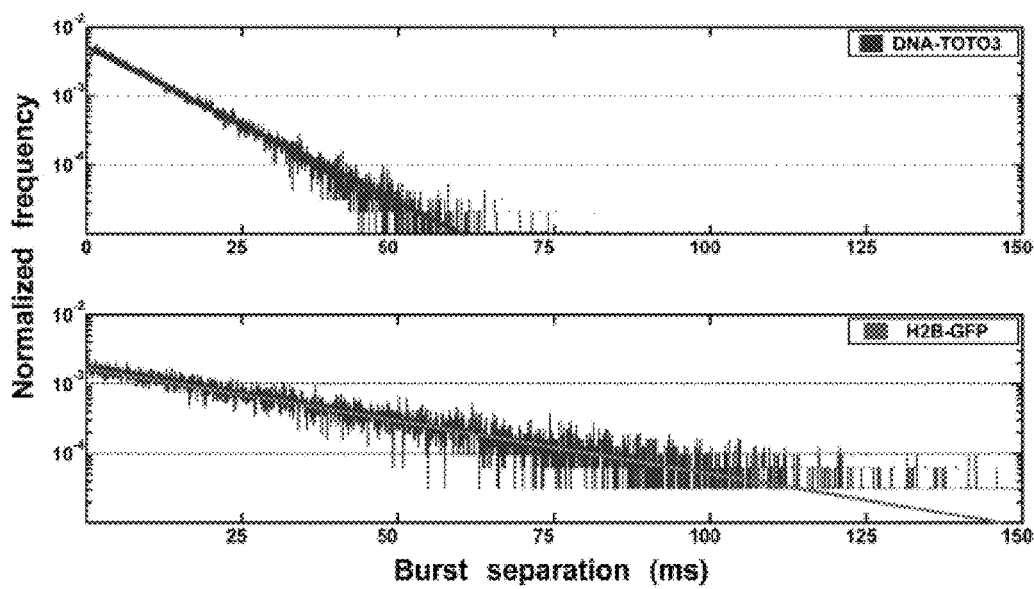
FIG. 22 shows a burst separation graph for separate fluorescent dye colors.

To evaluate the throughput of our nanofluidic device (Table 1), we utilized SCAN measurements of the 5 and 15 min digestions of 100% GFP-HeLa nuclei. The rates for SMD of both DNA and H2B were averaged over 15 min of analysis. We calculated the detection rate for time-coincident molecules of dual-labeled chromatin by performing a background-corrected TCH analysis for each minute of SCAN. The throughput for all molecule types was consistently higher for chromatin from the 5 min digest, as compared to the 15 min digest, and suggested a higher sample concentration. We verified this observation in-situ by fitting a histogram of the time between each SMD event of a given color with an exponential model to calculate the sample concentration (FIG. 22). The average fragment size was estimated separately using gel electrophoresis (FIGS. 7 and 8) and then combined with the DNA detection rate to derive the analysis throughput.

TABLE 1

Nanofluidic SCAN Throughput for 100% GFP-HeLa Samples

| MNase Treatment (min) | 5 | 15 |
|---|---|---|
| DNA Concentration (pM)[b] | 588 ± 8 | 248 ± 2 |
| Dual-Labeled Chromatin (molecules/min)[a] | 1067 ± 114 | 201 ± 36 |
| H2B (molecules/min)[a] | 2116 ± 143 | 568 ± 67 |
| DNA (molecules/min)[a] | 6238 ± 611 | 2287 ± 184 |
| Gel Estimated Average Fragment Size (bp)[c] | 1600 | 500 |
| DNA Throughput (Mbp/min)[d] | 10 | 1 |

[a]Analysis for a 15 minute SCAN at an electrokinetic drive of 50 Volts.
[b]DNA concentration measured in-situ based upon the time between SMD events
[c]Fragment size estimated by gel electrophoresis
[d]DNA detection rate and estimated fragment size are used to calculate DNA throughput.

Example 3

Detection of DNA Methylation

Figure 25:
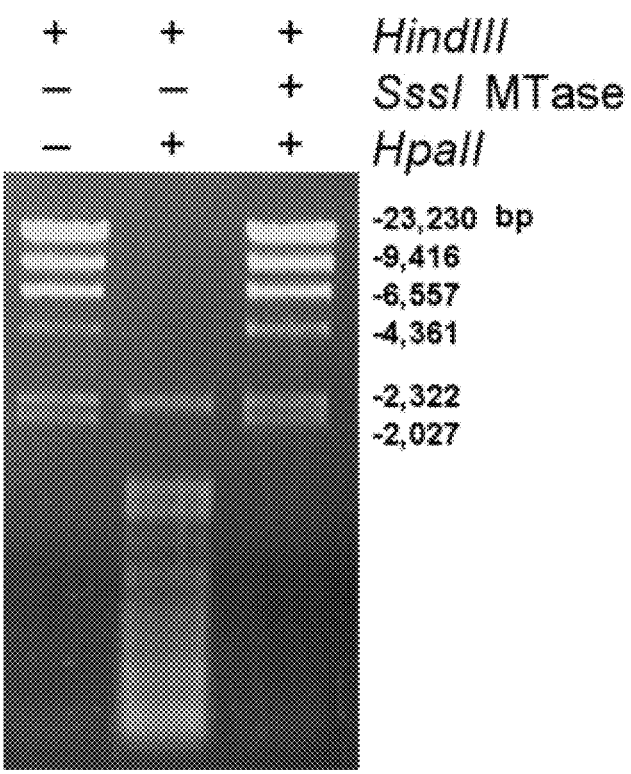
FIG. 25 is a gel showing effectiveness of methylation reactions following DNA digestion with the methylation sensitive restriction enzyme HpaI.
Figure 26:
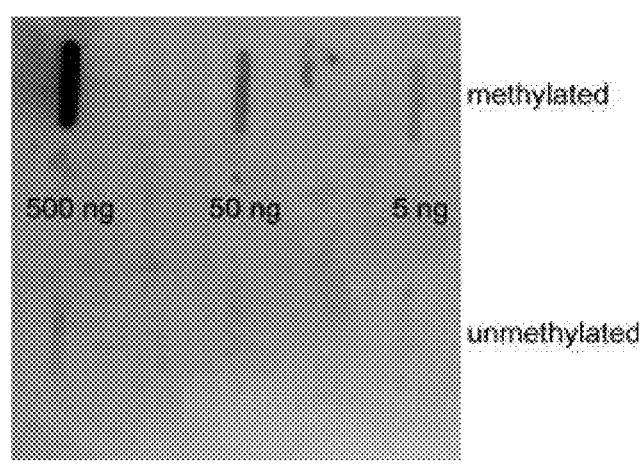
FIG. 26 is a gel showing that the Alexa Fluor 488 labeled MBD1 retained its specificity for methylated DNA.

Probes that have been used in epigenomic analysis were used to detect an epigenetic mark on our nanofluidic platform. We analyzed DNA methylation and used MBD1 as our probe, which has been shown to bind methylated DNA specifically. Our test material was HindIII digested lambda DNA from a methylation deficient host, which we left unmethylated, or methylated in vitro using SssI DNA methyltransferase. SssI can methylate all 3,113 CpGs in the 48.5 kbp genome. We verified the effectiveness of the methylation reactions by digesting the DNA with the methylation sensitive restriction enzyme HpaI (FIG. 25). Both DNA samples were stained with TOTO-3 and incubated with MBD1, which we labeled with Alexa Fluor 488. Alexa Fluor 488 is spectrally similar to GFP. The Alexa Fluor 488 labeled MBD1 retained its specificity for methylated DNA (FIG. 26). To facilitate optimum binding to methylated DNA, we added a molar excess of MBD1 to the stained DNA. We found that dilution of this mixture into our 1×TBE-based buffer resulted in stable electrokinetic flow, as indicated by consistent SMD rates and low-levels of non-specific interaction between probes and the nanofluidic structure.

Figure 20A:
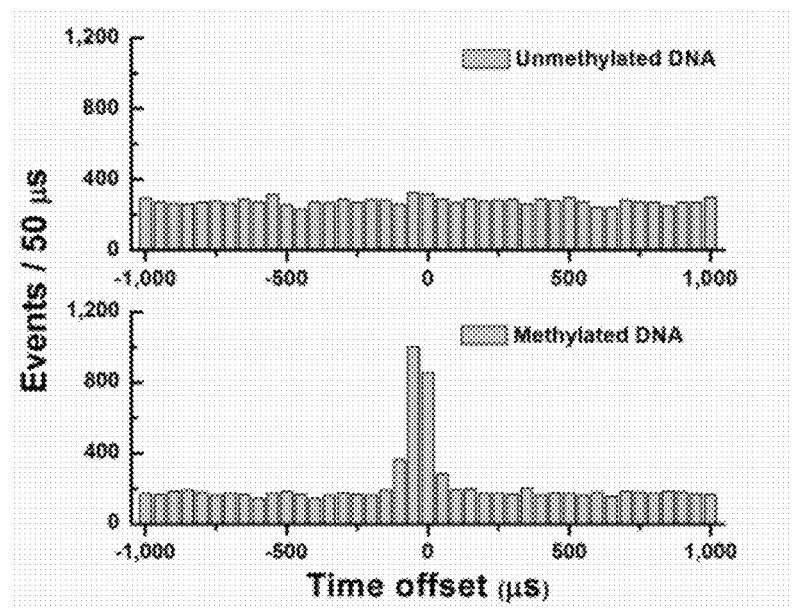
FIGS. 20A and 20B shows detection of DNA methylation.

FIG. 20a illustrates the number of coincident SMD events for MBD1 mixed with unmethylated DNA (top panel) or methylated DNA (bottom panel). Each mixture was analyzed for 15 min at applied potential of 100 V. The background level of coincidence events in the unmethylated DNA sample was due to an excess of probe present in the mixture. However, the central Gaussian peak in the methylated DNA sample showed that bound MBD-DNA complexes were detected above the high background. Where desired, fine tuning the subject methods can be done by incorporating other methods known in the art to reduce background signal from free fluorescent probes.

Figure 20B:
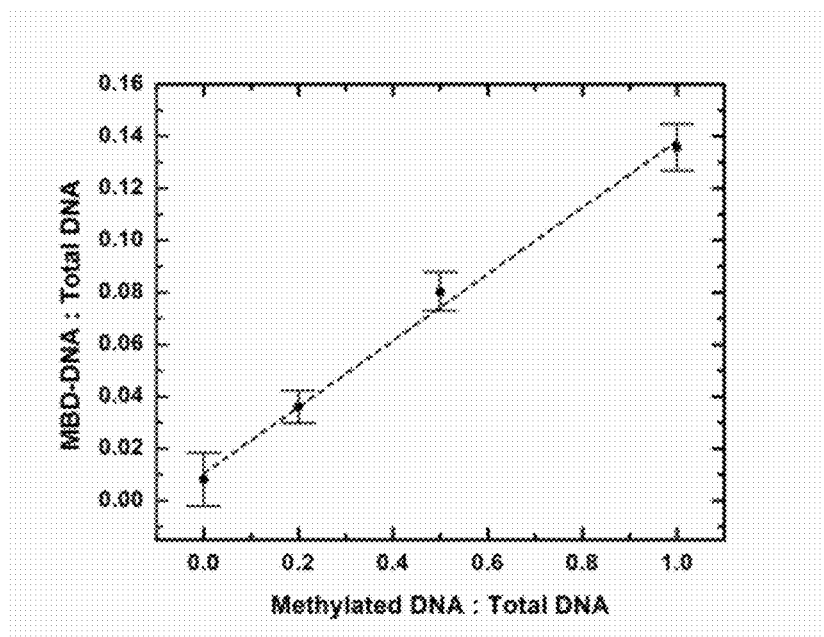

Similar to the chromatin analysis, we verified the authenticity of these detection events. We prepared a dilution series of methylated and unmethylated DNA. We expected that with diminishing amounts of methylated DNA, we should observe a diminishing frequency of coincident events. This is consistent with our observed results (FIG. 20b). There was a linear increase in the number of MBD-DNA complexes with increasing methylated DNA concentration, verifying the specificity of the signals detected by MBD1, and demonstrating the utility of nanofluidic SCAN for detecting epigenetic marks on individual molecules.

We have described the development of SCAN using a nanofluidic platform to analyze individual molecules using the same fluorescently labeled probes that have been used in bulk epigenetic analysis in molecular biology. Confinement using nanofluidic channels allowed for single molecule analysis to be performed within the 100-1000 pM concentration range, which was essential for maintaining chromatin structure. We verified through multi-color SCAN that core histone octamers remained bound as nucleosomes within this nanofluidic environment during electrokinetic flow. Dilution of wild-type HeLa and GFP-HeLa nuclei was used to confirm the authenticity of coincidence detection. We observed chromatin fragments with a throughput of about 10 Mbp per minute using a single fluidic channel, indicating we could SCAN the entire genome of a fungal model organism in as few as eight minutes. We envision scaling our current throughput using parallel and/or radial arrays with tens or hundreds of fluidic channels to perform analysis of larger organisms. For example, using 10 fluidic channels would allow 1× coverage of a 3 Gbp human genome to be scanned in just 30 minutes.

Further reduction of the nanofluidic channel cross-section would allow for SMD at higher concentrations and increase the signal to noise ratio for single molecule fluorescent analysis. Since the probability of detecting a coincident event randomly is related to the sample concentration in the inspection volume, this probability can be engineered by reducing the channel cross-section. With sufficiently narrow channels the flowing chromatin or DNA molecules can be elongated allowing multiple fluorescent labels to be spatially separated and resolved. This may permit molecular mapping with spatial resolution sufficient to identify multiple epigenetic marks on a single nucleosome or to distinguish marks on adjacent nucleosomes. Prior work has shown optical resolution of molecular length to 114 nm, equivalent to about 335 bp, during rapid flow of lambda DNA. This spatial resolution was possible using nanofluidic channels with cross sectional areas on the order of 0.01 $\mu m^2$, an order of magnitude less than was used in these experiments. It is likely that smaller channels will allow us to identify molecules with multiple bound probes and resolve their positions on a chromatin fragment.

Example 4

Calculation of Histone Charge

The amino acid sequence for each of the four core histones were entered into the online calculator available from www.scripps.edu. This solver provided the charge for each core histone at various pH values and 16.5 was the smallest positive charge associated with a free histone at pH 8.0.

Example 5

Preparation of HeLa Cell Chromatin

HeLa cells constitutively expressing green fluorescent protein on histone H2B (H2B-GFP) were cultured as monolayers in Dulbecco's modified Eagle's medium (DMEM) supplemented with 5% fetal calf serum. Native chromatin fragments were prepared from HeLa cells as follows:

Briefly, cells from two 15 cm plates were scraped and washed once with 1×RSB (10 mM Tris pH 7.6, 15 mM NaCl, 1.5 mM $MgCl_2$), resuspended in 5 mL 1×RSB buffer with 1% Triton-X 100 and homogenized using a Dounce homogenizer fitted with a loose pestle using eight strokes. Nuclei were recovered by centrifugation, resuspended in 1.5 ml Buffer A (15 mM Tris pH 7.6, 15 mM NaCl, 60 mM KCl, 0.34 M Sucrose, 0.5 mM Spermidine, 0.15 mM Spermine, 0.25 mM PMSF and 0.1% β-mercaptoethanol), to which we added 15 µL 0.1 M $CaCl_2$ and 1.5 µL of micrococcal nuclease (3 units/µL) and incubated for various times, using 5 µL of 0.5 M EDTA to stop the digestion. Digests were centrifuged, the supernatants discarded, and each 140 µL aliquot of nuclei were resuspended in 450 µL 10 mM EDTA, 50 µL 5 M NaCl to solubilize the chromatin. Soluble chromatin was separated from the insoluble debris by centrifugation. For gel analysis of DNA, we took 60 µL of chromatin, added 24 µL $H_2O$, 6 µL 10% SDS and 24 µL 5 M NaCl, then extracted DNA with a 1:1 mixture of phenol-chloroform and 10 µL supernatant was analyzed by 1.5% agarose gel electrophoresis. We used a fluorimeter to measure the fluorescence of the intact chromatin and a spectrophotometer to measure the amount of DNA extracted from the chromatin. This served to calibrate the fluorimeter reading, allowing direct estimation of the sample concentration during subsequent chromatin isolation preparations without removing histones. The calibration was reproducible between preparations.

Probe selection and labeling can be fundamental to SMD. Our initial attempts to detect chromatin signatures used antibodies. Because they have two antigen binding sites, a single antibody molecule can cross-link two chromatin fragments. At antigen and antibody concentrations that allow the classical precipitin reaction, aggregates form, which can clog the nanofluidic channel. This can be avoided by using vast antibody excess, or monovalent probes for epigenetic marks including Fab fragments of antibody, aptamers, or monovalent probes such as the MBD1 protein we used carrying a single methyl binding domain.

Example 6

Methyl Binding Domain (MBD1) Protein Synthesis and Labeling

Plasmid for bacterial expression of 1×MBD (pET-1× MBD) was provided by Adrian P. Bird at The Wellcome Trust Centre for Cell Biology, University of Edinburgh, UK. Recombinant His6-tagged MBD1 was purified from 100 mL induced BL21(DE3) cultures on Ni-NTA agarose (Qiagen) using denaturation and on column renaturation cycles in accordance with the manufacturer's instructions, with some modifications.

The methylation sensitive binding domain (MBD) from MBD1 was cloned into the pET-30b plasmid in order to create a His-tag fusion protein that was expressed under IPTG induction. IPTG induced E. coli were lysed and the fusion protein was purified and refolded on a nickel column. Following purification the fusion protein was labeled with Alexa 488 using Invitrogen's microscale labeling kit (A30006), which labels free amines. Three additional rounds of resin purification were preformed to better purify away free labels. The integrity of the labeled MBD probe was assayed with a slot-southwestern blot (FIG. 26). Though absorbance measurements indicated an average degree of labeling of 1.5 dye per MBD, we believe that three subpopulations remained within the labeled mixture: dye-labeled MBD, free unbound dye, and MBD with no dye. If three subpopulations exist within the dye-labeled MBD solution, the number of bound MBD-DNA complexes would be under-reported.

Example 7

Lambda DNA Preparation and In-Vitro Methylation

Lambda DNA from phage grown in a methylation deficient host (Promega D1521) was digested with HindIII and methylated in vitro with SssI methyltransferase, which can methylate all 3,113 CpGs in the 48.5 kbp genome. Efficacy of the methylation reaction was assessed by resistance to digestion by the methylation sensitive enzyme HpaII.

Example 8

MBD-DNA Affinity Reaction

In a mixture of methylated and unmethylated DNA suspended at 50 ng/μL in 1×Tris Buffered Saline (1×TBS, 50 mM TRIS-HCl and 138 mM NaCl and 2.7 mM KCl, pH 8.0), we performed DNA staining using TOTO-3. Approximately 1 μg of labeled DNA was then diluted into 20 μL of buffer containing 1×TBS with 2% bovine serum albumin and 0.1% TritonX-100 (v/v). A volume of 1 μL MBD1, stored at 280 ng/μL, and labeled with AlexaFluor488 was then added to the DNA to perform the binding reaction under conditions of molar excess. The binding reaction occurred for 2 hours at room temperature.

Example 9

DNA Labeling

We use the cell-impermeant, intercalator TOTO-3 (Invitrogen). The labeling reaction was conducted by mixing the diluted DNA or chromatin and the diluted dye according to the method described by the manufacturer. All samples were prepared with a 1:5 dye to base pair ratio, unless otherwise noted. Following the labeling reaction, samples were protected from light and stored overnight at 4° C. TOTO-3 exhibits significant fluorescence enhancement upon binding, which alleviated the need for purification to remove unbound dye following the labeling reaction.

Example 10

Fabrication of Nanofluidic Channels

Nanofluidic channels were fabricated in a fused silica substrate. Projection photolithography (GCA Autostep 200) was used to pattern fluidic channels with a 500 nm critical dimension. This method allowed rapid patterning of 27 fluidic channel arrays, totaling 432 fluidic channels, on a 100 mm diameter wafer. Patterns formed in the developed photoresist were transferred approximately 250 nm into the silica using reactive ion etching (Oxford 80, Oxford Instruments). The fluidic channels were protected with photoresist during subsequent through-wafer drilling using a focused jet of alumina abrasive to form the access ports at the ends of the channels. The wafer surface was cleaned with a hot Piranha solution ($3H_2SO_4:1H_2O_2$) and RCA standard clean ($5H_2O:1\ NH_4OH:1H_2O_2$, heated to 70° C.).

Direct touch bonding with a 170 μm thick coverslip wafer was performed to cap the fluidic channel. A subsequent high-temperature anneal to 1050° C. permanently bonded the stack of fused silica wafers together. An optical-grade epoxy (Norland Products) was used to attach fluid reservoirs to the wafer surface.

Example 11

Electrokinetic Flow in Nanofluidics

Samples were kept in their respective storage buffer until DNA labeling and/or MBD binding reactions. Following these reactions, samples were serially diluted in 1×Tris-Borate-EDTA (1×TBE, 89 mM TRIS borate and 2 mM EDTA, pH 8.0), with additives 0.5% polyvinylpyrrilidone (PVP) measured (w/v) and 0.1% TritonX-100 measured (v/v) (both from Sigma Aldrich, St. Louis, Mo.). The final dilution suspended the samples at an estimated concentration of 600 pM, nominally 1-2 ng/μL for chromatin samples, and about 0.25 ng/μL for methylated DNA samples. The polymer additives in the buffer served to limit electroosmotic flow and prevent non-specific interactions with the fluidic channel walls without denaturing proteins. We loaded 50 L of the sample solution into the input reservoir of a fluidic channel array and then connected to the negative electrode. The output reservoir contained only the buffer solution and was connected to the positive electrode. Samples were flowed at an applied bias of 50 V for all chromatin samples and 100 V for all methylated DNA samples. Stable electrokinetic flow was established during a pre-flow time of 20 min to ensure steady-state flow conditions had been achieved prior to data collection. Each sample was examined for a total of 15 min, always using the same fluidic channel within the array. Following single molecule detection, the fluidic channel array was rinsed iteratively for a total of 30 min and then checked to verify the absence of fluorescently-labeled molecules, prior to loading the next sample. Fluid channel arrays used with chromatin experiments were not reused with DNA methylation experiments.

Example 12

Laser Induced Fluorescence Confocal Microscopy

Single molecule fluorescence was observed using an inverted microscope (IX-71, Olympus) equipped with a side laser port. Laser illumination of 330 μW at 488 nm (Sapphire, Coherent) and 1300 μW at 635 nm (Cube, Coherent) were overlapped in free-space, incident on a dual-band dichroic mirror (488/647rpc, Chroma Technology) and then focused onto the nanofluidic channel using a 60×, 1.2 numerical aperture water-immersion objective (UPlanSAPO, Olympus), and aided with an electron multiplied CCD camera (Cascade 512B, Photometrics). A dual-band laser notch filter (NF01-488/647, Semrock) attenuated stray laser light and passed single molecule fluorescence. Confocal spatial filtering occurred using a 50 μm diameter pin-hole (901PH, Newport). Two color fluorescence was then chromatically split using a second dichroic mirror (FF560-Di01, Semrock) and then filtered by band pass fluorescence filters (525/50M and 680/40M, Chroma). Each color of fluorescence was then collected using a 100 μm diameter core multimode optical fiber (OZ Optics). Photons were detected by avalanche photodiodes (APD) in single photon counting mode (SPCM, Perkin-Elmer) and recorded at 100 kHz using a high-speed correlator (correlator.com) and a personal computer.

Example 13

Statistical Analysis

Propagated error analysis was performed to evaluate the proportion of bound molecules, chromatin or MBD-DNA, with respect to total DNA. First, we defined a window region that encompassed the full width of the Gaussian distribution in a time coincidence histogram. Adjacent to the window region were the sidebands, which were used to characterize the background of uncorrelated molecules. The background contribution in the window region was calculated based upon the uncorrelated molecules per 50 μs bin in the sidebands, reported as the mean and standard deviation, and then scaled by the number of bins within the window region. The total molecules counted within the window region was summed and reported with a Poisson counting error. The number of bound molecules was then calculated by subtracting the total molecules from the background molecules within the window region and propagating the error. Second, the number of total DNA molecules observed was counted and reported with a Poisson counting error. The ratio of bound molecules and total DNA molecules was then calculated and the errors of each were propagated. As applicable, we plotted the average value and error bars that represented the propagated error.

Fitting error analysis was performed to measure the concentration of molecules measured within a nanofluidic channel. The inter-event time separation was plotted as a histogram and then fitted to single-term exponential decay using Matlab's built-in fitting routine. The fitted mean inter-event time was calculated with a 95% confidence interval. The mean and confidence interval were then evaluated using a Poisson model, to describe molecule occupancy within the inspection volume, to report concentration values.

Example 14

Calculation of Burst Duration and Molecule Velocity

An applied voltage created an electric field within the nanofluidic channel that transported the charged molecules through the inspection volume. The burst duration describes the transit time for a molecule to pass through the inspection volume. Here we examine the burst duration for chromatin molecules prepared with a 5 min MNase digestion from 100% GFP-HeLa nuclei and driven through a channel at 50 V. This data is a subset of those shown in FIG. 19 and was prepared from the chromatin preparation shown in FIG. 24. The burst duration (t) for each fluorescent dye color was examined separately and then fitted with a Gaussian model with free parameters μ, for the mean burst duration, and σ, corresponding to standard deviation in the burst duration. The fitted, mean burst duration is provided on each plot with a 95% confidence interval. The Gaussian model used was:

$$f = \frac{e^{-\left(\frac{t-\mu}{\sigma\sqrt{2}}\right)^2}}{\sqrt{2\pi\sigma^2}}$$

Given the approximate laser beam diameter ($x_{laser}$) of 1.3 μm and the mean burst duration ($t_{burst}$) of 585 μs and 495 μs for the DNA and H2B molecules, respectively, we calculated a mean velocity of 2.2 mm/s and 2.6 mm/s using $$v = \frac{x_{laser}}{t_{burst}}.$$

Figure 21:
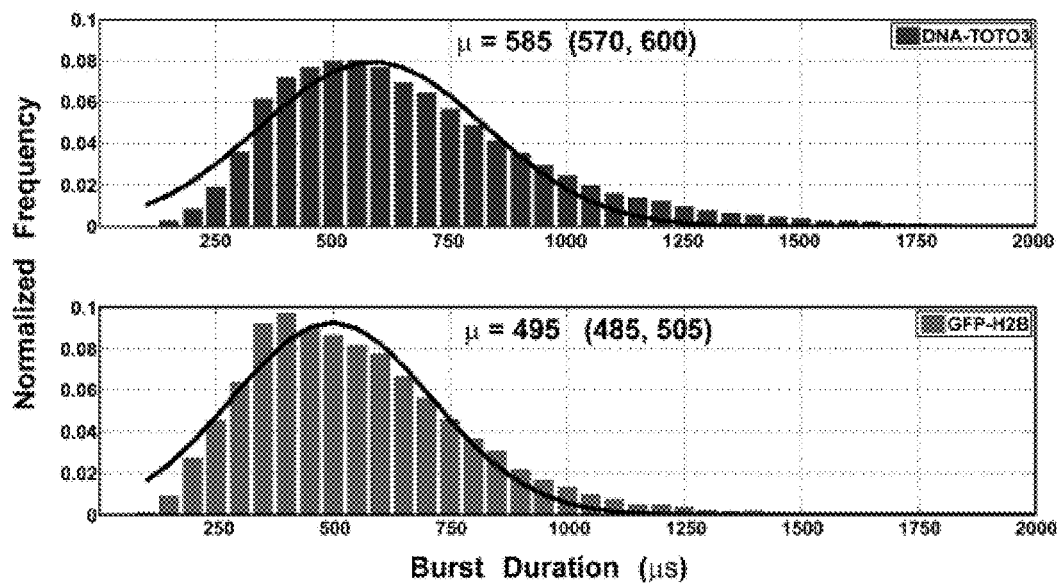
FIG. 21 shows a histogram of time duration of TOTO-3 SMD events.

See also FIG. 21.

Example 15

Intercalator Effects on Nucleosome Integrity

The red DNA stain, TOTO-3, was added to GFP-HeLa chromatin in varying labeling ratios to examine the effects of intercalation on nucleosome integrity. Chromatin prepared with a 5 min MNase digestion (FIG. 23) was diluted to approximately 1 ng/μL and driven at 50 V through a nanofluidic channel. We used SCAN to analyze the number of DNA molecules labeled with TOTO-3 and the number of H2B molecules labeled with GFP for three different labeling ratios, 1:5, 1:10, and 1:15 dye to base pair. The results are shown in Table 2 below.

TABLE 2

SCAN analysis of DNA molecule labeling

| TOTO-3 Labeling | DNA-TOTO3 Molecules | H2B-GFP Molecules | Coincident Molecules | Coincident Molecules:DNA | Coincident Molecules:H2B |
|---|---|---|---|---|---|
| None | 2678 ± 52 | 21828 ± 148 | 1128 ± 122 | 0.421 ± 0.0462 | .052 ± 0.00560 |
| 1:15 | 36349 ± 191 | 11569 ± 108 | 9604 ± 431 | 0.264 ± 0.0526 | .830 ± 0.0381 |
| 1:10 | 105381 ± 325 | 37372 ± 193 | 32168 ± 1232 | 0.305 ± 0.0117 | .861 ± 0.0333 |
| 1:05 | 41898 ± 205 | 15819 ± 126 | 14803 ± 325 | 0.353 ± 0.00795 | .936 ± 0.0219 |

We observed approximately 93% coincidence for the 1:5 labeling ratio, which is recommended by Invitrogen for proper intercalation. At the 1:10 and 1:15 labeling ratio, we observed a slightly reduced level of coincidence due to the reduced intercalation efficiency. Since all samples were examined in the same fluidic channel and the TOTO-3 labeled samples were examined first, we observed a small level of TOTO-3 adsorption to the fused silica surface of the channel. This adsorbed dye was subsequently collected by unstained chromatin and resulted in a 5.2% coincident detection rate.

Example 16

Calculation of Burst Separation and In-Situ Sample Concentration

For the dilute sample concentrations used in these experiments, we were able to track the burst separation. The burst separation describes the time elapsed between bursts and is related to the concentration of the sample analyzed. Here we examined chromatin molecules prepared with a 5 min MNase digestion from 100% GFP-HeLa nuclei and driven through a channel at 50 V. This data is a subset of those shown in FIG. 19 and was prepared from the chromatin preparation shown in FIG. 24. The burst separation (t) for each fluorescent dye color was examined separately and then fitted with an exponential model with free parameters $\beta$, $\lambda$. The fitted, mean burst separation is provided on each plot with a 95% confidence interval. The exponential model used was:

$$f = \beta e^{-\lambda t}$$

where $A = CAv$

The data is shown in FIG. 22. In this model, $\beta$ is a scaling factor. The fitted parameter $\lambda$ was related to 'A' is the cross-sectional area of the channel (0.125 µm²) and 'v' is the flow speed of the molecules to calculate 'C', the concentration of molecules. The flow speed was derived using the methods outlined with FIG. 21, which resulted in an in-situ measured concentration of 588±8 pM for the DNA and 248±2 pM for the H2B, as given in Table 2.

Example 17

DNA Fragment Sizing by Gel Electrophoresis

Chromatin was extracted from HeLa nuclei and digested using MNase. With increased duration MNase treatment, we observed a decrease in chromatin fragment sizes, as verified by gel electrophoresis. Batch-to-batch variations in preparation, attributed to MNase activity, resulted in different range of fragment sizes for the same digestion time. For example, we observed the 5 min digestion (FIG. 23) to yield fragment lengths well-above the 2,072 bp marker. However, a series of digestions performed on a later date (FIG. 24) yielded a more disperse range of fragments, nominally centered between 1-2 kbp.

Example 18

In-Vitro DNA Methylation Test with HpaII

Lambda DNA prepared from phage grown in a methylation deficient host (Promega D1521) was left unmethylated or methylated in vitro with SssI methyltransferase. As a test for efficacy of the methylation reaction, aliquots of DNAs were then digested with HindIII or with both HindIII and the methylation sensitive enzyme HpaII. Resistance to digestion by HpaII is evidence for DNA methylation. Base pair sizes of HindIII fragments are shown in FIG. 25.

Example 19

Southwestern Blot Analysis of MBD-1 Activity and Methylation Specificity

Both unmethylated and in-vitro methylated lambda DNA were bound to a nitrocellulose membrane in varying quantities using a slot blotting apparatus. The Alexa 488 labeled MBD1 protein was then used to probe the entire blot. Following over night incubation at 4° C. the blot was washed and scanned with Typhoon imager to detect the Alexa Fluor 488 label. The results are shown in FIG. 26. This image demonstrates that the MBD1 probe binds to methylated DNA with high specificity.

Example 20

Parallel Fluidic Channels for High Throughput Multiplexed Molecular Analysis and Sorting The present invention provides for methods and devices having an array of parallel fluidic channels, where each channel has a width and depth less than one micron and a length of a few millimeters. This arrangement can allow for the interrogation of thousands of molecules per second in each of a plurality of channels. The number of channels that are arranged in a device can be about, greater than about, or up to about 1, 40, 100, 500, 1,000, 5,000, or 10,000.

Figure 28:
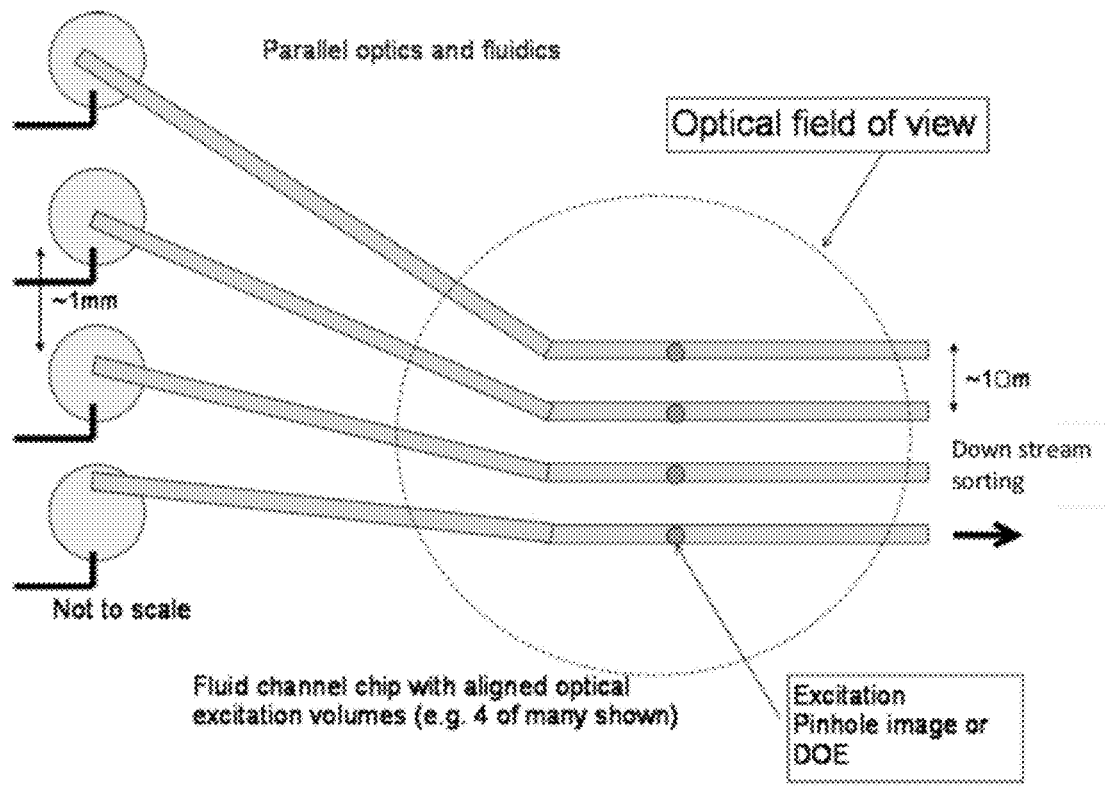
FIG. 28 depicts a schematic illustration of parallel fluidic channels with multiple input reservoirs.

For example, FIG. 28 shows a schematic illustration of parallel fluidic channels with multiple input reservoirs. The channels have an optical interrogation region where lasers or other near field excitation sources can excite fluorescent labels attached or bonded to single biomolecules. Alternatively, the parallel channels may have a common input reservoir or individual reservoirs where a collection of molecules, including native DNA, chromatin, RNA, proteins, polysaccharides, or small molecule drugs, is loaded.

Figure 29:
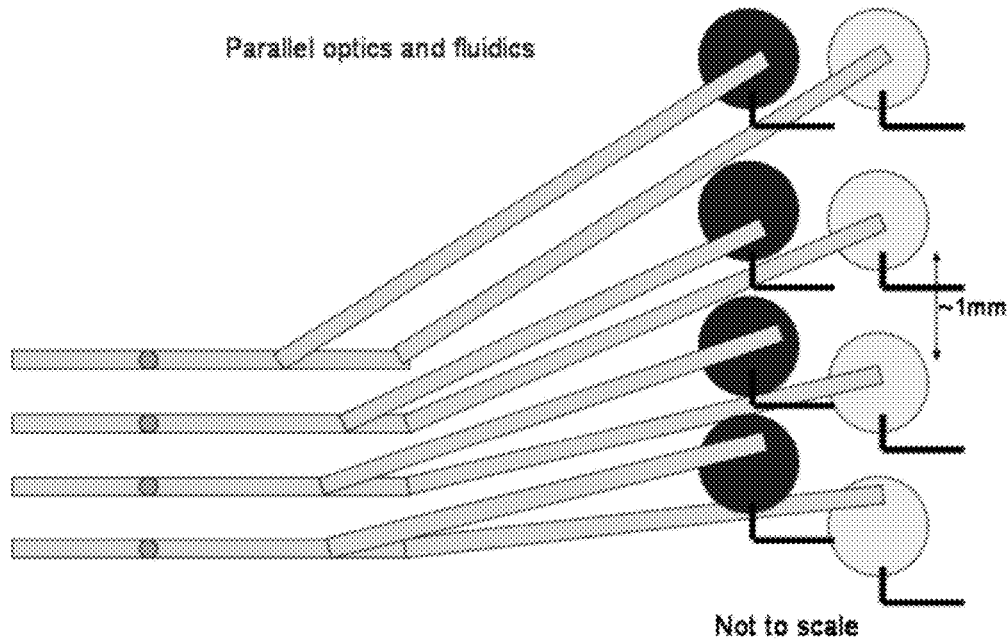
FIG. 29 depicts a schematic illustration of parallel fluidic channels with multiple output reservoirs.
Figure 30:
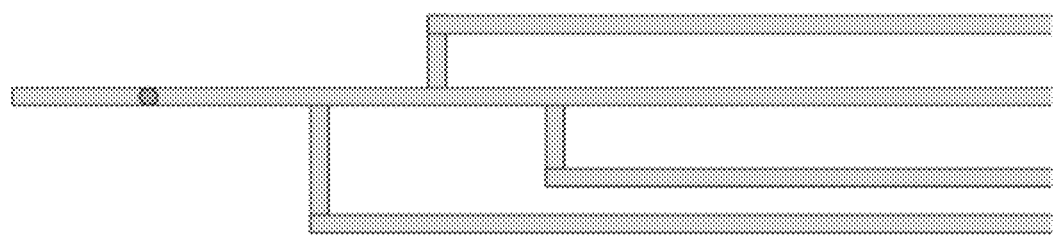
FIG. 30 depicts a schematic illustration of a single input fluidic channel leading to several possible output fluidic channels.

FIG. 29 shows a schematic illustration of parallel fluidic channels with multiple output reservoirs. As indicated, each channel has two potential output channels that molecules can be switched between depending on the measured value of some fluorescent or electrical or other property of the molecule detected when it traversed the excitation volume. As shown in FIG. 30, each of the parallel input channels can be interrogated at multiple locations leading to multiple possible output paths based on the measurements made at each interrogation zone. As shown in FIG. 30, four potential output path channels may be connected to each parallel input channel.

Alternatively, the parallel channels may also have a common output reservoir where the analyzed molecules are deposited.

Figure 31:
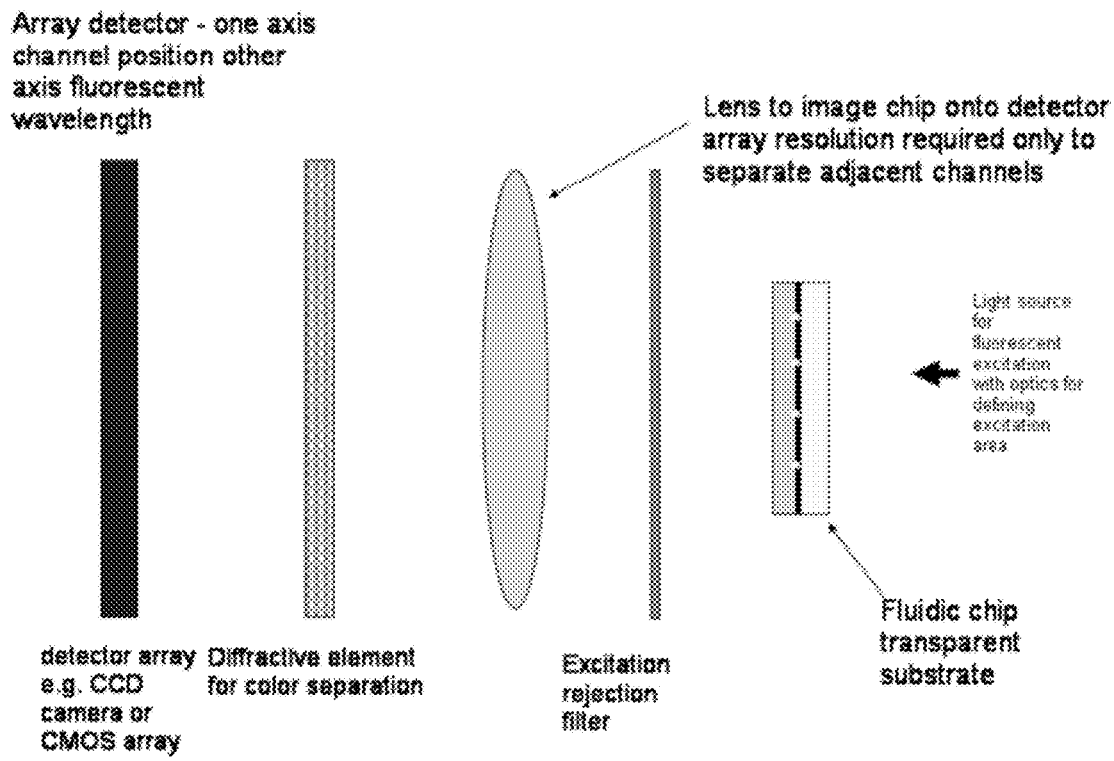
FIG. 31 depicts a schematic illustration of a fluidic chip interrogated optically with a lens for imaging the resulting fluorescent emission from each channel independently on a CCD, CMOS array or other arrayed photodetector.

The devices for detection can be configured to analyze the plurality of channels in a variety of manners. For example, FIG. 31 shows a schematic illustration of a fluidic chip interrogated optically with a lens for imaging the resulting fluorescent emission from each channel independently on a CCD, CMOS array or other arrayed photodetector. The schematic illustrates a diffractive element that separates different wavelength emission fluorescence transverse to the incoming excitation light, allowing each channel to be imaged on the photodetector along a separate axis. This allows for multiplexed analysis of each biomolecules (detection of several separate probes indicating the presence of various biological marks) for each parallel fluidic channel.

Figure 32:
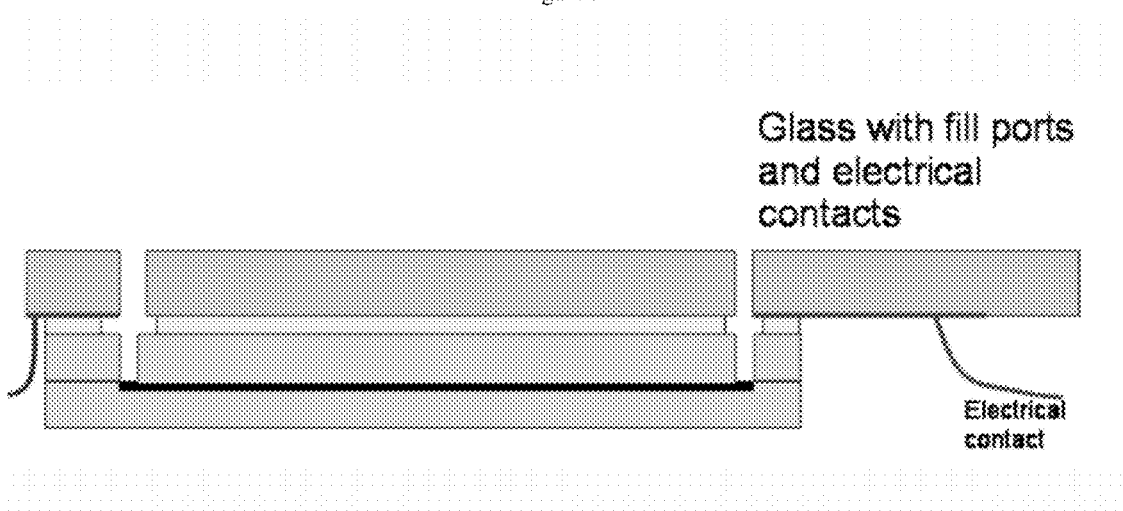
FIG. 32 depicts a schematic illustration of a method of fabricating a device with parallel fluidic channels.

A method of fabricating a device having a plurality of channels is shown in FIG. 32. Referring to FIG. 32, the bottom substrate can be made of fused silica that has been patterned using nanolithography or microlithography techniques to include thousands of parallel fluidic channels. The bottom substrate can be bonded to a second fused silica wafer with access holes for fluidic reservoirs. The second fused layer can have a PDMS gasket on top for bonding to a final glass layer containing larger ports and integrated electrical contacts for controlling electrophoretic flow within the channels.

Figure 33:
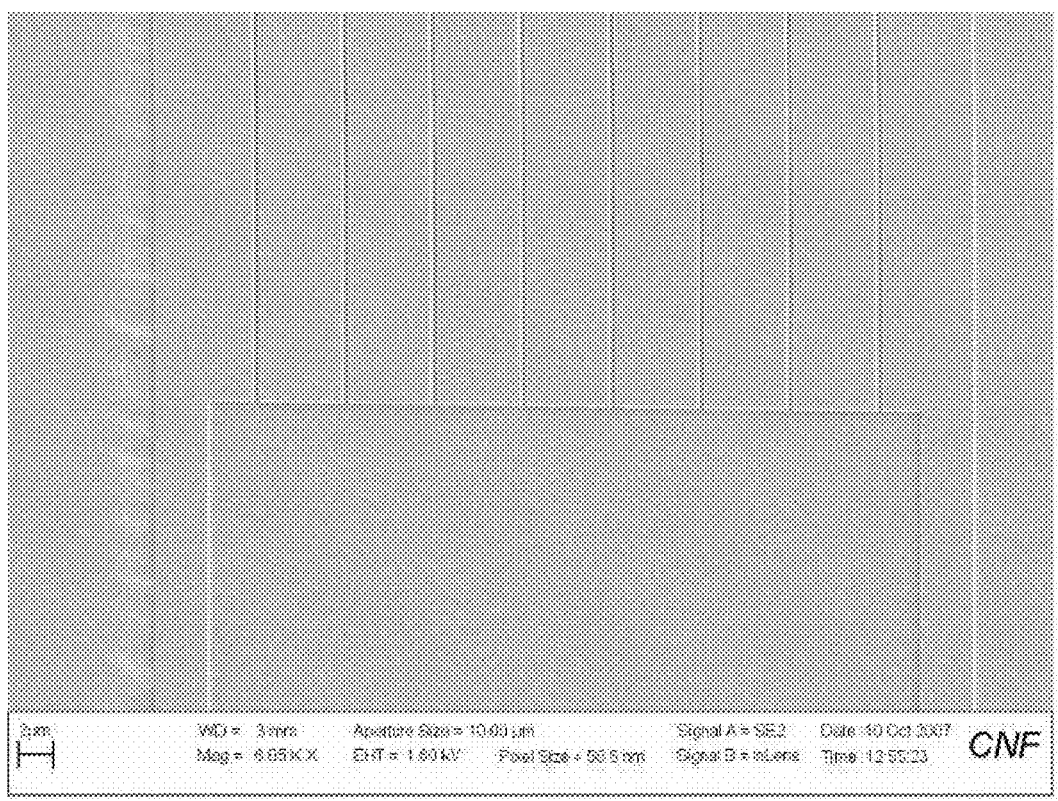
FIG. 33 depicts a scanning electron micrograph of eight parallel fluidic channels fabricated in a fused silica wafer.

A scanning electron micrograph of an exemplary device is shown in FIG. 33. As shown in FIG. 33, each channel is approximately 150 nm wide and deep with a length of ~100 microns. The channels are made by reactive ion etching fused silica after it being patterned with a negative tone electron beam resist. The wafer is subsequently bonded to a cover wafer containing reservoir holes where DNA molecules can be introduced and electrophoretically driven through the channels.

Figure 34:
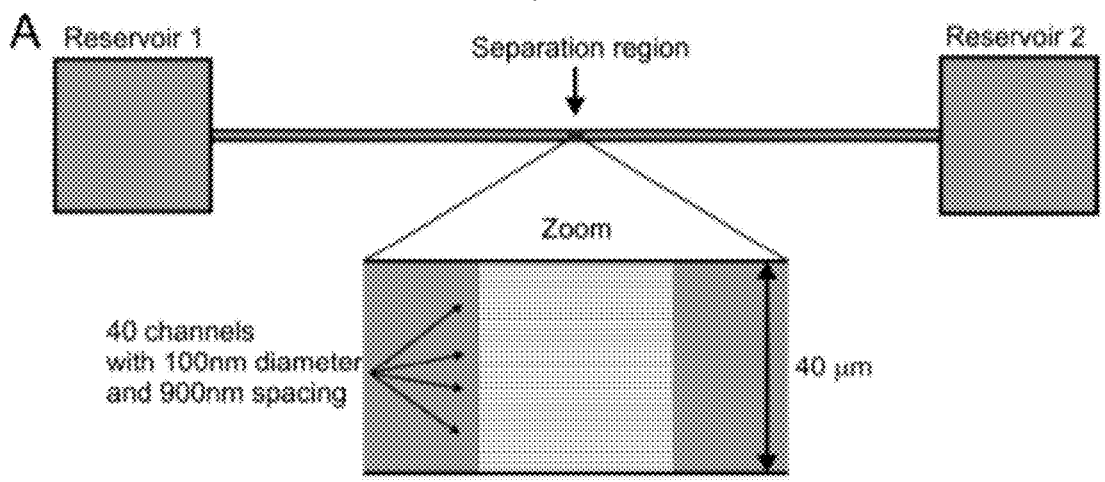
FIG. 34 depicts a schematic illustration of a device having a common input and output reservoirs and a central region of 40 parallel nanofluidic channels.

FIG. 34 shows a schematic of a device having common input and output reservoirs and a central region of 40 parallel nanofluidic channels. This device does not contain separate sorting capability for each channel, as described elsewhere herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for performing epigenetic analysis of native chromatin in a channel, comprising:
   (a) flowing the native chromatin into an interrogation volume that is illuminated with a beam of light in said channel, wherein said native chromatin is labeled with a plurality of labels, at least one of which is specifically complexed with an epigenetic marker on said native chromatin, and at least one other label is complexed with a protein and/or nucleotide of said native chromatin
   (b) detecting the at least one label and the at least one other label within the interrogation volume using an imaging device and
   (c) analyzing said detection of the at least one label and the at least one other label, thereby performing said epigenetic analysis.

2. The method of claim 1, wherein the imaging device is an arrayed photodetector.

3. The method of claim 1, wherein the imaging device is a CCD.

4. The method of claim 1, wherein the imaging device is a CMOS array.

5. The method of claim 1, wherein the at least one label and the at least one other label are detected simultaneously.

6. The method of claim 1, comprising detecting at least three or four labels.

7. The method of claim 1, wherein the at least one other label is complexed with a histone or is a nucleic acid binding agent selected from the group consisting of sequence specific probe, intercalating dye, minor groove binder, and DNA binding proteins.

8. The method of claim 1, wherein the at least one other label is complexed with a binding agent that complexes with a target selected from the group consisting of a non-histone protein, a transcription factor, MBD1, RNA Pol II, and RNA.

9. The method of claim 1, wherein the detecting step provides a time-dependent resolution of better than about 10 microseconds.

10. The method of claim 1, wherein the native chromatin comprises a nucleic acid molecule and a histone.

11. The method of claim 1, wherein the illuminated interrogation volume contains a single native chromatin.

12. The method of claim 1, wherein the interrogation volume is less than about 0.5 femtoliters.

13. The method of claim 1, wherein the genetic material is characterized in less than about 0.1 seconds.

14. The method of claim 1, wherein said interrogation volume is defined by (a) walls of a submicrometer channel region that are separated by a width of less than about 1 µm of said channel and (b) said beam of light.

* * * * *